(12) United States Patent
Liao et al.

(10) Patent No.: US 12,144,910 B2
(45) Date of Patent: Nov. 19, 2024

(54) METHODS OF COATING ANTIMICROBIAL PEPTIDES ON THE BIOMATERIAL AND THE BIOMATERIAL COATED THEREBY

(71) Applicant: ACADEMIA SINICA, Taipei (TW)

(72) Inventors: You-Di Liao, Taipei (TW); Dan-Wei Wang, New Taipei (TW); Eden Wu, Jiaoxi Township (TW); Shih-Han Wang, Taipei (TW); Wen-Hung Tang, Taichung (TW)

(73) Assignee: ACADEMIA SINICA, Taipei (TW)

( * ) Notice: Subject to any disclaimer, the term of this patent is extended or adjusted under 35 U.S.C. 154(b) by 73 days.

(21) Appl. No.: 17/604,318

(22) PCT Filed: Apr. 16, 2020

(86) PCT No.: PCT/US2020/028554
§ 371 (c)(1),
(2) Date: Oct. 15, 2021

(87) PCT Pub. No.: WO2020/214836
PCT Pub. Date: Oct. 22, 2020

(65) Prior Publication Data
US 2022/0226545 A1    Jul. 21, 2022

Related U.S. Application Data

(60) Provisional application No. 62/834,844, filed on Apr. 16, 2019.

(51) Int. Cl.
*A61L 27/54* (2006.01)
*A61L 29/16* (2006.01)
*A61L 31/16* (2006.01)

(52) U.S. Cl.
CPC .............. *A61L 27/54* (2013.01); *A61L 29/16* (2013.01); *A61L 31/16* (2013.01); *A61L 2300/252* (2013.01); *A61L 2300/404* (2013.01); *A61L 2300/606* (2013.01); *A61L 2420/02* (2013.01)

(58) Field of Classification Search
None
See application file for complete search history.

(56) References Cited

U.S. PATENT DOCUMENTS

| 6,635,269 B1 | 10/2003 | Jennissen |
| 6,835,536 B2 | 12/2004 | Krieger et al. |
| 7,282,214 B2 | 10/2007 | Willcox et al. |
| 8,414,910 B2 | 4/2013 | Wang |
| 2007/0254006 A1 | 11/2007 | Loose et al. |
| 2009/0155335 A1 | 6/2009 | O'Shaughnessey et al. |
| 2013/0225481 A1* | 8/2013 | Yang ........................ A61P 31/04 530/300 |
| 2018/0194967 A1* | 7/2018 | Ulery ..................... A01N 37/46 |

FOREIGN PATENT DOCUMENTS

WO    WO-2015088344 A1 *  6/2015  ............. A01N 43/38

OTHER PUBLICATIONS

Chang et al. (PLoS ONE 12(10):e0186442, 2017) (Year: 2017).*
Narayana et al. (Oncotarget. May 30, 2015; 6(15): 12936-12954) (Year: 2015).*
Brogden, K.A. et al., "The Ovine Cathelicidin SMAP29 Kills Ovine Respiratory Pathogens In Vitro and in an Ovine Model of Pulmonary Infection," Antimicrob. Agents and Chem., Jan. 2001, 45(1):331-334.
Chang, Ting-Wei et al., "Hydrophobic residues are critical for the helix-forming, hemolytic and bactericidal activities of amphipathic antimicrobial peptide TP4," PLOS, Oct. 17, 2017, 22 pages.
De Breij, Anna et al., "The antimicrobial peptide SAAP-148 combats drug-resistant bacteria and biofilms," Sci. Transl. Med., Jan. 10, 2018, vol. 10, 14 pages.
Gopal, Ramamourthy et al., "Synergistic Effects and Antibiofilm Properties of Chimeric Peptides against Multidrug-Resistant Acinetobacter baumannii Strains," AAC, Mar. 2014, 58(3):1622-1629.
International Search Report and Written Opinion issued on Jul. 22, 2020 in International Patent Application No. PCT/US20/28554.
Mohamed, Mohamed F. et al., "Targeting Methicillin-Resistant *Staphylococcus aureus* with Short Salt-Resistant Synthetic Peptides," AAC, Jul. 2014, vol. 58, No. 7, pp. 4113-4122.
Office Action and Search Report from Taiwan Patent Application No. 228320 dated Mar. 31, 2021.
Rhoades, Alicyn M. et al., "Interactions of an antimicrobial peptide (Ac-RRWWRF-NH2) and surfactants: Towards antimicrobial peptide additives for coatings applications," Progress in Organic Coatings, (2007), vol. 58, pp. 209-216.
Zhu, Xin et al., "Importance of Tryptophan in Transforming an Amphipathic Peptide into a Pseudomonas aeruginosa-Targeted Antimicrobial Peptide," PLOS, Dec. 10, 2014, 19 pages.

* cited by examiner

*Primary Examiner* — Sergio Coffa
(74) *Attorney, Agent, or Firm* — Prosyla Group PC

(57) ABSTRACT

The present invention pertains to methods of coating antimicrobial peptides on the biomaterial and the biomaterial coated thereby. The coating solution described herein comprises one or more antimicrobial peptides (AMPs) dissolved in a buffer containing an anionic surfactant, wherein the AMPs are amphipathic and cationic.

16 Claims, 37 Drawing Sheets
Specification includes a Sequence Listing.

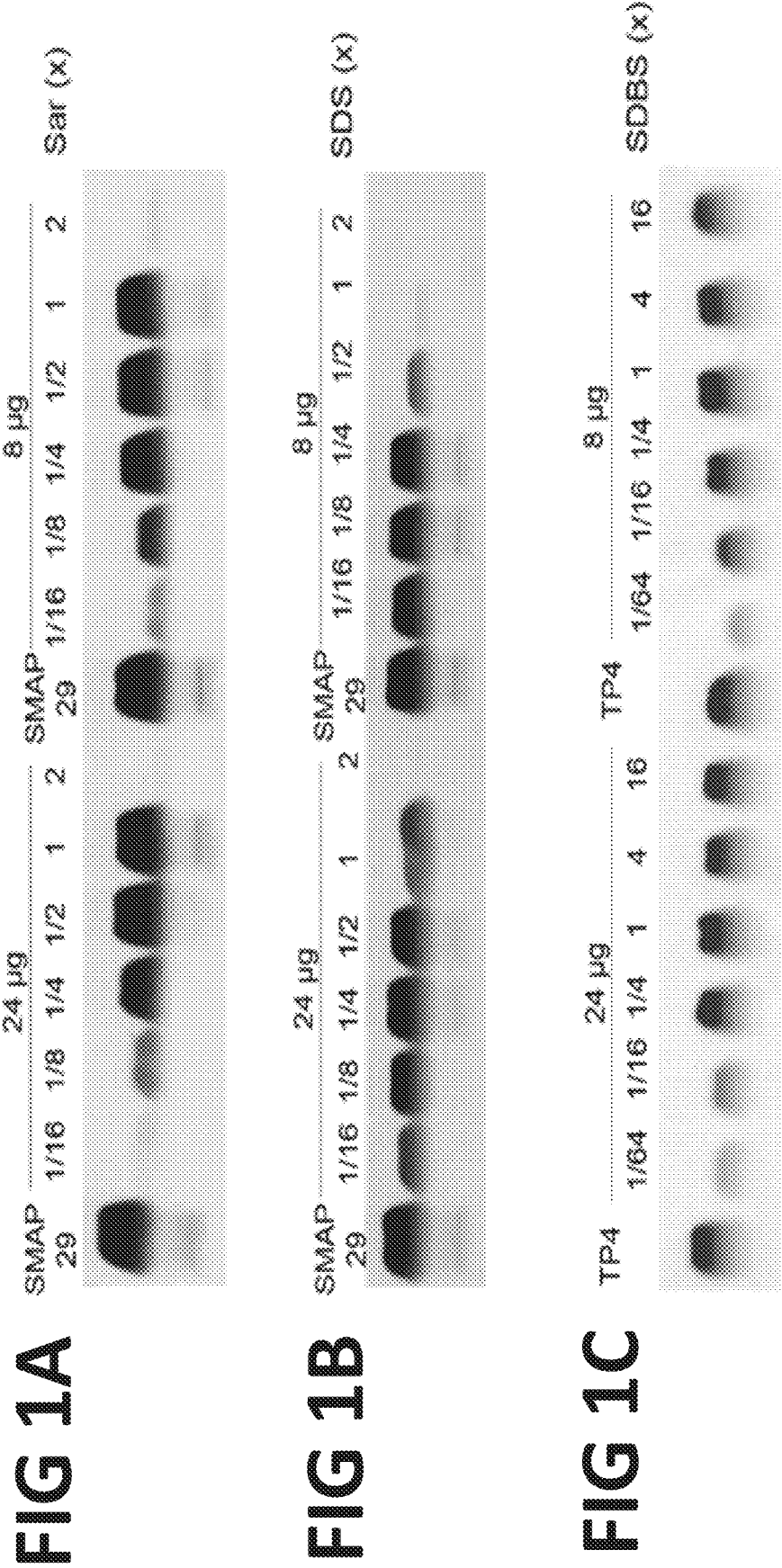

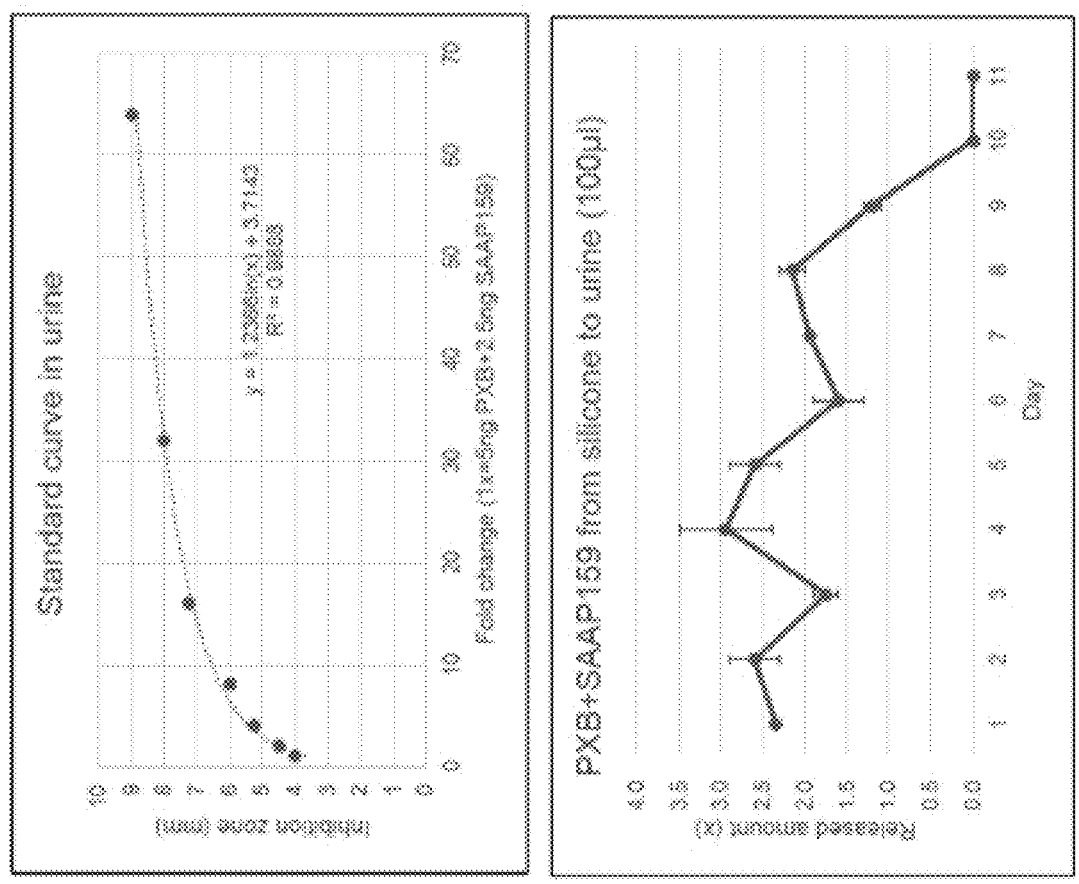
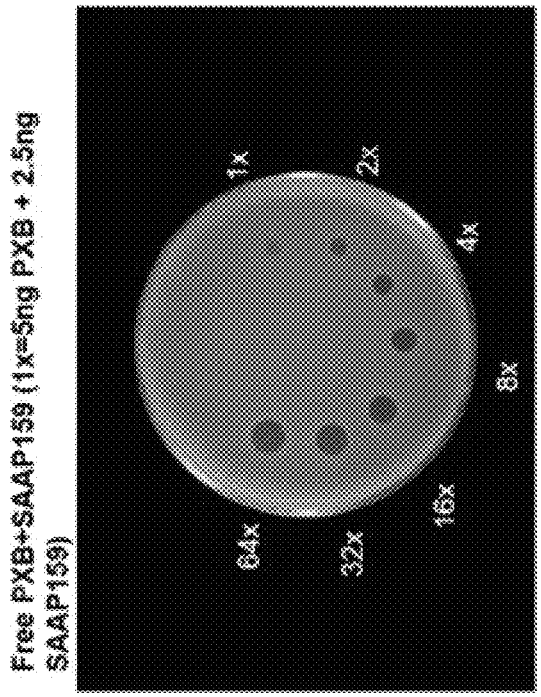
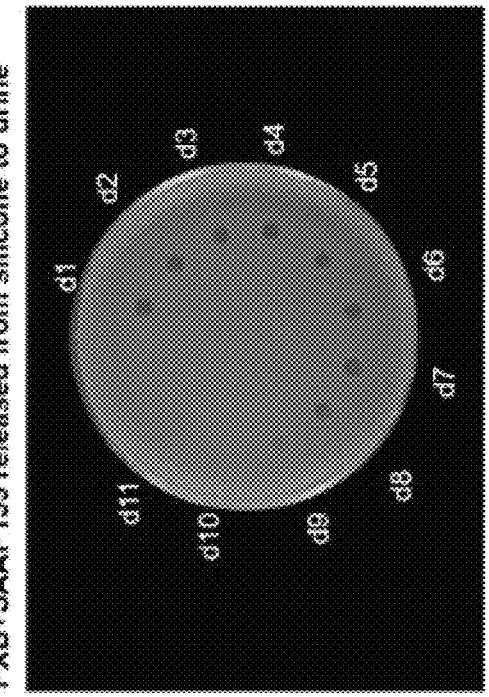
FIG. 7A

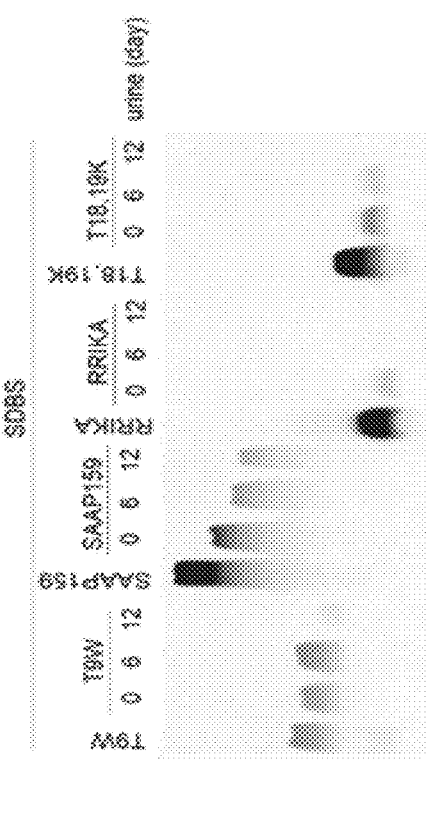
FIG. 10D
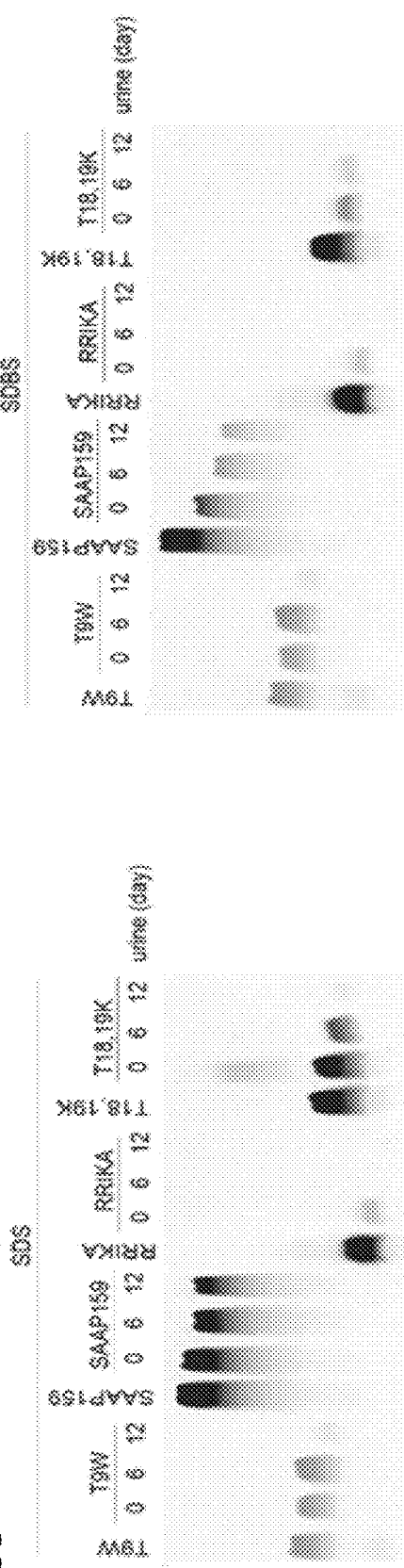
FIG. 10C
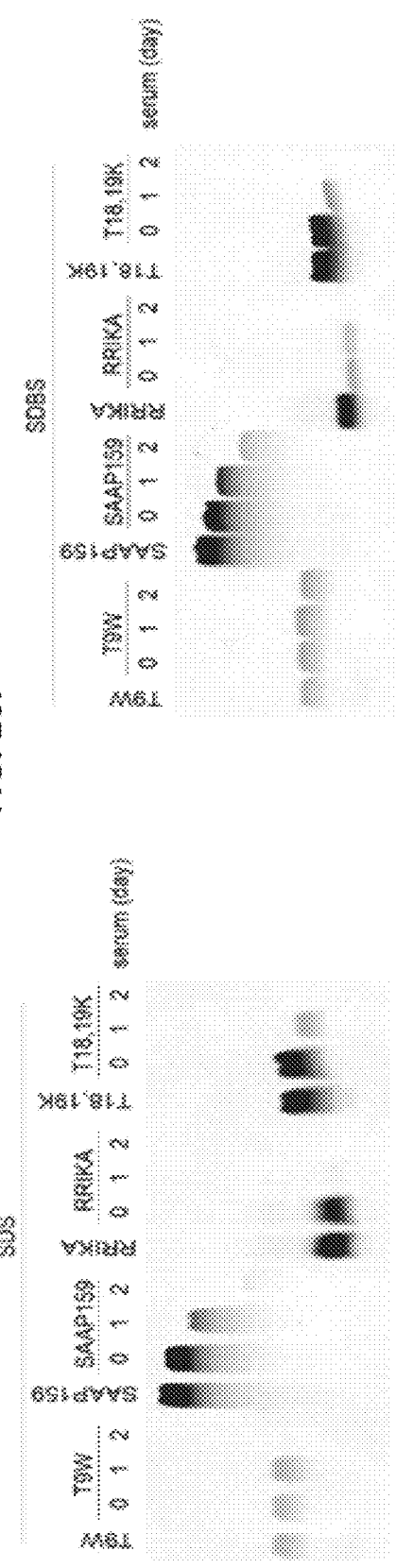
FIG. 10F
FIG. 10E

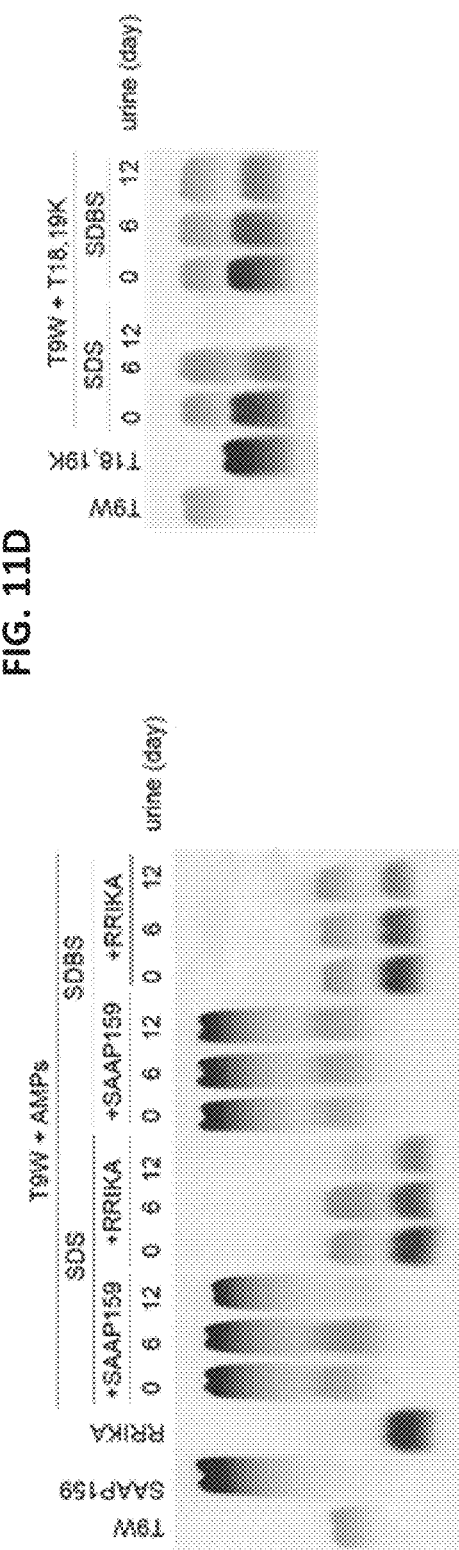
FIG. 11C
FIG. 11D
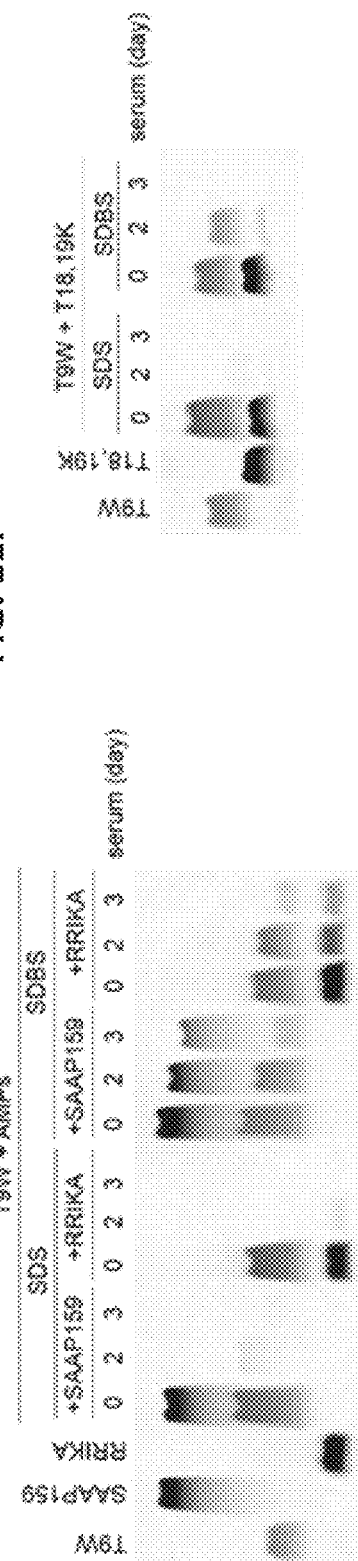
FIG. 11E
FIG. 11F

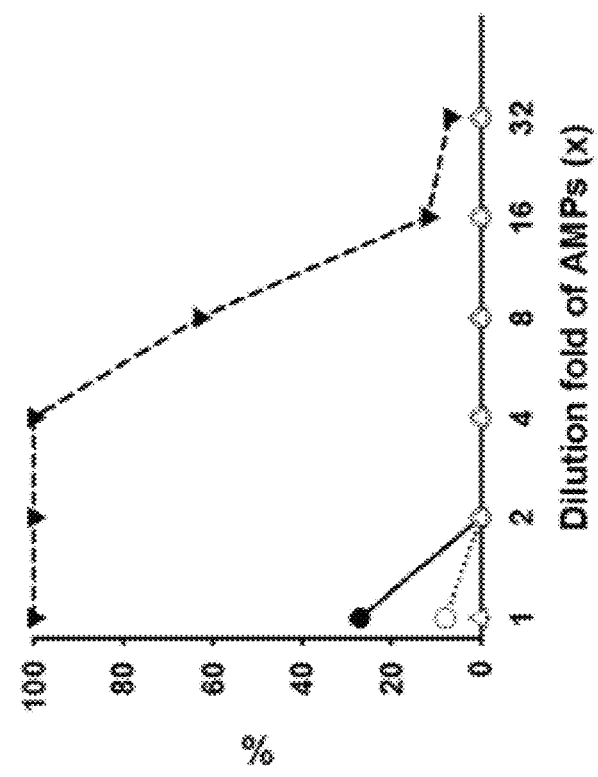
FIG. 20D
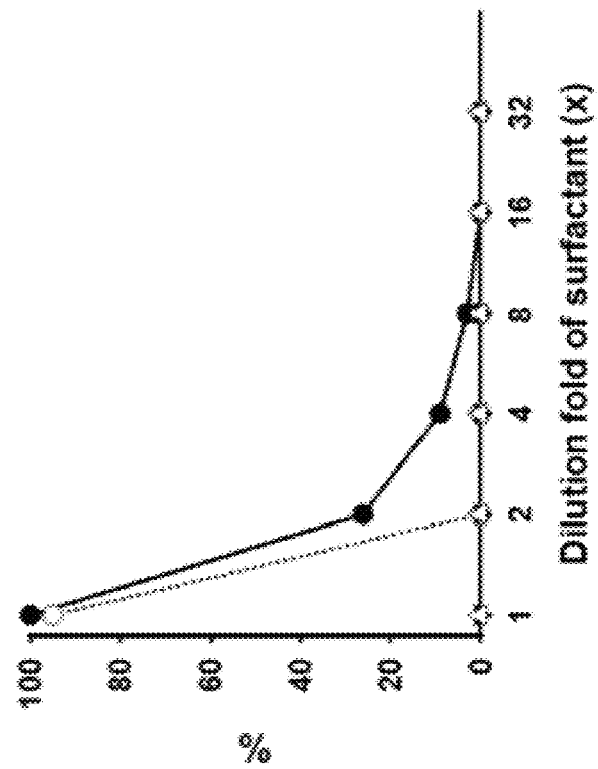
FIG. 20B
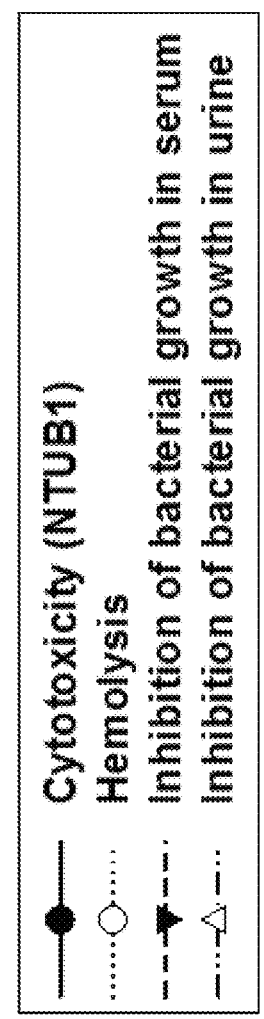

METHODS OF COATING ANTIMICROBIAL PEPTIDES ON THE BIOMATERIAL AND THE BIOMATERIAL COATED THEREBY

This application claims the benefit and priority to International Patent Application No. PCT/US20/28554, filed Apr. 16, 2020, which claims benefit and priority to U.S. Provisional Application No. 62/834,844, filed on Apr. 16, 2019, entitled, "METHOD OF COATING AN ANTIMICROBIAL PEPTIDE ON THE BIOMATERIAL AND THE BIOMATERIAL COATED THEREBY", the contents of which is incorporated by reference herewith in its entirety.

SEQUENCE LISTING

The instant application contains a Sequence Listing which has been submitted electronically in ASCII format and is hereby incorporated by reference in its entirety. Said ASCII copy, created on Jun. 23, 2020, is named G4590-04900NP_SeqList_20211014.txt and is 10 kilobytes in size.

FIELD OF THE INVENTION

The present invention relates to a field of coating antimicrobial peptides on a biomaterial. Particularly, the present invention pertains to methods of coating antimicrobial peptides on the biomaterial and the biomaterial coated thereby.

BACKGROUND OF THE INVENTION

Medical devices including catheters, artificial heart valves, prosthetic joints and other implants are widely used in modern medicine. Such medical devices are generally used to restore body function and increase life quality, but biomaterial-associated infections (BAI) are still a major problem. The risk of BAI may in part be the reduced efficacy of local immune defense induced by the invasive devices. Another contributing factor of BAI is the adherence of bacteria to the devices and formation of a biofilm from which they can invade the peri-implant tissues and cause an infection. Much higher concentrations of antibiotics are required to inhibit or eradicate the biofilm than are needed for planktonic bacteria. Failure of antibiotic treatment usually leads to removal of the medical device and replacement with a new device at a different location in the body.

Bacterial biofilm formation is considered to play a major role in the pathogenesis of BAI. It is initiated by bacterial adherence to the surfaces of medical devices, followed by cell replication and production of extracellular matrix consisting of bacteria, bacterial exopolysaccharides, proteins, extracellular DNA and host proteins. The bacteria in the biofilm are more tolerant to antibiotics and less susceptible to cells and molecules of the human immune defense system than planktonic counterparts. These metabolically-inactive and antibiotic tolerant bacteria are able to multiply even after antibiotic treatment, leading to the recurrence of BAI.

Antimicrobial peptides (AMPs) are effector molecules of the innate defense of animals, plants and microorganisms. They display antimicrobial activity against bacteria residing within the biofilm that are resistant to antibiotics. AMPs are mostly amphipathic and cationic peptides that display broad antimicrobial activity against bacteria, fungi and enveloped viruses. Although the exact target of AMPs on the bacteria has not been clearly identified, the bacterial membrane is known to become permeable within a few minutes after AMP treatment leading to cell death. Due to the rapid and non-specific mechanism of action, the development of drug resistance is very low.

For the prevention of BAI, AMPs have been developed to coat on the surface of various types of biomaterials. In addition, the coating can increase the half-life and reduce the side effect of AMPs in the body. Importantly, both the biofilm formation of bacteria on the implant and the colonization of bacteria in peri-implant tissue also need to be taken into consideration in designing prevention strategies. AMPs can also be immobilized on hydrogels which are composed of homo-polymers or co-polymers including but not limited to, polysaccharides, proteins, peptides, and coated on the substrate. The hydrogel is known to form a hydration layer on the surface of a catheter to inhibit nonspecific protein adsorption and reduces symptomatic catheter-associated urinary tract infection (CAUTI) occurrences (US 2007/0254006 A1; US 2009/0155335A1. US patents: U.S. Pat. No. 6,635,269 B1; U.S. Pat. No. 6,835,536 B2; U.S. Pat. No. 7,282,214 B2; U.S. Pat. No. 8,414,910 B2).

However, the coating of AMPs on an implant still involves various challenges, including loss of antimicrobial activities, nonspecific binding, altered peptide orientations, inadequate AMP concentration, non-optimal coating, pH sensitivity and hemolysis and cytotoxicity.

SUMMARY OF THE INVENTION

In one aspect, the present disclosure provides a coating solution, comprising one or more antimicrobial peptides (AMPs) dissolved in a buffer containing an anionic surfactant, wherein the AMPs are amphipathic and cationic. In one embodiment, the AMP is in an amount ranging from about 0.01% (w/v) to about 0.1% (w/v).

In another aspect, the present disclosure provides a method for coating the surface of a material, comprising (i) dissolving one or more antimicrobial peptides (AMPs) in an anionic surfactant and (ii) coating the resulting AMP solution onto the surface of the material so that the AMPs attach onto the surface. In one embodiment, the AMPs are in an amount ranging from about 0.01% (w/v) to about 0.1% (w/v). In one embodiment, the one or more antimicrobial peptides (AMPs) form a small vesicle-like structure after the AMP(s) dissolve in the anionic surfactant.

In another aspect, the present disclosure provides a method for coating the surface of a biomaterial, comprising (i) dissolving one or more antimicrobial peptides (AMPs) in a buffer containing a lower concentration anionic surfactant than 0.002% (w/v) to form solution (a); (ii) adding an amount of a buffer containing a higher concentration anionic surfactant than 0.02% (w/v) to the solution (a) to form solution (b), wherein the amount of a buffer containing a high concentration anionic surfactant is equal to that of the buffer containing a low concentration anionic surfactant; and (iii) coating the solution (b) onto the surface of the material so that the AMPs attach onto the surface. In one embodiment, the AMPs in a buffer containing a low concentration anionic surfactant are in an amount ranging from about 0.002% (w/v) to about 0.02% (w/v). In some embodiments, the AMP in a buffer containing a high concentration anionic surfactant are in an amount ranging from 0.02% (w/v) to about 0.6% (w/v).

In another aspect, the present disclosure provides a biomaterial, which is coated with one or more AMPs prepared by the method of the present disclosure.

In some embodiments, the anionic surfactant described herein includes, but is not limited to, sodium dodecyl sulfate (SDS), sodium lauroyl sarcosinate (sarkosyl), sodium 1-decane sulfonate (SDSn), sodium n-octyl sulfate (SOS) and sodium dodecyl benzene sulfonate (SDBS).

In some embodiments, the materials described herein include, but are not limited to, glass, synthetic polymer (such as silicone, polystyrene (PS), polypropylene (PP), polypropylene carbonate (PPC), polyvinyl chloride (PVC) or polyurethane (PU)), latex and metal (such as aluminum, stainless steel, titanium and titanium-based alloy). In some embodiments, the materials are used to make medical instruments/devices and supports. The medical instruments/devices and supports include, but are not limited to, film, particle (such as nanoparticle, micro-particle, bead), fiber (such as wound dressing, bandage, tape, pad, sponge), tube, frame, plate, catheter, stent, contact lens, bone implant, other surgical, dental instrument and/or medical device, which are coated with AMPs by the methods described herein.

In one embodiment, the AMPs described herein are peptide-derived antibiotics or cationic AMPs. In some embodiments, the AMPs described herein include, but are not limited to, α-helical, β-strand and coiled peptides. The AMPs are able to be coated on biomaterials by anionic surfactants.

In some embodiments, the antimicrobial peptide described herein includes, but is not limited to, an peptide-derived antibiotic,

```
BMAP-27 (L- and D-form):
                                   (SEQ ID NO: 1)
GRFKRFRKKFKKLFKKLSPVIPLLHLG
(D-form disclosed as SEQ ID NO: 24), CAME-A12K/K15H:
                                   (SEQ ID NO: 2)
KWKLFKKIGIGKVLHVLTTG-NH2, T18, 19K:
                                   (SEQ ID NO: 3)
KWKLFKKIGIGAVLKVLKKG-NH2, CAME-V16S:
                                   (SEQ ID NO: 4)
KWKLFKKIGIGAVLKSLTTG-NH2, CAP18:
                                   (SEQ ID NO: 5)
GLRKRLRKFRNKIKEKLKKIGQKIQGLLPKLAPRTDY, EPI (epinecidin-1):
                                   (SEQ ID NO: 6)
GFIFHIIKGLFHAGKMIHGLV,

GW-Q6:
                                   (SEQ ID NO: 7)
GIKIAKKAITIAKKIAKIYW,

Iseganan:
                                   (SEQ ID NO: 8)
RGGLCYCRGRFCVCVGR-NH, Latarcin 1:
                                   (SEQ ID NO: 9)
SMWSGMWRRKLKKLRNALKKKLKGE,

NLF20:
                                   (SEQ ID NO: 10)
NLFRKLTHRLFRRNFGYTLR,

NRC-12:
                                   (SEQ ID NO: 11)
GWKKWFNRAKKVGKTVGGLAVDHYL-NH2,
```

-continued
```
Pilosulin-1:
                                   (SEQ ID NO: 12)
GLGSVFGRLARILGRVIPKV-NH2, Pleurocidin:
                                   (SEQ ID NO: 13)
GWGSFFKKAAHVGKHVGKAALTHYL-NH2,

RR12:
                                   (SEQ ID NO: 14)
RRLIRLILRLLR-NH2,

RRIKA:
                                   (SEQ ID NO: 15)
WLRRIKAWLRRIKA,

SAAP159:
                                   (SEQ ID NO: 16)
LKRLYKRVFRLLKRYYRQLRRPVR,

SAAP145:
                                   (SEQ ID NO: 17)
LKRLYKRLAKLIKRLYRYLKKPVR,

SMAP-29:
                                   (SEQ ID NO: 18)
RGLRRLGRKIAHGVKKYGPTVLRIIRIAG-NH2,

SMAP-28-3:
                                   (SEQ ID NO: 19)
RGLRRLGRKIVHVVKKYLPTVLRIIRIA-NH2,

SMAP-28-3 + 2:
                                   (SEQ ID NO: 20)
RGLRRLGRKIVHVVKKYLPTVLRIIRRL-NH2,

TP4-A12, 15I:
                                   (SEQ ID NO: 21)
H-FIHHIIGGLFSAGKAIHRLIRRRRR-OH,

T9F:
                                   (SEQ ID NO: 22)
RFRRLRKKFRKRLKKI-NH2,
and T9W:
                                   (SEQ ID NO: 23)
RFRRLRKKWRKRLKKI-NH2.
```

In some embodiments, the AMP is an peptide-derived antibiotic, an peptide selected from SEQ ID Nos: 1 to 23 and a mixture of any two or more thereof.

In some embodiments, the AMP is an peptide-derived antibiotic, an peptide of SEQ ID NO:2, SEQ ID NO:3, SEQ ID NO:14, SEQ ID NO:15, SEQ ID NO:16, SEQ ID NO: 18, SEQ ID NO:20 or SEQ ID NO:23 or a mixture of any two or more thereof.

In some embodiments, one or two AMPs are used in the methods or materials described herein. In one embodiment, AMP pairs are used in the methods or materials described herein. In some embodiments, the AMP pair is an peptide-derived antibiotic in combination with any one of the peptides of SEQ ID Nos: 1 to 23. In some embodiments, the peptide-derived antibiotic includes, Polymyxin B, Polymyxin E or Gentamicin. In some embodiments, the AMP pair is an peptide-derived antibiotic in combination with any one of the peptides of SEQ ID Nos: 1 to 23. In some embodiments, the AMP pair is any one of Polymyxin B, Polymyxin E and Gentamicin in combination with any one of the peptides of SEQ ID Nos: 1 to 23. In some embodiments, the AMP pair is any one of Polymyxin B, Polymyxin E and Gentamicin in combination with any one of the peptide of SEQ ID NO:2, SEQ ID NO:3, SEQ ID NO:16 or SEQ ID NO: 18. In some embodiments, the AMP pair is SEQ ID NO:23 in combination with SEQ ID NO:3, SEQ ID NO:23 in combination with SEQ ID NO:14, SEQ ID NO:23 in combination with SEQ ID NO:15, SEQ ID NO:23 in combination with SEQ ID NO:16, SEQ ID NO:23 in combination with SEQ ID NO:20, SEQ ID NO:14 in combination with SEQ ID NO:16 or SEQ ID NO:14 in combination with SEQ ID NO:18.

In one aspect, the present disclosure provides an antimicrobial peptide, which is selected from the group consisting of: SEQ ID Nos: 2, 3, 4, 19 and 20. These antimicrobial peptides are novel peptides having antimicrobial activity.

BRIEF DESCRIPTION OF THE DRAWINGS

FIG. 1. Pulling down of antimicrobial peptide SMAP29 by centrifugation in the presence of anionic surfactants. SMAP29 peptides (24 µg or 8 µg) were dissolved in 60 µl sarkosyl buffer (A) or SDS buffer (B) at the indicated concentrations. TP4 peptides were dissolved in 60 µl SDBS buffer (C). The peptides were collected by centrifugation at 14,000×g for 15 min and subjected to 15% SDS-PAGE followed by Coomassie blue staining. 4 µg SMAP29 or TP4 peptides and their equivalents were taken for analysis. Sar, sarkosyl; SDS, sodium dodecyl sulfate; SDBS, sodium dodecylbenzenesulfonate.

RRIKA) coated by SDS and SDBS in the presence of urine (A) and 10% fetal bovine serum (B). (C) Stability of other paired AMPs as indicated in the presence of 10% fetal bovine serum treatment. 4 μg AMPs and their equivalents left on the silicone disc were taken for analysis by 15% SDS-PAGE.

Figure 13:
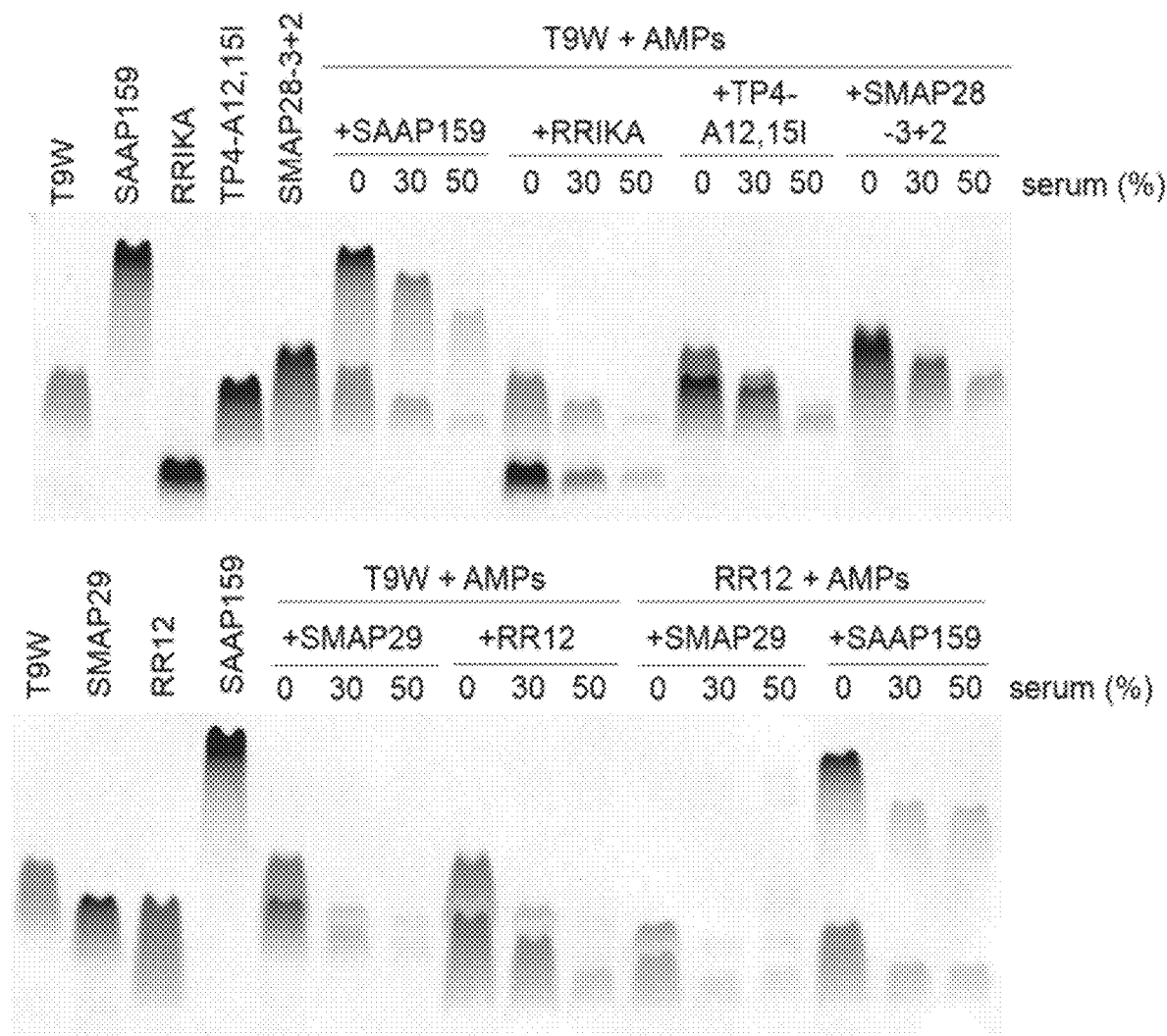

FIG. 13. Stability of paired AMPs coated on silicone disc by SDBS in serum. The paired AMPs as indicated were coated on silicone disc by SDBS and incubated with 30% and 50% fetal bovine serum overnight. 4 μg AMPs and their equivalents left on the disc were taken for analysis by 15% SDS-PAGE.

Figure 14A:
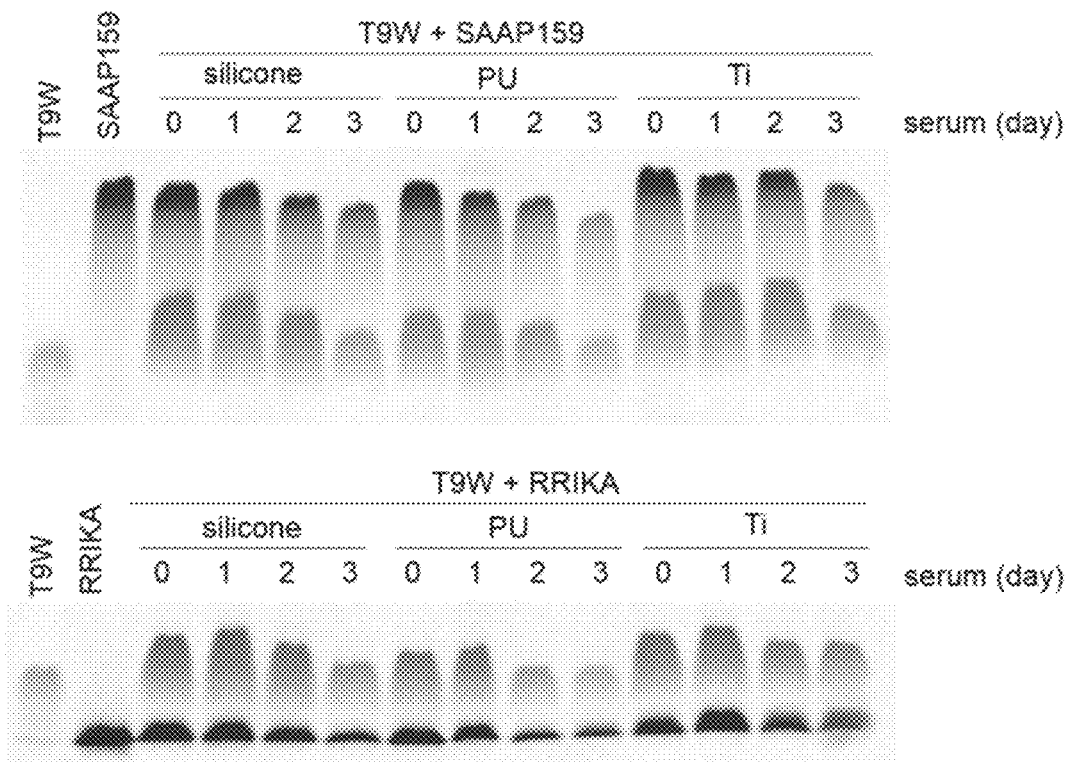

FIG. 14. Coating efficiency and stability of AMP pairs in serum coated on different materials. The AMP pairs (T9W+ SAAP159 and T9W+RRIKA) were coated on silicone, polyurethane and titanium discs by SDBS, and their stability in 10% fetal bovine serum (A) or 30% and 50% (B) was analyzed by 15% SDS-PAGE. 4 μg AMPs and their equivalents were taken for SDS-PAGE analysis. PU and Ti represent polyurethane and titanium, respectively.

FIG. 15. Cytotoxic, hemolytic and bactericidal activities of coated and released surfactant and paired AMPs. (A) The maximal amount of SDS (14 μg) and AMP pairs (12 μg each) that may be coated and released from silicone disc was employed for the assays. (B) The maximal amount of SDBS (25 μg) and AMP pairs (12 μg each) was employed for the assays. a and c present the total components of surfactant and T9W+SAAP159 or T9W+RRIKA, respectively, that were employed for coating. b and d present the released components in 200 μl of urine or 10% FBS overnight. NTUB1 cells were seeded at $1.5 \times 10^4$ cell/well for cytotoxic assay. Mouse red blood cells were seeded at $1.5 \times 10^7$ cells/well for hemolytic assay. E. coli 23502 was seeded at $3 \times 10^5$ cfu/ml for bactericidal assays in urine and 10% FBS.

FIG. 16. Prevention of urinary tract infection by paired AMPs in mouse model. The silicone tubing coated with T9W+SAAP159 (A, C) or T9W+RRIKA (B) were implanted into the bladder which had been instilled with 100 μl E. coli ATCC23502 ($5 \times 10^9$ cfu/ml for (A) and (B)) and P. aeruginosa 27853 ($3 \times 10^9$ cfu/ml for (C)) using a 24G I.V. catheter. The viable E. coli and P. aeruginosa cells in the urine collected at day 2, 4, 6 and 8 (a-d) and the bacteria adherent to bladder (e) and silicone tubing (f) after sacrifice at day 8 were counted. * indicates P≤0.05,  indicates P≤0.005, * indicates P≤0.0005 and n.s. indicates no significant difference.

Figure 17A:
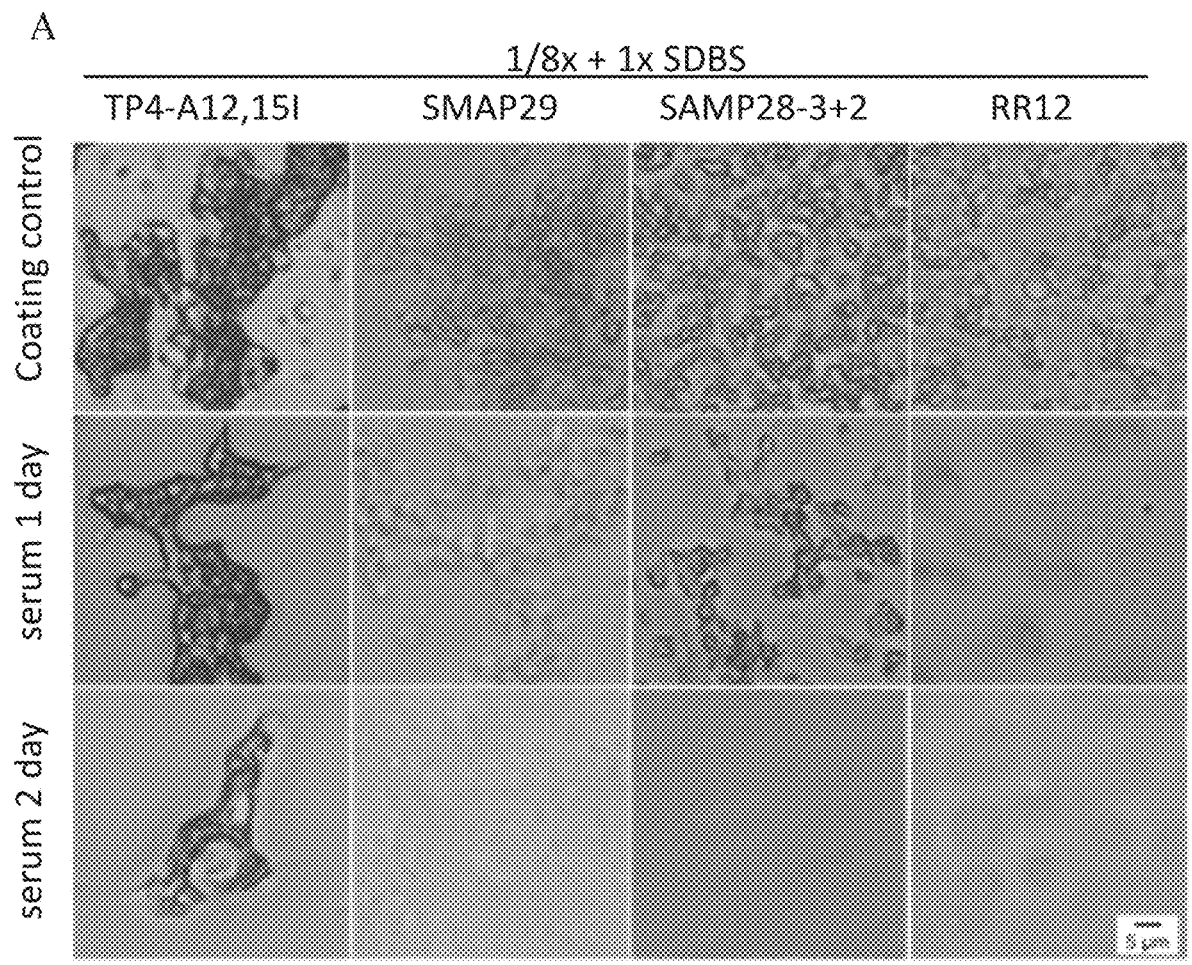
Figure 17B:
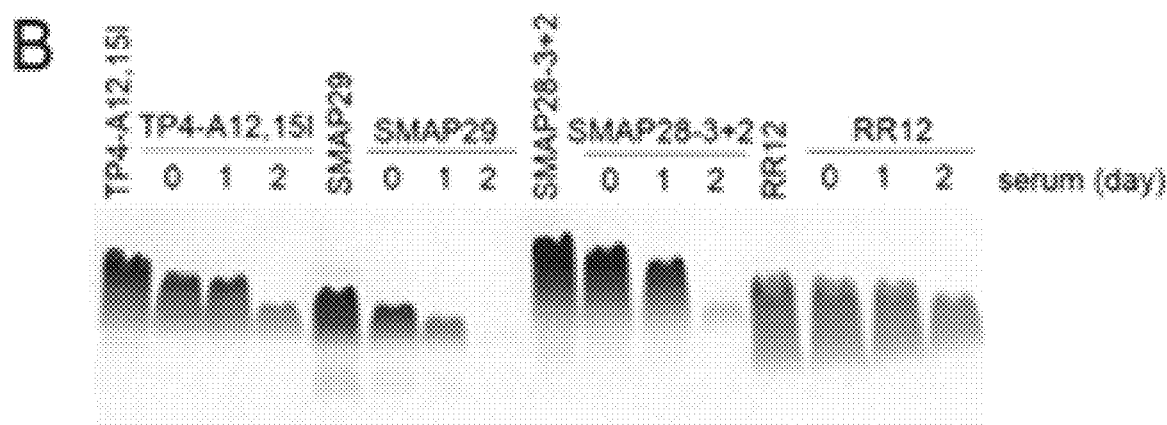

FIG. 17. Coating efficiency and stability of AMPs coated on polystyrene by SDBS. (A) Morphology of AMPs (TP4-A12,15I, SMAP29, SMAP28-3+2, and RR12) coated on polystyrene 96-well microplates by SDBS in the presence of 10% fetal bovine serum. (B) Stability of above AMPs analyzed by SDS-PAGE. 4 μg AMPs and their equivalents left in the well were taken for analysis by 15% SDS-PAGE.

Figure 18:
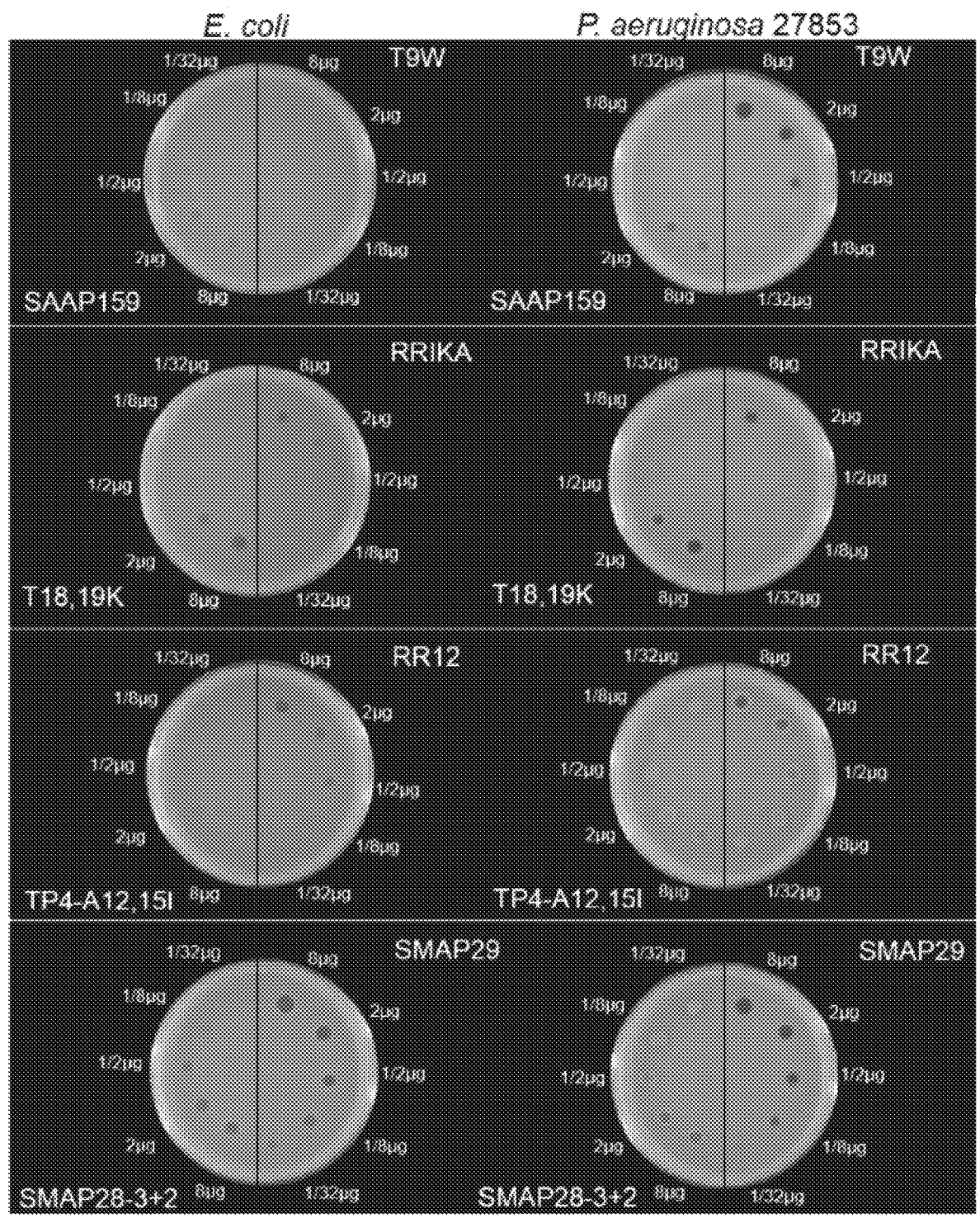
Figure 18:
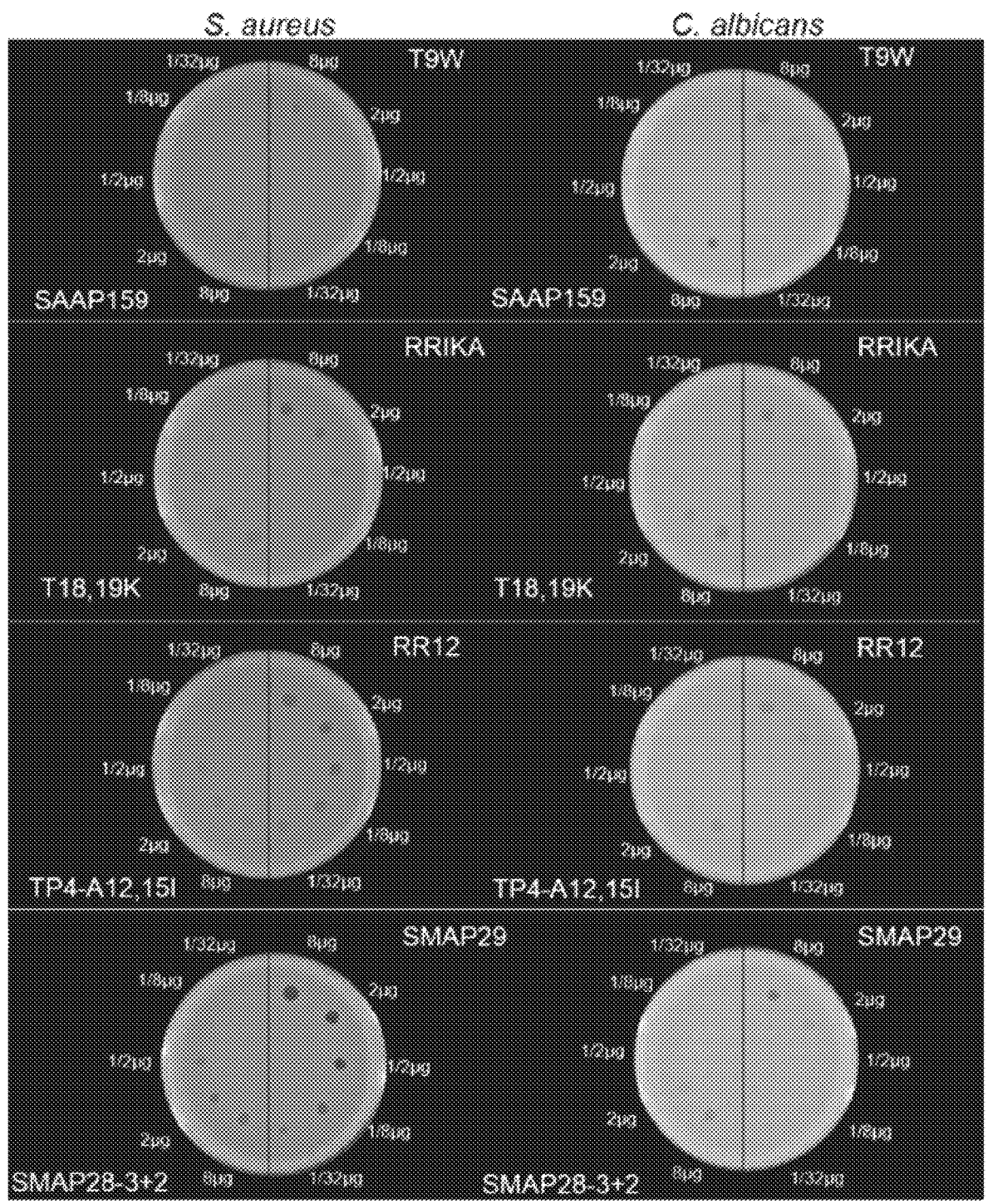
Figure 19A:
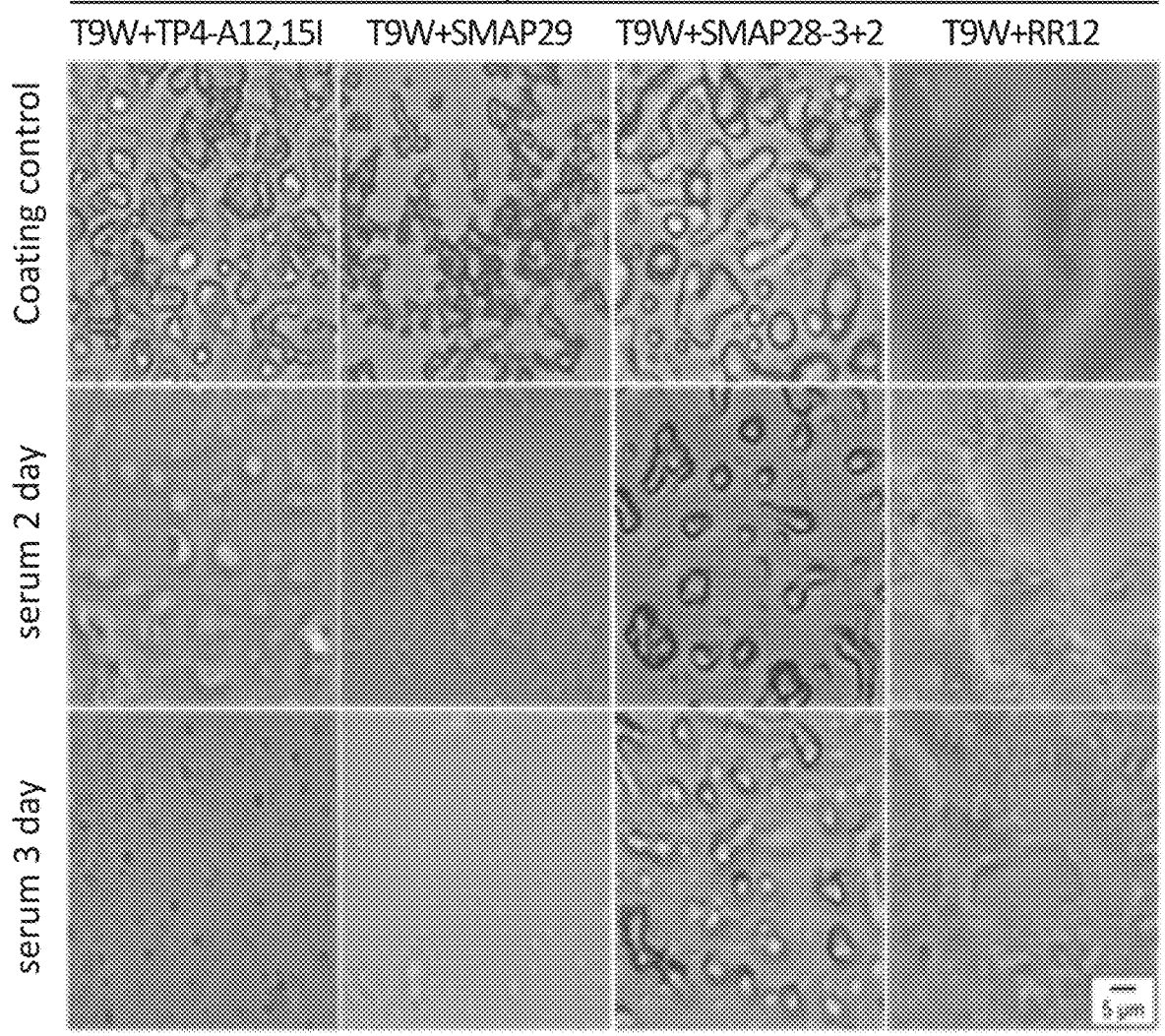
Figure 19B:
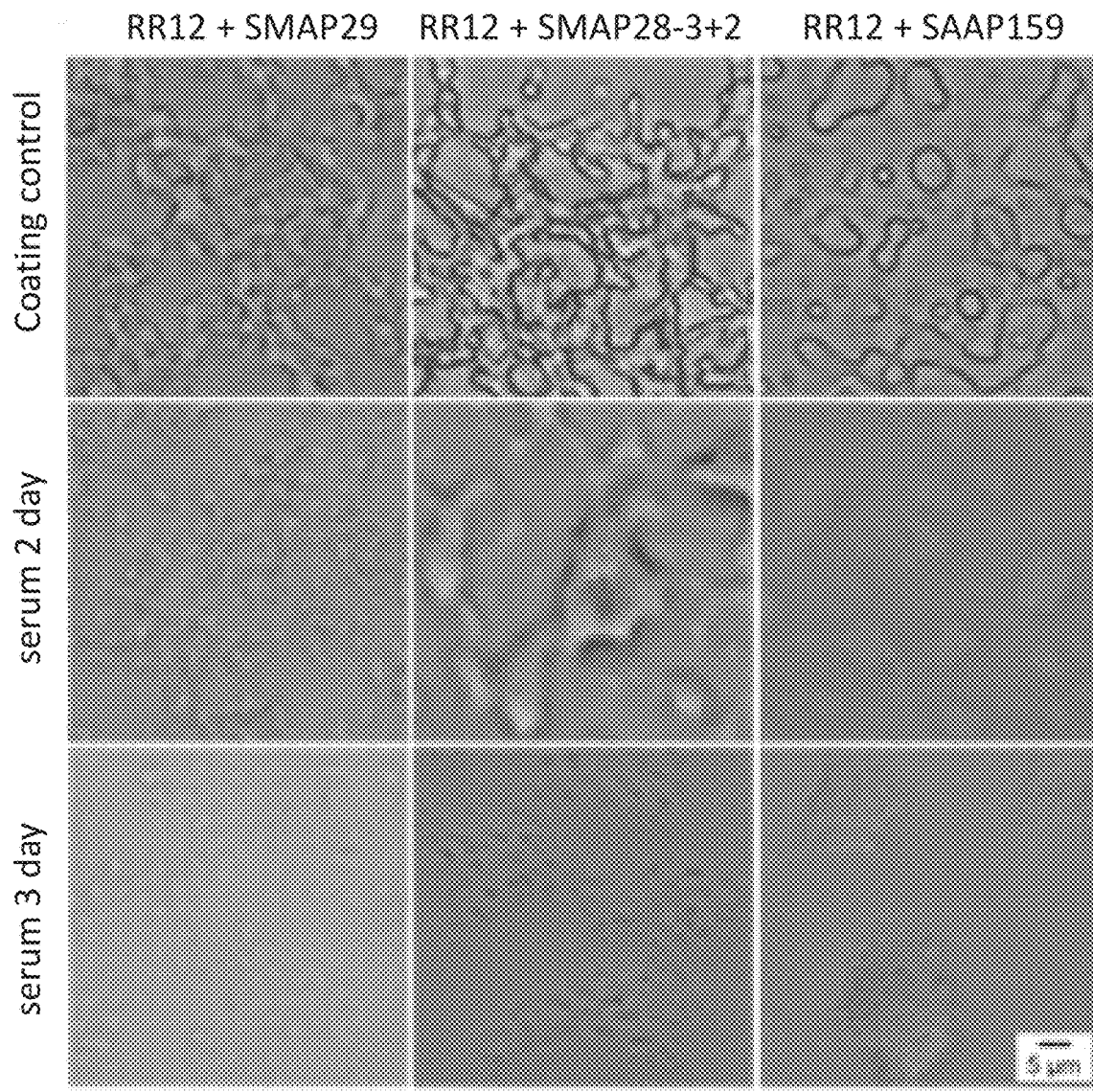
Figure 19C:
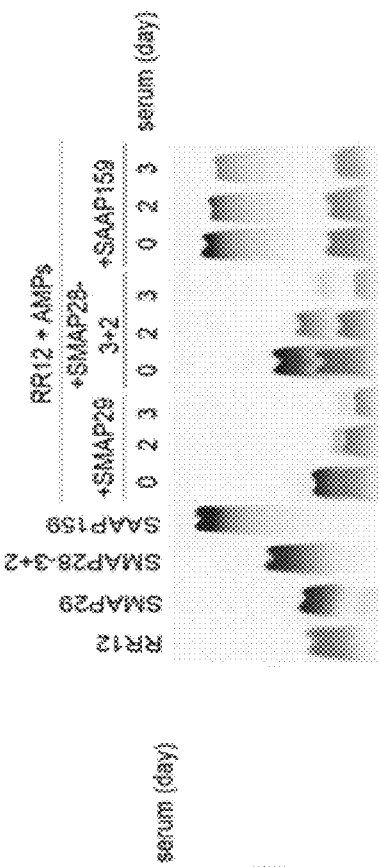
Figure 19D:
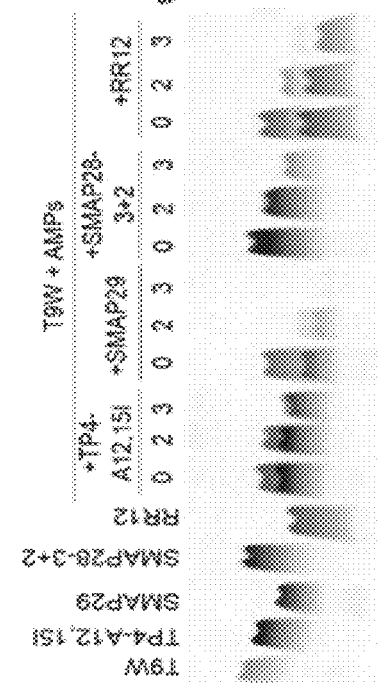

FIG. 18. Inhibition zone of AMPs on E. coli (ATCC 23502), Pseudomonas. aeruginosa 27853, Staphylococcus aureus, and Candida albicans. Two μl of AMP (T9W, SAAP159, RRIKA, T18,19K, RR12 TP4-A12,15I, SMAP29 and SMAP28-3+2) at the indicated dosage was dotted on microbes-containing agar plate.

FIG. 19. Coating efficiency and stability of paired AMPs coated on polystyrene by SDBS. (A-B) Morphologies of indicated AMP pairs coated by ½×+1×SDBS in the presence of serum. (C-D) Stabilities of above indicated AMP pairs in 10% fetal bovine serum. 4 μg AMPs and their equivalents left in the well were taken for analysis by 15% SDS-PAGE.

Figure 20C:
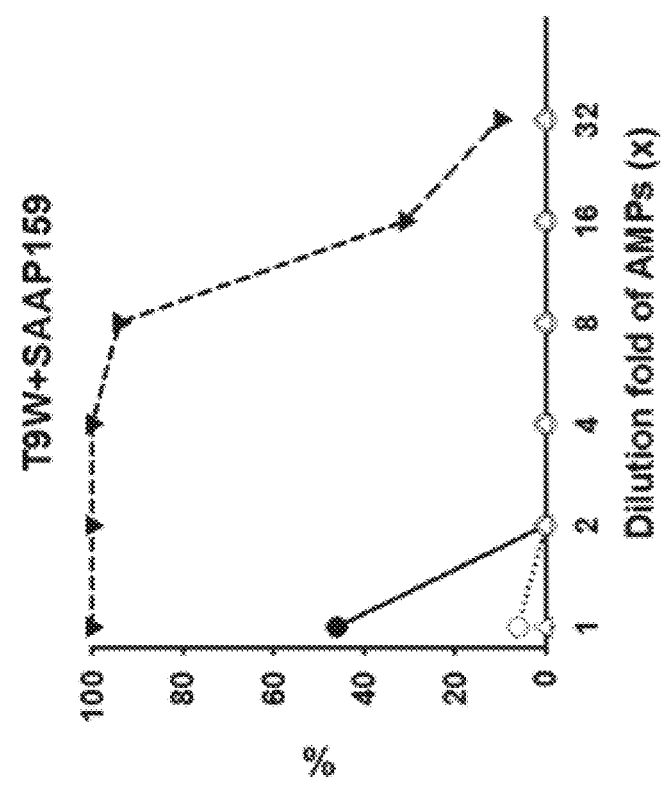

FIG. 20. Cytotoxic, hemolytic and bactericidal activities of surfactant and paired AMPs. The maximal amount of SDS (14 μg) for panel A, SDBS (25 μg) for panel B and AMP pairs (12 μg each) for panels C and D that may be coated and released from silicone disc were employed for the assays in 200 μl urine or 10% FBS. NTUB1 cells were seeded at $1.5 \times 10^4$ cell/well for cytotoxic assay. Mouse red blood cells were seeded at $1.5 \times 10^7$ cells/well for hemolytic assay. E. coli 23502 was seeded at $3 \times 10^5$ cfu/ml for bactericidal assays in urine and 10% FBS.

Figure 21A:
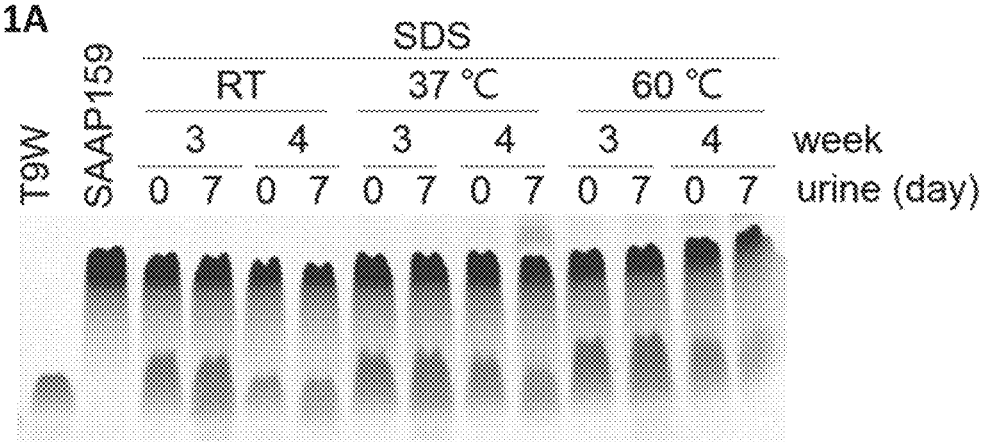
Figure 21B:
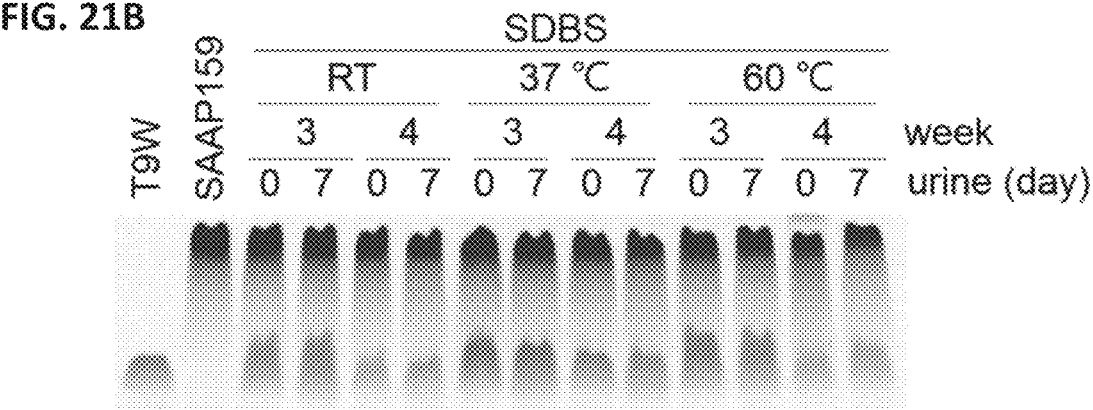

FIG. 21. Stability of paired AMPs in urine after heat or ethylene oxide treatment. The T9W+SAAP159 pairs coated on polystyrene microplates by SDS (A) or SDBS (B) were kept at room temperature, 37° C., and 60° C. for 4 weeks and their stabilities in urine were analyzed by 15% SDS-PAGE. Alternatively, the T9W/SAAP159 on microplates coated by SDS was sterilized by ethylene oxide (C) and their stability in urine was analyzed by SDS-PAGE. 4 μg AMP and their equivalents left in the well were taken for analysis. EO represents ethylene oxide.

DETAILED DESCRIPTION OF THE INVENTION

While the preparation and use of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Bacterial biofilm formation is considered to play a major role in the pathogenesis of BAI. It is initiated by bacterial adherence to the surfaces of medical devices, followed by cell replication and production of an extracellular matrix consisting of bacteria, bacterial exopolysaccharides, proteins, extracellular DNA and host proteins. The bacteria in the biofilm are more tolerant to antibiotics and less susceptible to cells and molecules of the human immune defense system than the planktonic counterparts. These metabolically-inactive and antibiotic tolerant bacteria are able to multiply even after antibiotic treatment, which leads to the recurrence of BAI.

The antimicrobial peptides (AMPs) are effector molecules of the innate defense of animals, plants and microorganisms. They display antimicrobial activity against bacteria resistant to antibiotics and residing within the biofilm. AMPs are mostly amphipathic and cationic peptides that display broad antimicrobial activity against bacteria, fungi and enveloped viruses. The AMPs described herein include, but are not limited to, α-helical, β-strand and coiled peptides. Examples of the AMPs include, but are not limited to, SEQ ID Nos: 1 to 23. Among the AMPs, the antimicrobial peptides, SEQ ID NOs: 2, 3, 4, 19 and 20, are novel peptides having antimicrobial activity. Certain example of the AMPs is the peptide of SEQ ID NO:2, SEQ ID NO:3, SEQ ID NO:14, SEQ ID NO:15, SEQ ID NO:16, SEQ ID NO: 18, SEQ ID NO:20 or SEQ ID NO:23 or a mixture of any two or more thereof.

One or more AMPs can be used in the present disclosure. Certain example is an AMP pair. The AMP pair is an peptide-derived antibiotic in combination with any one of the peptides of SEQ ID Nos: 1 to 23. Examples of the peptide-derived antibiotic include, but are not limited to, Polymyxin B, Polymyxin E and Gentamicin. In some embodiments, the AMP pair is any one of Polymyxin B, Polymyxin B, Polymyxin E and Gentamicin in combination with any one of the peptide of SEQ ID NO:2, SEQ ID NO:3, SEQ ID NO:16 or SEQ ID NO: 18. In some embodiments, the AMP pair is SEQ ID NO:23 in combination with SEQ ID NO:3, SEQ ID NO:23 in combination with SEQ ID NO:14, SEQ ID NO:23 in combination with SEQ ID NO:15, SEQ ID NO:23 in combination with SEQ ID NO:16, SEQ ID NO:23 in combination with SEQ ID NO:20, SEQ ID NO:14 in combination with SEQ ID NO:16 or SEQ ID NO:14 in combination with SEQ ID NO:18.

In the present disclosure, AMPs are dissolved in anionic surfactants. In one embodiment, the AMPs are in an amount ranging from about 0.01% (w/v) to about 0.1% (w/v). The AMPs in the emulsion are attached onto the surface of biomaterials. In one embodiment, the one or more antimicrobial peptides (AMPs) form a small vesicle-like structure after the AMP(s) dissolve in the anionic surfactant.

A certain example of coating the AMP(s) of the present disclosure is a two-stage coating. One or more antimicrobial peptides (AMPs) is dissolved in a buffer containing a lower concentration anionic surfactant than 0.002% (w/v) to form a first solution (solution (a)). The resulting first solution is added to a buffer containing a higher concentration anionic surfactant than 0.02% (w/v) to the solution (a) to form a second solution (solution (b)). The amount of a buffer containing a high concentration anionic surfactant is equal to that of the buffer containing a low concentration anionic surfactant. Subsequently, the resulting second solution is coated onto the surface of the material so that the AMP attaches onto the surface. In one embodiment, the AMP in a buffer containing a low concentration anionic surfactant is in an amount ranging from about 0.002% (w/v) to about 0.02% (w/v). In some embodiments, the AMP in a buffer containing a high concentration anionic surfactant is in an amount ranging from 0.02% (w/v) to about 0.6% (w/v).

The AMPs are used to coat on the surface of various types of biomaterials. The coating can increase the half-life and reduce the side effect of AMPs in the body. Importantly, both the biofilm formation of bacteria on the implant and the colonization of bacteria in peri-implant tissue needs to be taken into consideration in designing prevention strategies. The AMPs may be coated on a variety of substrates, such as metals, ceramics, polymers, fibers and inert materials. Suitable metallic materials include metals, titanium-based alloys, stainless steel and nickel-chrome. Suitable polymeric materials include, but are not limited to, polystyrene (PS), polyethylene (PE), polypropylene (PP) and polyurethane (PU). These substrates may be in the form of, or form part of, films, particles (nanoparticles, micro-particles, beads), fibers (wound dressings, bandages, tape, pads, sponges), catheters, stents, contact lenses, bone implants, other surgical and dental instruments and/or medical devices used within or in contact with the body.

In one example, the AMP particles remain bound to polystyrene for at least 14 days in human urine and for 4 days in bovine serum. Both the remaining AMPs on the polystyrene/silicone and released AMPs in the urine/serum are bactericidal against *E. coli* and *Pseudomonas aeruginosa* PAO1. The coated AMPs are also inhibitory to the biofilm formation of *P. aeruginosa* 27853 in human urine.

Without further elaboration, it is believed that one skilled in the art can, based on the disclosure herein, utilize the present disclosure to its fullest extent. The following specific examples are, therefore, to be construed as merely descriptive, and not limiting of the remainder of the disclosure in any way whatsoever.

EXAMPLES

Materials and Methods

Coating Materials

The surfactants, sodium dodecyl sulfate (SDS) and sodium dodecylbenzenesulfonate (SDBS) were purchased from Bio-Rad (Hercules, CA, USA) and Sigma-Aldrich (St. Louis, Missouri, USA), respectively. Sodium octyl sulfate (SOS) and sodium 1-decane sulfonate (SDSn) were purchased from Sigma-Aldrich (St. Louis, Missouri, USA). Non-tissue culture polystyrene-based 96-well microplates were obtained from Corning Inc. (NY, USA). Silicone was obtained from Momentive Company (Tokyo, Japan). Polyurethane (PU) was kindly provided by Pacific Hospital Supply Co. (Taipei, Taiwan). Titanium was a kind gift of Dr. Si-Ron Chen from China Steel Corporation (Kaohsiung, Taiwan).

The amino acid sequences of antimicrobial peptides (AMPs) including RR12, RRIKA, SAAP159, SMAP29, SMAP28-3+2, T9W, T18,19K and TP4-A12,15I are shown in Table 51. They were synthesized by Kelowna International Scientific Inc. (Taipei, Taiwan) with 95% purity and their molecular masses were verified by mass spectrometry analysis.

TABLE S1

Amino acid sequence of antimicrobial peptides. (The first table below discloses SEQ ID NOS 1, 24, 3, 2, 25, 6-7, 10-15, 26, 18-20, 22-23, 21, 3, and 21 and the second table below discloses SEQ ID NOS 14-16, 18, 20, 23, 3, and 21, all respectively, in order of appearance).

| Antimicrobial peptide | Sequence [ref.] |
|---|---|
| L-BMAP27 | GRFKRFRKKFKKLFKKLSPVIPLLHLG-OH |
| D-BMAP27 | GRFKRFRKKFKKLFKKLSPVIPLLHLG-OH (All in D form) |
| CAME-T18K, T19K | KWKLFKKIGIGAVLKVLKKG-NH$_2$ |
| CAME-A12K, K15H | KWKLFKKIGIGKVLHVLTTG-NH$_2$ |
| CAP18 | GLRKRLRKFRNKIKEKIKKIGQKIQGLLPKLAPRTDY-OH |

TABLE S1-continued

Amino acid sequence of antimicrobial peptides. (The first table below discloses SEQ ID NOS 1, 24, 3, 2, 25, 6-7, 10-15, 26, 18-20, 22-23, 21, 3, and 21 and the second table below discloses SEQ ID NOS 14-16, 18, 20, 23, 3, and 21, all respectively, in order of appearance).

| | |
|---|---|
| Epinecidin-1 | GFIFHIIKGLFHAGKMIHGLV-OH |
| GW-Q6 | GIKIAKKAITIAKKIAKIYW-OH |
| NLF20 | H-NLFRKLTHRLFRRNFGYTLR-OH |
| NRC12 | H-GWKKWFNRAKKVGKTVGGLAVDHYL-NH$_2$ |
| Pilosulin-1 | GLGSVFGRLARILGRVIPKV-NH$_2$ |
| Pleurocidin | GWGSFFKKAAHVGKHVGKAALTHYL-NH$_2$ |
| RR12 | H-RRLIRLILRLLR-NH$_2$ |
| RRIKA | H-WLRRIKAWLRRIKA-OH |
| SAAP159 | LKRLYKRVFRLLKRYYGQLRRPVR-OH |
| SMAP29 | RGLRRLGRKIAHGVKKYGPTVLRIIRIAG-NH$_2$ |
| SMAP28-3 | RGLRRLGRKIVHVVKKYLPTVLRIIRIA-NH$_2$ |
| SMAP28-3 + 2 | RGLRRLGRKIVHVVKKYLPTVLRIIRRL-NH$_2$ |
| T9F | RFRRLRKKFRKRLKKI-NH$_2$ |
| T9W | RFRRLRKKWRKRLKKI-NH$_2$ |
| TP4(Piscidins 4) | H-FIHHIIGGLFSAGKAIHRLIRRRRR-OH |
| T18, 19K | KWKLFKKIGIGAVLKVLKKG-NH$_2$ |
| TP4-A12, 15I | H-FIHHIIGGLFSAGKAIHRLIRRRRR-OH |

| Antimicrobial peptide | Sequence |
|---|---|
| RR12 | H-RRLIRLILRLLR-NH$_2$ |
| RRIKA | H-WLRRIKAWLRRIKA-OH |
| SAAP159 | LKRLYKRVFRLLKRYYRQLRRPVR-OH |
| SMAP29 | RGLRRLGRKIAHGVKKYGPTVLRIIRIAG-NH$_2$ |
| SMAP2S-3 + 2 | RGLRRLGRKIVHVVKKYLPTVLRIIRRL-NH$_2$ |
| T9W | RFRRLRKKWRKRLKKI-NH$_2$ |
| T18, 19K | KWKLFKKIGIGAVLKVLKKG-NH$_2$ |
| TP4-A12, 15I | H-FIHHIIGGLFSAGKAIHRLIRRRRR-OH |

Non-tissue culture polystyrene-based 96-well microplate was obtained from Corning Inc. (NY, USA). Cover glass (circles, 5×0.125 mm) was obtained from Assistant Company (Sondheim, Germany). Silicone was obtained from Momentive Company (Tokyo, Japan). Aluminum, stainless steel #301, latex (6×1 mm) and polypropylene carbonate (PPC, 6×1 mm) were kindly provided by Shineteh Instruments Co. (Taipei, Taiwan). Polyvinyl chloride (PVC) and polyurethane (PU) were kindly provided by Pacific Hospital Supply Co. (Taipei, Taiwan). Titanium was a kind gift of Dr. Si-Ron Chen from China Steel Corporation (Kaohsiung, Taiwan).

Coating of AMPs onto Biomaterial Discs

All of the biomaterials were shaped into round discs by a hole-puncher with diameter of 6.0 mm and placed into 96-well polystyrene-based microplates for coating. The antimicrobials including AMPs and antibiotics were dissolved in sodium phosphate buffer (10 mM, pH 7.4) containing various concentrations of surfactant and loaded into the respective wells of the biomaterial disc-containing 96-well microplates. 1× surfactant (1×SDS or SDBS) was defined as 0.075% surfactant (w/v) dissolved in phosphate buffer (10 mM sodium phosphate, pH 7.4). Various coating methods were performed and named as described below.

First, 1-step method: 8 or 24 µg antimicrobials were dissolved in 60 µl surfactant (at the indicated concentrations). The antimicrobials were loaded into respective wells of the disc-containing microplates and kept overnight for coating. The solution was then removed from the microplates and the dried microplates were kept at room temperature until use.

Second, 2-step method: 8 or 24 µg antimicrobials were dissolved in 30 µl surfactant (at low concentrations as indicated) and loaded into respective wells of the disc-containing microplates. Another 30 µl surfactant without antimicrobials (at higher concentrations) was added to the abovementioned antimicrobial-containing solution and kept overnight for coating. The solution was then removed from the microplates and the dried microplates were kept at room temperature until use.

Third, PXB-AMP mix-coating method: The PXB-AMP mixtures (16 μg, 8 μg each) were dissolved in 30 μl surfactant at lower concentration as indicated. Another 30 μl surfactant without antimicrobials (at higher concentrations) was added and loaded onto the discs that were placed in the microplates as mentioned above.

Stability of Coated AMPs Examined by Microscopy and SDS-PAGE

The stability of coated antimicrobials on the microplate when incubated in human urine, or 10-50% FBS, was analyzed at different time intervals under Nikon TMS-F inverted phase contrast microscope (Tokyo, Japan) equipped with TrueChrome IIs camera (Tucsen, China) and by 15% SDS-PAGE after dissolving the coatings in the SDS loading buffer (2% SDS, 10% glycerol, 5% 2-mercaptoethanol, 0.01% bromophenol blue, 125 mM Tris-HCl, pH6.8). The thermal stability of AMPs coated on microplate by SDS/SDBS against 37° C. and 60° C. treatment for 4 weeks was examined by microscopy and SDS-PAGE analysis after a seven-day urine incubation. The stability of AMPs coated on microplate by SDS against ethylene oxide sterilization (500 ppm) at 55° C. for 6 hr was examined by SDS-PAGE analysis. With respect to non-transparent biomaterials, such as silicone, polyurethane and titanium, only SDS-PAGE analysis was performed.

Morphology and Stability of Coated Antimicrobials Examined by Microscopy and SDS-PAGE The morphology and stability of coated antimicrobials in human urine or 10% fetal bovine serum (FBS) was analyzed at different time intervals by both microscopic observation using Nikon TMS-F inverted phase contrast microscope (Tokyo, Japan) equipped with TrueChrome IIs camera (Tucsen, China), as well as by 15% reduced SDS-PAGE after dissolving the antimicrobials in loading buffer (2% SDS, 10% glycerol, 5% 2-mercaptoethanol, 0.01% bromophenol blue, 125 mM Tris-HCl, pH6.8). The stabilities of antimicrobials coated onto other substrates, such as silicone and titanium, in urine or serum were analyzed by 15% reduced SDS-PAGE only.

Antimicrobial Activities of Free and Coated AMPs

Bacteria. *Pseudomonas aeruginosa* PAO1 (ATCC BAA-47™), *E. coli* K-12 (MG1655), and *E. coli* (ATCC 23502) obtained from human clinics were cultured in/on Difco™ LB broth/agar (BD, New Jersey, USA). *Staphylococcus aureus* (ATCC 6538) were cultured in/on Difco™ TSB broth/agar.

Inhibition zone. Bacteria were cultured in Luria-Bertani broth and plated on Luria-Bertani agar for *E. coli* (ATCC 23502) and *Pseudomonas aeruginosa* (ATCC 27853) at 37° C. *Staphylococcus aureus* (ATCC 6538P) was cultured and plated in/on tryptic soy broth/agar. *Candida albicans* (ATCC 14053) were cultured in/on YM broth/agar at 30° C. Five ml of low melting agar (1%) mixed with 100 μl of overnight-cultured bacteria was spread on top of 1% regular agar plate. Two μl of antimicrobial peptides at various concentrations were dotted on the top layer of microbe-containing agar plates and incubated overnight for the development of inhibition zone.

Bactericidal activity of coated antimicrobials. Antimicrobials coated on the surface of polystyrene or silicone discs placed into wells of 96-well microplates were incubated in 100 μl of sterile human urine using the protocol approved by AS-IRB01-16070, or in 10% fetal bovine serum (FBS in RPMI1640), for the indicated times. The urine and serum were changed daily. 100 μl of microbes such as *E. coli* K-12 ($1.5 \times 10^6$ cfu/ml), *P. aeruginosa* PAOI and *S. aureus* ($3 \times 10^6$ cfu/ml) was inoculated onto the drained discs/microplates and incubated at 37° C. for 1.5 hrs. After plating onto the respective agar plates, colony forming units (cfu) were determined.

Bactericidal activity of released antimicrobials. The discs/microplates which had been coated with antimicrobials were incubated in 160 μl of sterile human urine, or in 10% FBS. The urine and serum were changed daily. 50 μl of the daily changed urine or serum was mixed with 50 μl of suspension containing *E. coli* K-12 ($3 \times 10^5$ cfu/ml) or *P. aeruginosa* PAOI ($1.5 \times 10^5$ cfu/ml), and incubated at 37° C. for 1.5 hrs. After plating onto the respective agar plates, colony forming units (cfu) were determined.

Minimum inhibitory concentration (MIC) and minimum bactericidal concentration (MBC). For the determination of antimicrobial potency of free AMPs, the two-fold serially diluted AMPs (10 μl) were mixed with 90 μl of bacterial suspension ($3 \times 10^5$ cfu/ml) in respective medium (LB or TSB). The suspended AMPs were then loaded into wells of 96-well microplates and incubated at 37° C. overnight with gentle agitation at 100 rpm. The absorbance was measured by SpectraMax 190 microplate reader at 600 nm. The remaining cfu in the mixture was counted after plating on agar plate. Minimum inhibitory concentration (MIC) was defined as the lowest AMP concentration to keep the solution with the same absorbance as that of culture medium without bacteria. Minimum bactericidal concentration (MBC) was defined as the lowest AMP concentration which is able to kill 99.99% of inoculated microorganisms (24). Alternatively, the MIC of coated AMPs was also determined. In brief, the AMP-coated silicone discs were either immersed in 200 μl sterile human urine, or in cell culture medium (RPMI 1640+10% FBS) overnight. 190 μl of the released AMP/surfactant after two-fold serial dilution were mixed with 10 μl *E. coli* ATCC 23502 at the final concentration $3 \times 10^5$ cfu/ml in 96-well microplates and incubated and determined for remaining cfu as mentioned above. The free form AMPs as well as surfactant were dissolved in 200 μl sterile media (cell culture medium or human urine) and used as a control for quantitation. The potency of antimicrobial activity was expressed as the dilution folds to reach the MIC, in which no bacteria grow in the medium. At least three independent experiments were performed to determine the value.

Quantitation of Released Antimicrobials by Inhibition Zone and the Minimal Inhibitory Concentration Method The antimicrobial-immobilized silicone discs or microplates were incubated in 100 μl of human urine or in 200 μl of 10% FBS. The urine and serum were changed daily. Two μl of the incubation urine or serum being replaced (containing released/free SAAP159+PXB) or its dilutions were dotted onto the top layer of the microbe-containing agar plates and incubated at 37° C. overnight, following which the assessment of formation of growth inhibition zone was carried out. Defined amounts of mixed antimicrobials were used as a standard for the quantitation of the released antimicrobials. The amount of antimicrobial mixture which was able to form visible inhibition zone on the agar plate is defined as one unit of antimicrobial activity. For example, 5 ng PXB+2.5 ng AMP (SAAP159) in urine, and 2.5 ng PXB+1.25 ng SAAP159 in serum, respectively. Alternatively, to carry out the minimal inhibitory concentration (MIC) method, 190 μl of free antimicrobials or those that released in the serum or urine (200 μl) was mixed with 10

µl of microbes (1-30×10⁵ cfu/ml) in the respective wells of a 96-well microplate and incubated overnight with gentle agitation at 100 rpm. The absorbance at 600 nm was then determined by SpectraMax 190 microplate reader. Minimal inhibitory concentration (MIC), which is defined as the concentration of (diluted) sample serum or urine which is able to keep the absorbance of the bacteria-containing media no different to that of media only, was determined. The potency of antimicrobial activity, which is defined as the dilution fold of antimicrobial-containing urine or serum that achieves MIC, was also determined.

Antimicrobial Activity of Coated AMPs 96-well microplates which had been coated with AMPs or adapted with AMP-coated silicone discs were immersed in 100 µl sterile human urine using the protocol approved by AS-IRB01-16070, or in 10% FBS dissolved in RPMI1640, with daily changes. One hundred µl of $E.\ coli$ ATCC 23502 ($2\times10^5$ cfu/ml) was inoculated onto the drained discs/microplates and incubated at 37° C. for three hours before plating on the agar plates.

Bacterial Adherence

Both sides of silicone discs were coated by paired AMPs by 2-step SDS or SDBS coating method. These discs after incubation with urine were immersed in 270 µl of $P.\ aeruginosa$ 27853 ($2\times10^7$ cfu/ml) in 96-well microplate and incubated at 37° C. for three hours with gentle shaking at 150 rpm for bacterial adherence. The bacteria-anchored discs were washed by 700 µl of PBS three times, and then sonicated for two min to disperse the bacteria from the discs. The bacteria in the solution were counted after plating on agar plate. Silicones disc without AMP coating acted as a control. At least three independent experiments with three discs in each experiment were performed to determine the average value.

Hemolytic Assay

Fresh mouse blood was collected following the protocol approved by IACUC Academia $Sinica$ (AS-IUCUC-19-01-1277). The blood cells were pelleted and rinsed three times with 10% FBS in RPMI1640, and re-suspended in the same buffer. The erythrocytes ($1.5\times10^7$ cells) were then added to the solution containing free dual AMP/surfactant or overnight released components from silicone discs in 200 µl and incubation at 37° C. for one hr. The supernatants (150 µl) after centrifugation were transferred to 96-well plate for the measurement of the absorbance of released hemoglobin by SpectraMax 190 microplate reader (Molecular Devices, CA, USA) at 414 nm. Percent hemolysis was calculated using the following formula: % hemolysis=[(A414$_{sample}$−A414$_{medium}$)/(A414$_{0.1\%\ Triton-X\ 100}$−A414$_{medium}$)]. Zero and 100% hemolysis were determined in medium and 0.1% Triton-X 100, respectively.

Cytotoxicity Assay

Human bladder carcinoma cell line (NTUB1) was kindly provided by Dr. Te-Chang Lee (Institute of Biomedical Sciences, Academia Sinica, Taipei, Taiwan). Fetal bovine serum (FBS) and RPMI1640 were purchased from ThermoFisher Scientific Inc (Waltham, Massachusetts, USA). NTUB1 cells were maintained at 37° C. in a humidified incubator under 5% $CO_2$ atmosphere in RPMI1640 containing 10% FBS, 100 U/ml penicillin and 100 µg/ml streptomycin. The NTUB1 cells were seeded in the respective wells of a 96-well plate at a density of $1.5\times10^4$ cells/1000 for 24 hr. The cells were further incubated in 2000 free antimicrobial/surfactant or components released from silicone disc after overnight incubation. After 20 hr incubation, 900 of fresh culture medium and 100 of WST-1 agent (Roche, Basel, Switzerland) were added to the drained wells and incubated for two 2 hr before measuring the absorbance by SpectraMax 190 microplate reader at 450 nm. Percent of cytotoxicity was determined using the following formula: % cytotoxicity=[(A450$_{sample}$−A450$_{positive\ control}$)/(A450$_{negative\ control}$−A450$_{positive\ control}$)]. Positive control was NTUB1 cells only, whereas negative control was medium without cells.

Mouse Model

Coating silicone tubing Silicone tubing with specifications of 0.3 mm (inner diameter [i.d.]) by 0.64 mm (outer diameter [o.d.]) was procured, and 4 mm segments of this tubing were used as implants in a mouse model. The coating of silicone tubing with paired AMPs was prepared by the two-step method, then cut into four mm segments before use. The needle portion of the I.V. catheter was temporarily removed from the catheter, and a four mm section from the tip of the catheter was cut off using sterile blades. Four mm segments of coated or non-coated silicone tubing were then assembled onto the original needle.

Implantation of silicone tubing in mouse bladder Eight to 10 weeks old ICR female mice were anesthetized with Zoletil® containing Tiletamine and Zolazepam (VIRVAC, France) using the protocol approved by Academia $Sinica$ (AS-IUCUC-19-01-1277). The modified 24G catheter, mounted on the original needle, was positioned at a 30-degree angle immediately above the pubic bone with the bevel directed to the anterior. When the needle was carefully inserted into the bladder, the needle was removed while the 'pusher' was pushed slightly inward. This dislodged the short catheter segment into the lumen of the bladder, such that once the 'pusher' was removed, the only thing that remained inside the mouse bladder was the implanted four mm silicone tubing. After catheter implantation, 100 µl of $E.\ coli$ 23502 ($5\times10^9$ cfu/ml) or $P.\ aeruginosa$ 27853 ($3\times10^9$ cfu/ml) was injected into the bladder lumen. Urine was collected every two days using metabolic cage and quantified for the number of viable bacteria. Mice were sacrificed on day eight post-instillation. Indwelling tubing was collected, rinsed with 200 µl of sterile PBS and immersed in 200 µl of fresh PBS prior to sonication at 50/60 Hz for 10 min in an ultrasonic water bath for biofilm dispersal. The bacterial numbers were determined after serial dilutions and plating on agar plate. In addition, bacterial colonization in the urinary bladder was also measured after homogenization in 500 µl of PBS.

Statistical Analysis

For all in vitro antimicrobial assays, the average value with standard error was determined from at least three independent experiments. For determination of bacterial growth in urine and bacterial adherence to bladder and silicone tubing in the mouse model, a series of Wilcoxon rank sum tests were performed for pairwise comparisons to determine the significance of the difference found in the measured values between control non-coated tubing and experimental antimicrobial-coated tubing. $P<0.05$ was considered to be statistically significant.

Example 1 Coating of Antimicrobial Peptides by Anionic Surfactants

The antimicrobial peptide SMAP29 readily dissolves in aqueous solution, however if anionic surfactant, such as sarkosyl or SDS, was added, they become aggregated giving a cloudy solution appearance (data not shown). This is also shown in an SDS PAGE, where SMAP29 peptides at the indicated concentrations (8 µg, 24 µg/60 µl) were pulled down to the bottom of tube after centrifugation in the presence of 0.075% (w/v) sarkosyl or SDS, designated as 1× Sar or 1×SDS, respectively, or at lower surfactant concentrations (FIG. 1A-B). The AMP TP4 was also pulled down in analogous anionic surfactant, SDBS, at a broader concentration ranging from 1/64× to 16×SDBS (FIG. 1C).

Figure 2A:
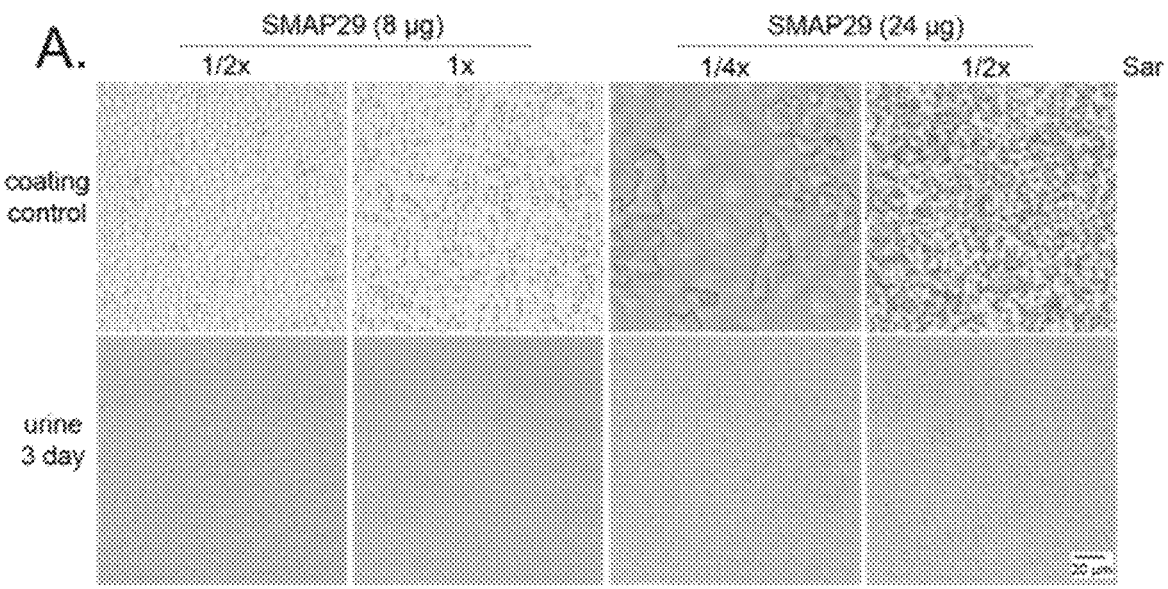
FIG. 2. Morphology of antimicrobial peptides in various surfactants and their stability in urine. (A-D) The morphologies of SMAP29 vesicles (8 µg or 24 µg/600) induced by sarkosyl (A) and SDS (C) were examined under microscopy after 3-day urine treatment. Their stabilities in urine were determined by 15% SDS-PAGE. The morphology and stability of TP4 vesicles (24 µg/600) induced by SDSn, SOS and SDBS in urine was examined by microscopy (E) and SDS-PAGE (F). The SDSn, SOS and SDBS represent surfactants sodium 1-decane sulfonate, sodium octyl sulfate and sodium dodecylbenzenesulfonate, respectively. 4 µg SMAP29 or TP4 peptides and their equivalents were taken for SDS-PAGE analysis.
Figure 2B:
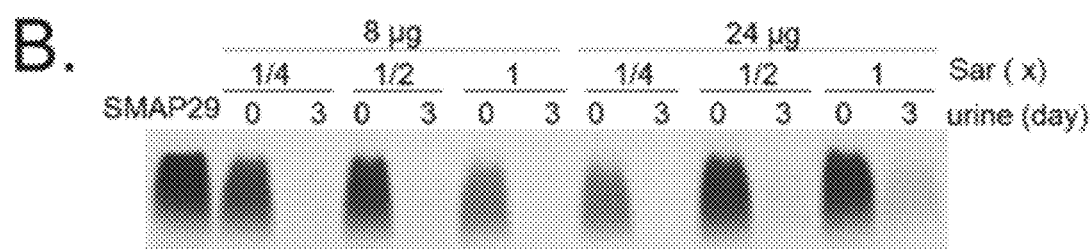
Figure 2C:
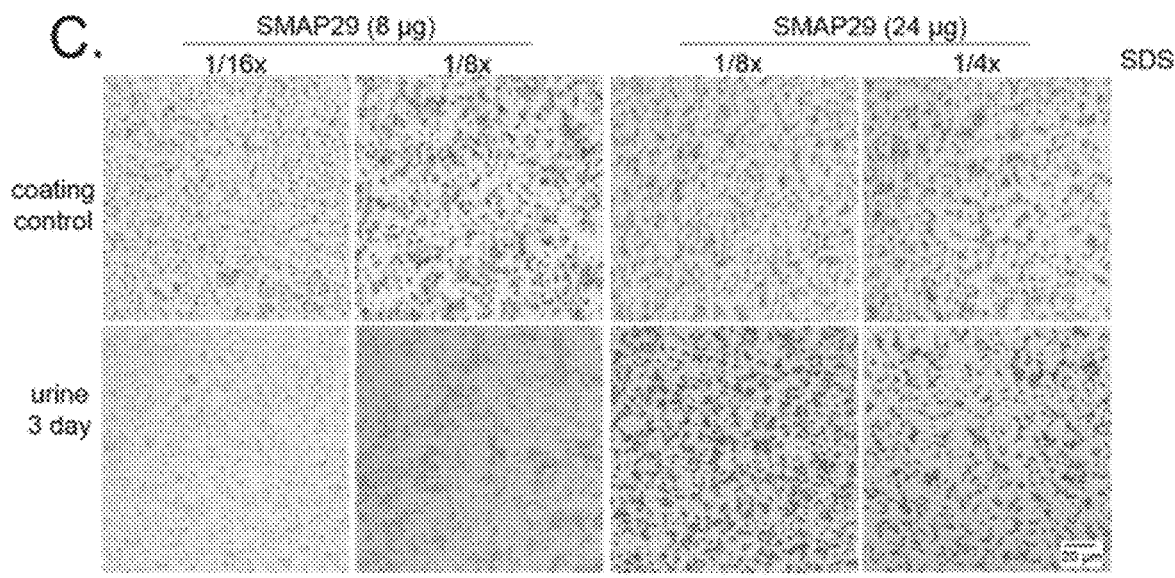
Figure 2D:
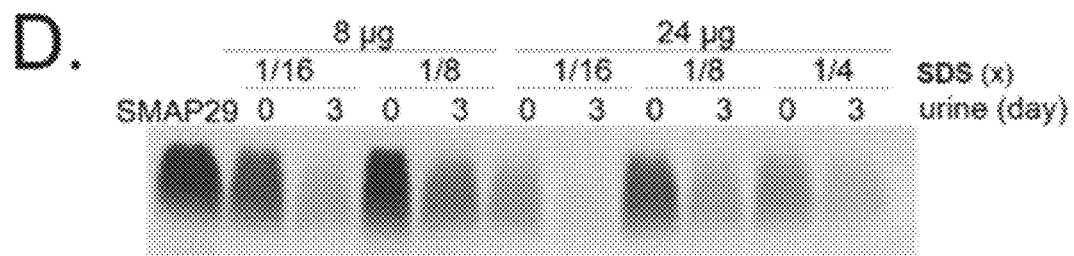
Figure 2E:
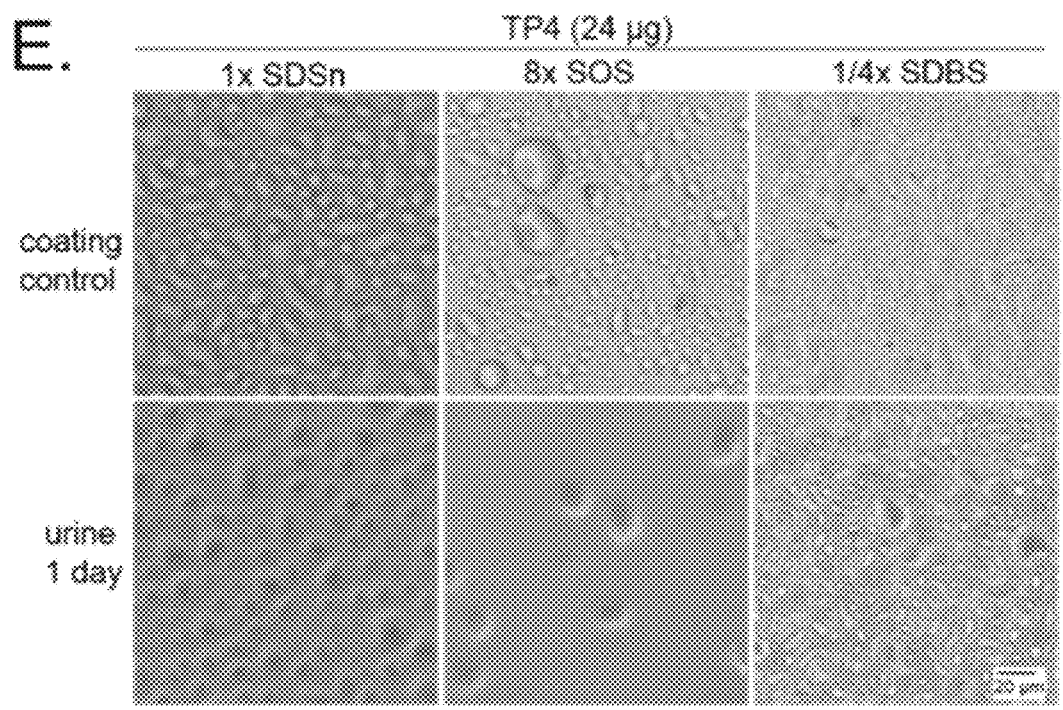
Figure 2F:
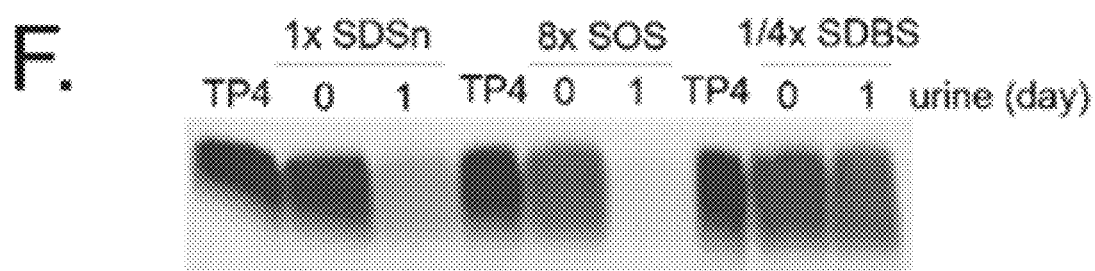
Figure 3:
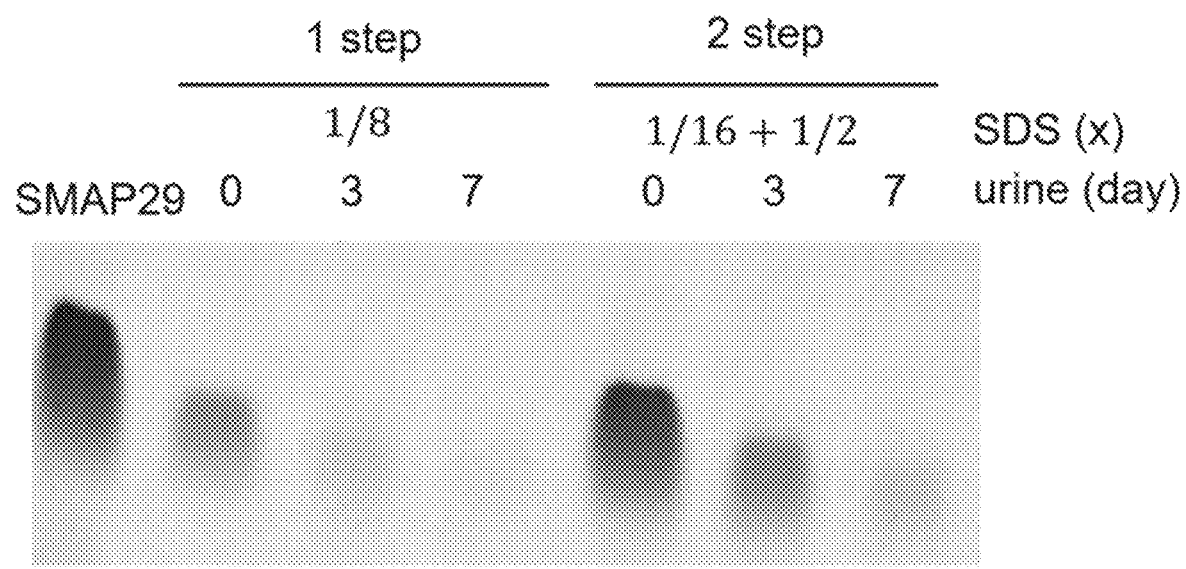
FIG. 3. Coating efficiency and urine stabilities of SMAP29 peptides coated by one step and two-step coating methods. SMAP29 peptides (24 µg) were coated on 96-well microplates by one-step and two-step coating method, respectively. The respective peptides coated and remaining on the microplates after 3-day and 7-day urine treatments were subjected to 15% SDS-PAGE. 4 µg SMAP29 peptides and their equivalents after urine treatment were taken for analysis.
Figure 4:
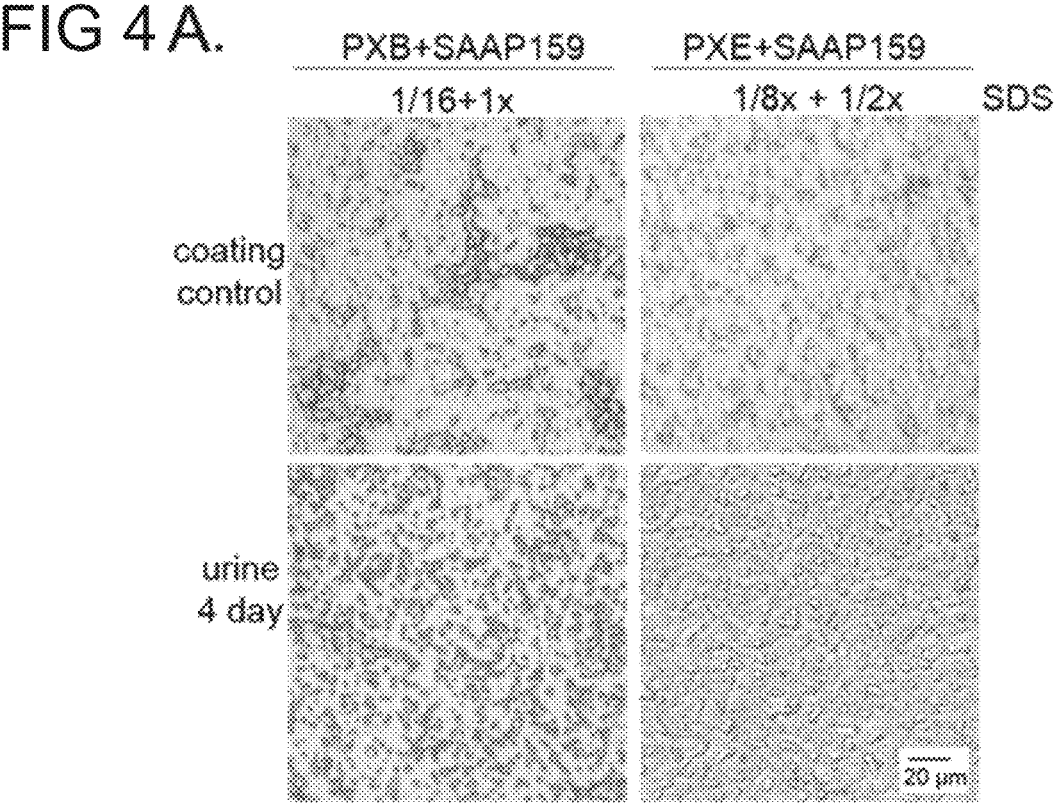
FIG. 4. Morphology of AMP-antibiotic mix-coated vesicles induced by SDS and stability in urine. (A-B) Morphology of SAAP159-PXB and SAAP159-PXE vesicles were examined under microscope and their stability in urine were determined by 15% SDS-PAGE. (C) Stability of coated SAAP159-PXB pair and SAAP159 alone were determined by SDS-PAGE. The PXB, PXE (16 µg each) was mix-coated with SAAP159 (8 µg) on the microplates by 2-step SDS coating method. SAAP159 alone (either 24 µg or 8 µg) was coated as a control. (D) Stability of Gentamicin mix-coated with AMPs (T9W, SMAP29 and SAAP159) and their stabilities in urine for 2 days analyzed by SDS-PAGE. PXB and PXE represent Polymyxin B and Polymyxin E, respectively.
Figure 4:
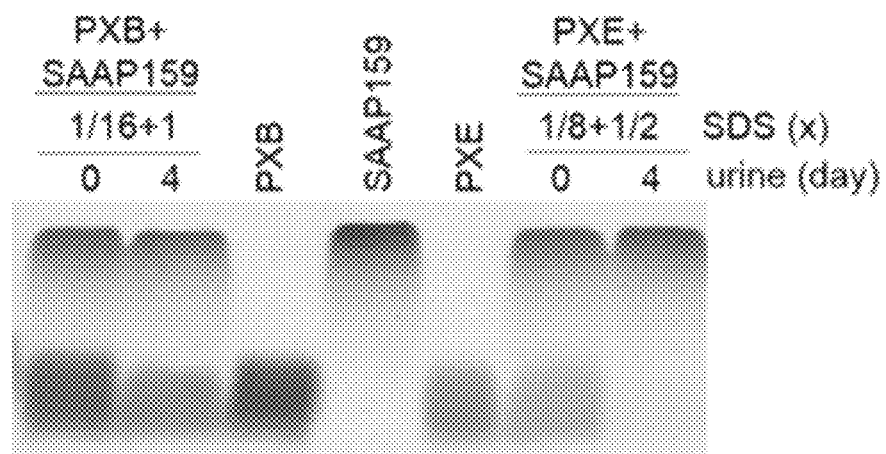
Figure 4:
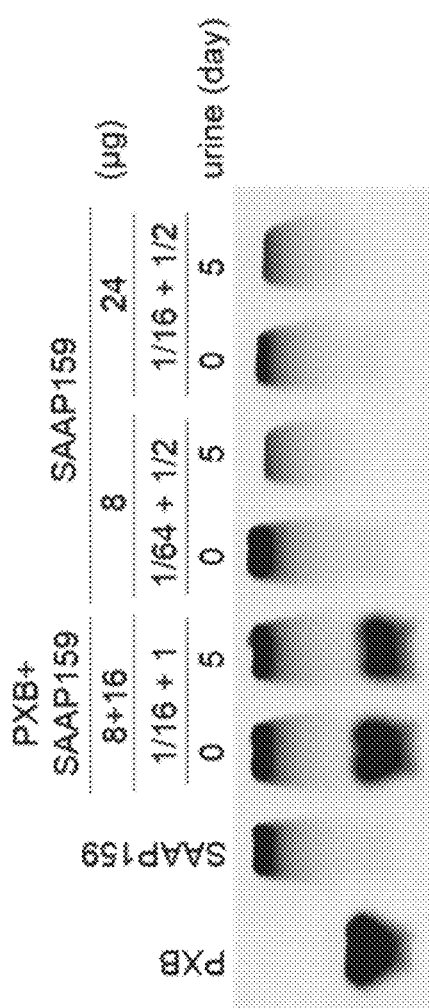
Figure 5A:
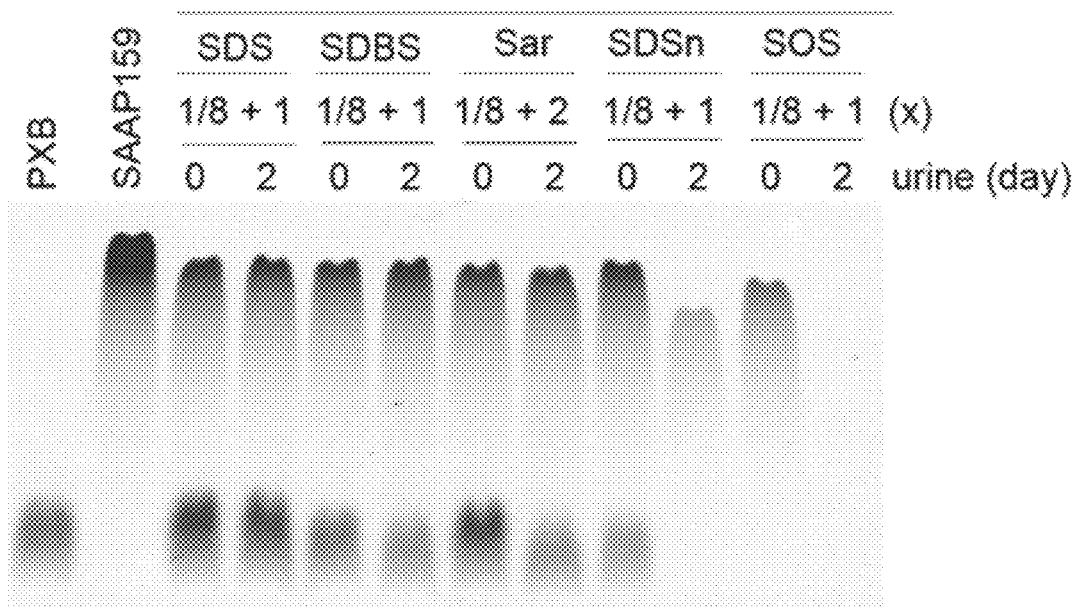
FIG. 5. Coating efficiency of PXB with SAAP159 (A) and TP4 (B) by various surfactants (sarkosyl, SDS, SDBS, SDSn and SOS) and their stabilities in urine. 4 µg AMP and its equivalents were taken for SDS-PAGE analysis. SDS, sodium dodecyl sulfate; SDBS, sodium dodecylbenzenesulfonate; Sar, sarkosyl; SDSn, sodium 1-decane sulfonate; SOS, sodium octyl sulfate.
Figure 5B:
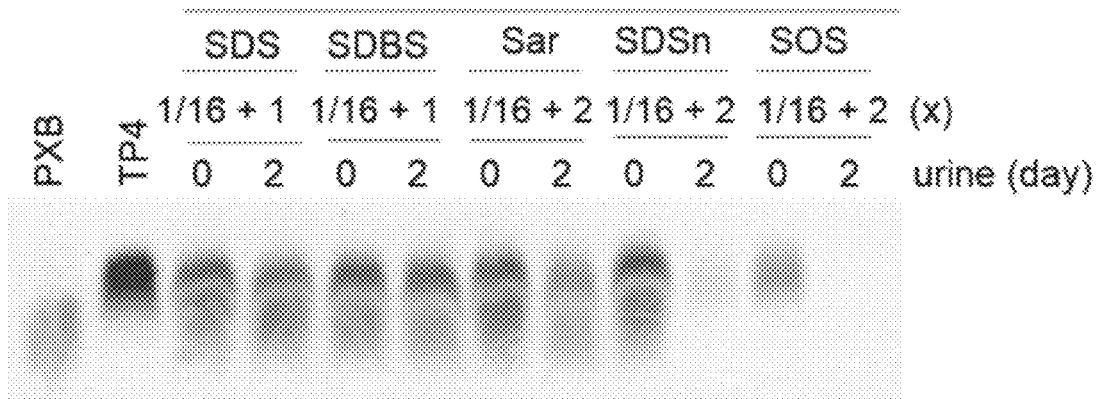
Figure 6A:
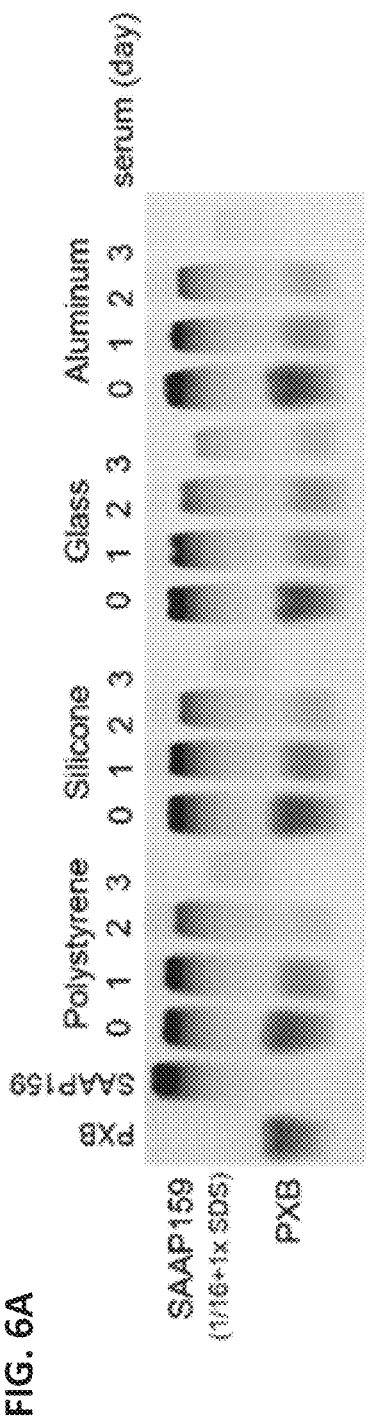
FIG. 6. Coating efficiency of PXB-AMP pairs on various biomaterials and their stabilities in serum. (A) The PXB-SAAP159 pairs were coated on the cover glass, and discs of silicone and aluminum which were adapted in the 96-well microplates as well as the polystyrene-based microplate. (B) The PXB-SAAP159 pairs were also coated on the discs of polyvinyl chloride (PVC), polypropylene carbonate (PPC), latex, stainless steel, titanium and polyurethane (PU). Their stabilities in serum were analyzed by SDS-PAGE. 4 µg AMP and its equivalents were taken for SDS-PAGE analysis.
Figure 6B:
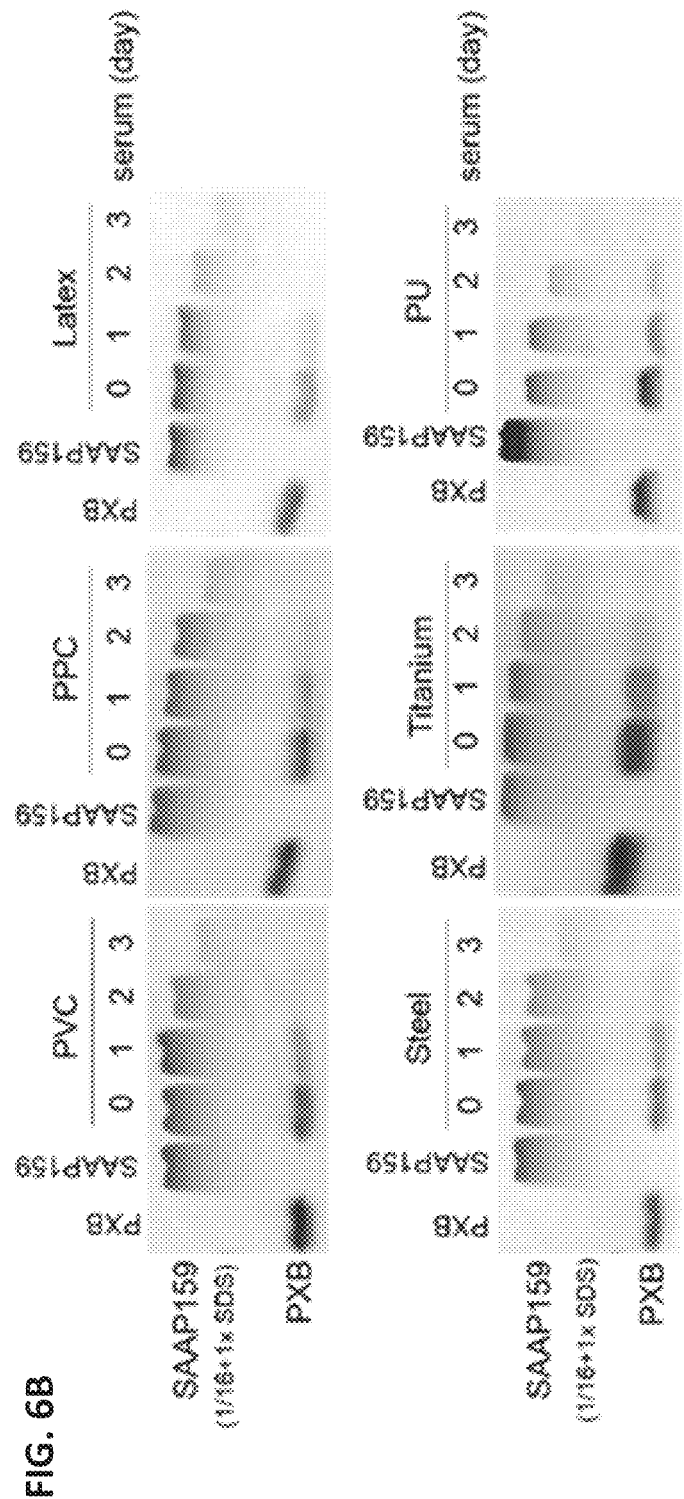

In the presence of sarkosyl or SDS at the indicated concentrations, the SMAP29 peptides formed small vesicle-like structures ("vesicles") with diameters ranging from 1-10 µm on the polystyrene-based 96-well microplates (FIG. 2A,C, top panel). To determine whether these AMP vesicles are stable in bodily fluids, their morphologies were examined first under light microscopy, and then analyzed by SDS-PAGE after a three-day incubation period in urine (with daily changes of fresh urine). The SMAP29 vesicles that were coated by SDS remained on the microplates after the three-day incubation period. However, those coated by sarkosyl disappeared although they had similar coating efficiency (FIG. 2B,D). The TP4 peptides were also effectively coated on the microplates by other anionic surfactants, namely SDBS, SOS and SDSn, at the respective indicated concentrations. Only TP4 peptides that were coated by SDBS, but not those coated by SOS or SDSn, were stable in urine after a one-day incubation period (FIG. 2E-F).

Example 2 Types of Antimicrobials that can be Coated onto Biomaterials by SDS The SMAP-29-derived peptides (SMAP-28-3, SMAP28-3+2), SAAP159, TP4, and the L- and D-forms of BMAP27 (designated as L-BMAP27 and D-BMAP27, respectively) were found to be successfully coated onto the microplate by SDS and remained stable in human urine for at least three days as examined under the microscope. However, T9W and lipopeptide antibiotics such as Polymyxin B (PXB) aggregated immediately after the addition of surfactants including SDS, but they were unable to be evenly dispersed and coated on the substrate by the tested SDS concentrations (1/16×-32×).

Example 3 Coating of AMPs in Combination with Antibiotics

Improvement of coating efficiency by two-step coating method Because some AMPs aggregated after the addition of surfactants at high peptide concentrations and could not evenly and firmly attach to the microplate, we developed a two-step coating protocol to circumvent the problem. The result show that the coating efficiency and urine stability of SMAP29 peptides at day 3 and 7 by one-step coating method (24 μg in ⅛×SDS buffer) are much lower than that of two-step coating method (24 μg in first 1/16×SDS buffer, then mixed with second ½×SDS buffer) (FIG. 3).

AMP with other antibiotics To increase the antimicrobial efficacy and to broaden the antimicrobial spectrum of coated antimicrobials, AMPs in combination with antibiotics were simultaneously coated onto the same substrate. The SAAP159 in combination with Polymyxin B (PXB) or Polymyxin E (PXE) were coated onto the microplate by the 2-step SDS coating method. The vesicles exerted by PXB-SAAP159 and PXE-SAAP159 pairs were stable in urine for more than four days as observed under the microscope (FIG. 4A). The individual SAAP159 and PXB of the SAAP159-PXB pair were also found to be stable in urine when analyzed by SDS-PAGE. However, the PXE of PXE-SAAP159 pair was found to be released after the four-day urine treatment (FIG. 4B). Interestingly, PXB also increased the stability of SAAP159 in urine although the coating efficiency of SAAP159 alone and SAAP159-PXB mixture were similar (FIG. 4C). The aminoglycoside antibiotic, Gentamicin, in combination with any of T9W, SMAP29 and SAAP159 can also be coated onto the substrate. Unfortunately, these combinations were susceptible to urine treatment because Gentamicin was released into urine after two-days' incubation (FIG. 4D).

PXB with other AMPs In addition to the above mentioned mix-coated PXB-AMP pairs, the following AMPs, including RR12, NRC12, Pleurocidin, Epinecidin-1, Pilosulin-1, TP4, GW-Q6 and RRIKA, were also successfully coated in combination with PXB onto the substrate at the indicated SDS concentrations. Moreover, SDS-PAGE shows they were stable in urine for 7 to 14 days and in serum for 2 to 3 days.

Other surfactants In addition to SDS, the following surfactants, including SDBS, sarkosyl, SDSn and SOS, when used to dissolve the antimicrobials were also able to successfully coat the PXB+SAAP159 and PXB+TP4 pairs onto the microplate. But only those coated using SDBS and sarkosyl as well as SDS remained stable in urine for two days, whereas those coated using SDSn and SOS were not stable under the same conditions (FIG. 5A-B).

Other biomaterials In addition to polystyrene, the PXB-SAAP159 pair could also be successfully coated onto silicone, glass and aluminum discs. These antimicrobials also remained stable in serum for two to three days as shown in FIG. 6A. Furthermore, the PXB-SAAP159 pair was also successfully coated onto the discs of polyvinyl chloride (PVC), polypropylene carbonate (PPC), latex, stainless steel, titanium, and polyurethane (PU), and remained stable in 10% serum for two to three days (FIG. 6B). Because silicone is widely used in medical devices, including central venous catheter and urinary catheter, the coating efficiency of PXB in combination with AMPs (CAME-T18K,T19K, CAME-A12K,K15H, T9W, T9F, RRIKA, NLF20 and CAP18) on silicone and their stability in serum/urine were examined by SDS-PAGE. Titanium or titanium alloy is also generally employed in prosthetic devices. Therefore, AMPs (CAME-T18K,T19K, CAME-A12K,K15H, T9W, T9F, RRIKA, SMAP29, CAP18 and SAAP159) were also coated in combination with PXB on titanium discs and remained stable in serum for three to four days.

Thermo-stability To monitor the potential damages of coated PXB-AMP that may be attributed to the sterilization process of medical devices by ethylene oxide, or that which may occur during the transportation of microplates, the stability of PXB-SAAP159 coated on the microplates were examined following a 60° C. overnight incubation. No significant change was seen on the stability of the antimicrobials in water and in urine for at least 14 days and in serum for at least three days. Furthermore, after a four-weeks incubation at 60° C., PXB-SAAP159 was also found to remain stable in urine for at least seven days.

Example 4 Bactericidal Activities of AMP-PXB Pairs Coated on Polystyrene and Silicone The 13 AMP-PXB pairs coated on polystyrene microplates possessed full bactericidal activities against *E. coli* even after a 14-day urine incubation with daily changes of fresh urine. These antimicrobials also exhibited strong bactericidal activity against *P. aeruginosa* and *S. aureus* after a three-day 10% serum incubation (Table 1). With respects to AMP-PXB pairs coated on silicone discs, four pairs out of seven pairs selected for testing possessed full bactericidal activity against *E. coli* K-12 even after a 14-day urine incubation (Table 2).

TABLE 1

Bactericidal activity of PXB + AMP coated on polystyrene

| AMPs | Surfactant SDS (x) | E. coli K-12 urine 7 day | E. coli K-12 urine 14 day | P. aeruginosa PAO1 1 day | P. aeruginosa PAO1 2 day | P. aeruginosa PAO1 3 day | S. aureus 10% serum 1 day | S. aureus 10% serum 2 day | S. aureus 10% serum 3 day |
|---|---|---|---|---|---|---|---|---|---|
| PXB + SMAP29 | 1/16 + 1/2 | 0 | 0 | 0 | 0 | 1 | 0 | 1 | 8 |
| PXB + SMAP28-3 | 1/10 + 1 | 0 | 0 | 0 | 0 | 0 | 0 | 0 | 2 |
| PXB + SMAP28-3 + 2 | 1/4 + 1/3 | 0 | 0 | 0 | 0 | 0 | 0 | 0 | 3 |
| PXB + BMAP27 | 1/10 + 1/2 | 0 | 1 | 0 | 0 | 0 | 0 | 0 | 4 |
| PXB + SAAP159 | 1/16 + 1 | 0 | 0 | 0 | 0 | 0 | 0 | 0 | 0 |
| PXB + TP4 | 1/16 + 1 | 0 | 0 | 0 | 0 | 0 | 0 | 0 | 0 |
| PXB + RR12 | 1/8 + 1 | 0 | 0 | 0 | 0 | 0 | 0 | 1 | 1 |
| PXB + NRC12 | 1/8 + 1 | 0 | 0 | 0 | 0 | 0 | 1 | 1 | 1 |
| PXB + Pleurocidin | 1/8 + 1 | 0 | 0 | 0 | 0 | 0 | 0 | 0 | 0 |
| PXB + Epinecidin-1 | 1/8 + 1 | 0 | 0 | 0 | 0 | 0 | 1 | 1 | 1 |
| PXB + Pilosulin-1 | 1/16 + 1 | 0 | 0 | 0 | 0 | 0 | 0 | 1 | 1 |
| PXB + GW-Q6 | 1/16 + 1 | 0 | 0 | 0 | 0 | 0 | 0 | 0 | 3 |
| PXB + RRIKA | 1/8 + 1 | 0 | 0 | 0 | 0 | 0 | 0 | 6 | 5 |

Values represent percentage (%) of colony forming units (cfu) remaining compared with cfu found in the positive control group (without AMP-PXB coating).

TABLE 2

Bactericidal activity of PXB + AMP coated on silicone disc against E. coli

| AMPss | Surfactant SDS (x) | E. coli K-12 urine 7 day | E. coli K-12 urine 14 day |
|---|---|---|---|
| PXB + SMAP29 | 1/16 + 1/2 | 0 | 7 |
| PXB + SMAP28-3 | 1/10 + 1 | 0 | 20 |
| PXB + SMAP28-3 + 2 | 1/4 + 1/3 | 0 | 0 |
| PXB + BMAP27 | 1/10 + 1/2 | 0 | 8 |
| PXB + SAAP159 | 1/16 + 1 | 0 | 0 |
| PXB + Pleurocidin | 1/8 + 1 | 0 | 0 |
| PXB + RRIKA | 1/8 + 1 | 0 | 0 |

Values represent percentage (%) of colony forming units (cfu) remaining compared with cfu found in the positive control group (without AMP-PXB coating).

Example 5 Bactericidal Activities of AMP-PXB Pairs Released in the Urine and Serum Urine and serum samples obtained during daily urine/serum changes from eight groups of PXB/AMP pairs (coated on polystyrene) were tested for antimicrobial activities. Antimicrobial activities were determined by calculating the survival rate of inoculated microbes seven and 14 days after inoculation and is expressed as percentage of colony forming units (cfu) remaining compared with cfu found in the positive control group (without AMP-PXB coating). The results showed that some of the coated antimicrobials can consistently release into the urine over time and exhibit bactericidal activities against E. coli for at least eight to nine days (Table 3). Furthermore, these antimicrobials can also release into 10% serum and exhibit bactericidal activities against P. aeruginosa for at least two to three days (Table 4).

TABLE 3

Bactericidal activities against E. coli of PXB + AMPs that were released from polystyrene substrate into urine*

| AMPs | E. coli K-12 day 1 | day 2 | day 3 | day 4 | day 5 | day 6 | day 7 | day 8 | day 9 |
|---|---|---|---|---|---|---|---|---|---|
| PXB + SMAP29 | 0 | 0 | 0 | 0 | 32 | 100 | 90 | 91 | 100 |
| PXB + SMAP28-3 | 0 | 0 | 0 | 0 | 0 | 0 | 0 | 0 | 22 |
| PXB + SMAP28-3 + 2 | 0 | 0 | 0 | 0 | 26 | 68 | 100 | 90 | 100 |
| PXB + SAAP159 | 0 | 0 | 0 | 0 | 0 | 0 | 0 | 0 | 0 |
| PXB + NRC12 | 0 | 0 | 0 | 0 | 0 | 0 | 0 | 0 | 0 |
| PXB + Pleurocidin | 0 | 0 | 0 | 0 | 0 | 0 | 1 | 100 | 50 |
| PXB + GW-Q6 | 0 | 0 | 0 | 0 | 0 | 0 | 0 | 0 | 0 |
| PXB + RRIKA | 0 | 0 | 0 | 0 | 0 | 0 | 0 | 0 | 12 |

Values represent percentage (%) of colony forming units (cfu) remaining compared with cfu found in the positive control group (without AMP-PXB coating).

*PXB + AMPs were coated in 96-well plate and incubated with 160 μl urine. And 50 μl from daily changed urine was used for analysis.

TABLE 4

Bactericidal activities against *P. aeruginosa* of PXB + AMPs that were released from polystyrene substrate into serum*

| AMPs | *P. aeruginosa* PAO1 | | | | |
|---|---|---|---|---|---|
| | day 1 | day 2 | day 3 | day 4 | day 5 |
| PXB + SMAP29 | 0 | 0 | 36 | 69 | 81 |
| PXB + SMAP28-3 | 0 | 0 | 0 | 77 | 78 |
| PXB + SMAP28-3 + 2 | 0 | 0 | 86 | 100 | 84 |
| PXB + SAAP159 | 0 | 0 | 0 | 88 | 93 |
| PXB + NRC12 | 0 | 0 | 0 | 61 | 92 |
| PXB + Pleurocidin | 0 | 0 | 45 | 55 | 78 |
| PXB + GW-Q6 | 0 | 0 | 26 | 69 | 92 |
| PXB + RRIKA | 0 | 0 | 0 | 60 | 74 |

Values represent percentage (%) of colony forming units (cfu) remaining compared with cfu found in the positive control group (without AMP-PXB coating).
*PXB + AMPs were coated in 96-well plate and incubated with 160 µl urine. And 50 µl from daily changed urine was used for analysis.

Figure 7B:
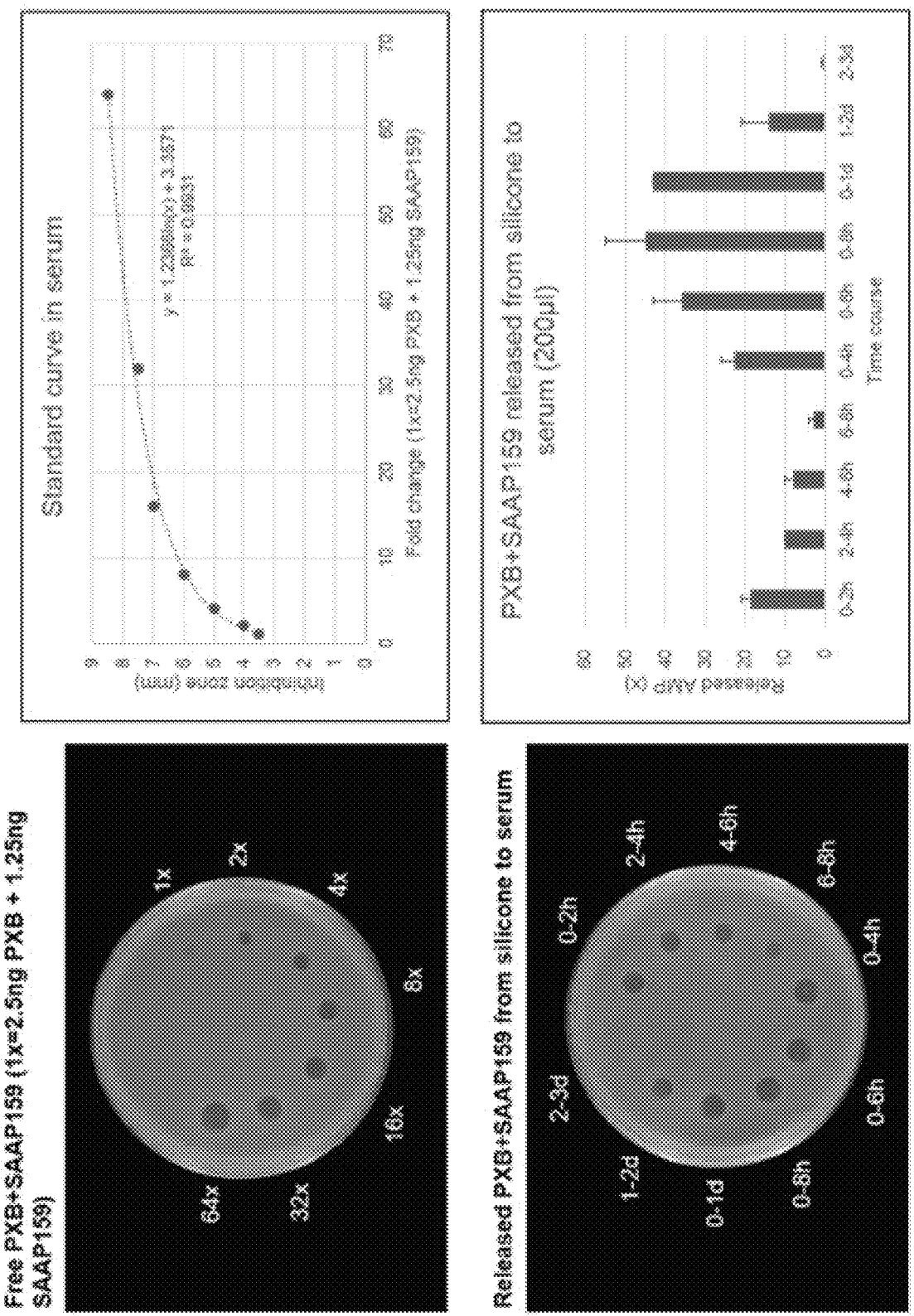
FIG. 7. Determination of antimicrobial activities of PXB-SAAP159 released from silicone discs. The serially diluted PXB+SAAP159 mixtures in urine (A) and serum (B) were dotted on LB agar plates. The diameters of inhibition zone (left, top) exerted by diluted antimicrobials (2 µl) were measured and plotted into a standard curve (right, top). The antimicrobial activity of released antimicrobials (2 µl) in urine (A) and serum (B) at different time intervals was determined by measuring the diameter of inhibition zone (bottom, left) and expressed by folds (x) (bottom, right).

Example 6 Quantitation of AMP-PXB Pairs Released into Urine and Serum by Inhibition Zone Assay The bactericidal activities of PXB/SAAP159 released from silicone discs into urine or 10% serum was semi-quantitated by measuring the diameters of the inhibition zones formed. Briefly, a 2 µl sample taken from the daily changed urine (100 µl)/serum (200 µl) was dotted onto LB agar plate containing *E. coli*. The bactericidal activity was determined by comparing the diameter of visible inhibition zones that formed as a result of the antimicrobials with known amount of PXB/SAAP159. The results demonstrate that the SAAP159/PXB pairs coated on silicone consistently released into urine for at least nine days (FIG. 7A). With respect to the release rate of antimicrobials into 10% serum, the first two-hour interval or the first day is the highest, then gradually decreased in the next time intervals (per 2 hr or day) (FIG. 7B). In the meanwhile, the antimicrobials were shown to release and accumulate in the serum for the first eight hours. It is concluded that the coated SAAP159/PXB consistently released into urine for night days and into serum for two days.

Figure 8A:
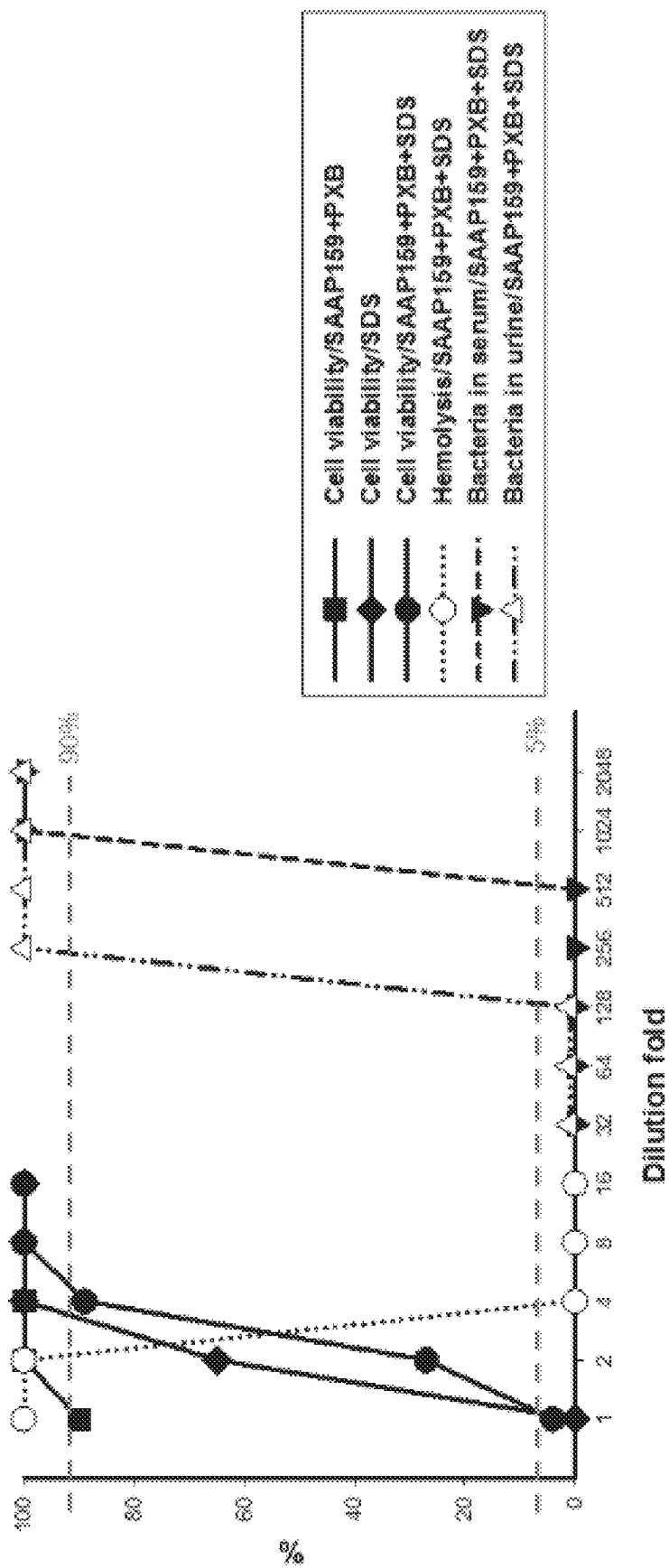
FIG. 8. Cytotoxicity, hemolytic activity and antimicrobial activity of free and released antimicrobials from silicone discs. (A) The free antimicrobials including 16 µg PXB, 8 µg SAAP159 and 25 µg SDS were dissolved in 200 µl urine or in 200 µl RPMI growth medium containing 10% FBS. (B) The released antimicrobials were collected from the serum or urine in which silicone disc had been immersed overnight (200 µl). The cell viability of human bladder cells NTUB1 ($1.5 \times 10^4$ cells/well) treated with free or released antimicrobials were determined by WST1 and expressed in percentage. The hemolysis of mouse red blood cell treated with antimicrobials were measured by the absorbance at the 414 nm and expressed in percentage. The potency of antimicrobial activity was determined by the dilution folds of antimicrobials which is able to inhibit bacterial growth in serum or urine.
Figure 8B:
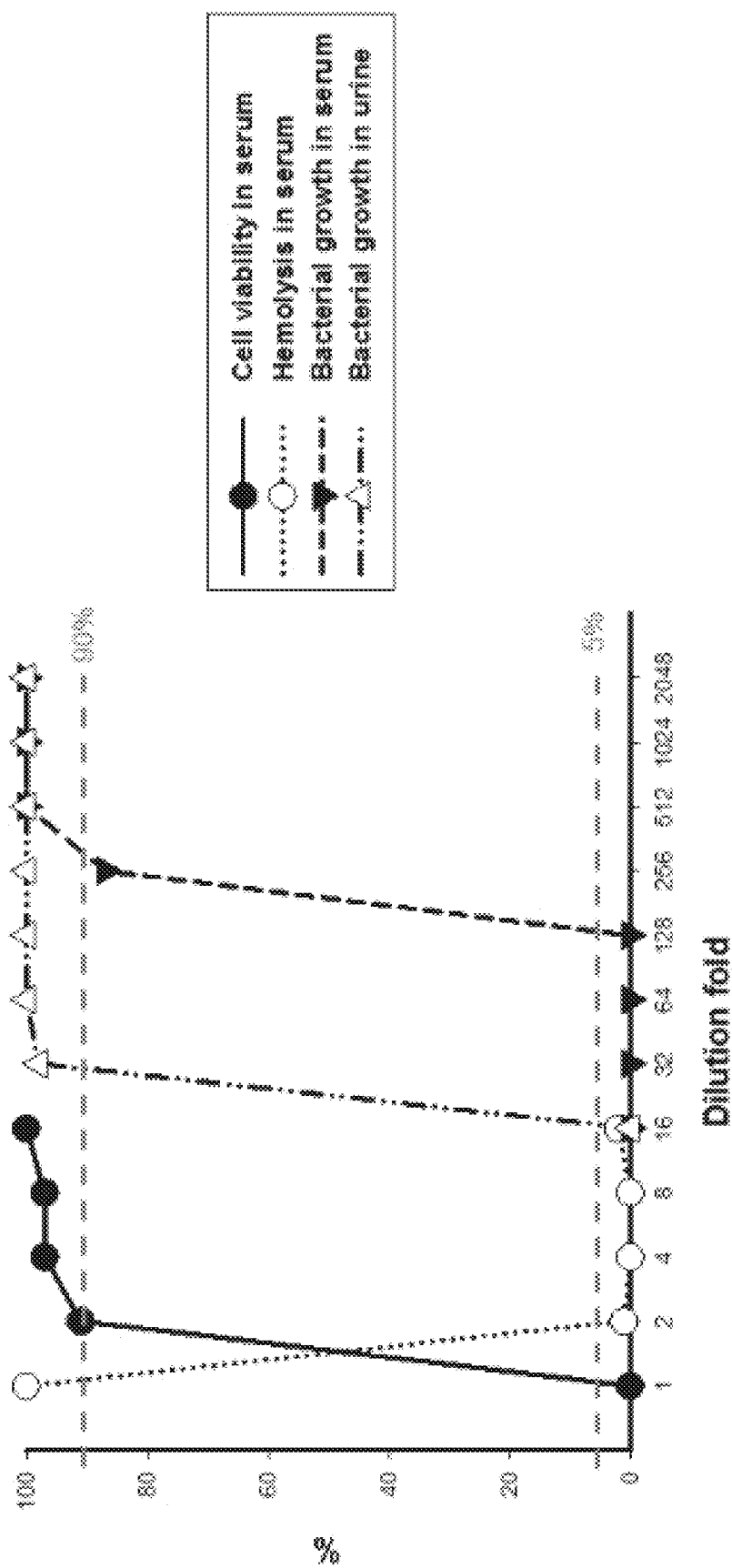
Figure 9A:
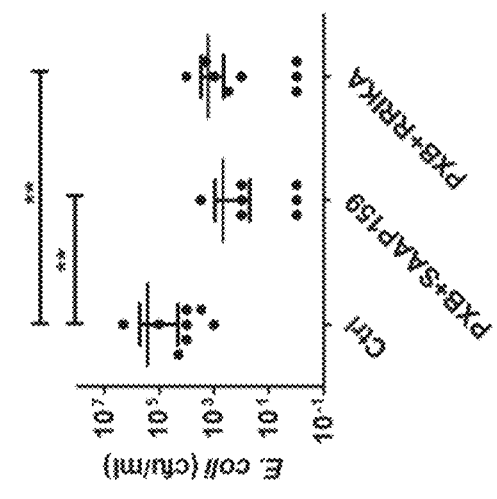
FIG. 9. Antimicrobial activity of PXB-AMP-coated silicone tubing in mouse urinary tract. The silicone tubing and E. coli ATCC23502 ($5 \times 10^9$ cfu/ml in 100 µl PBS) were implanted/instilled into the bladder using a 24G I.V. catheter. Number of survived/attached E. coli were counted in the urine at day 2, 4, 6 and 8 (A-D), the bladder and silicone tubing at day 8 (E,F). The silicone tubing was uncoated (n=8), coated with PXB-SAAP159 (n=7) or PXB-RRIKA (n=8), respectively, by SDS. * indicates P≤0.05,  indicates P≤0.005, * indicates P≤0.0005 and n.s. indicates no significant difference.
Figure 9B:
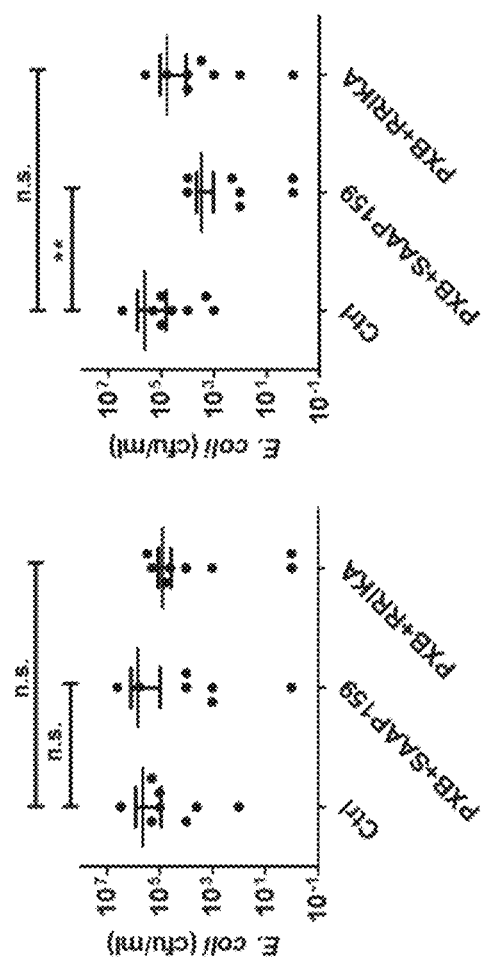
Figure 9C:
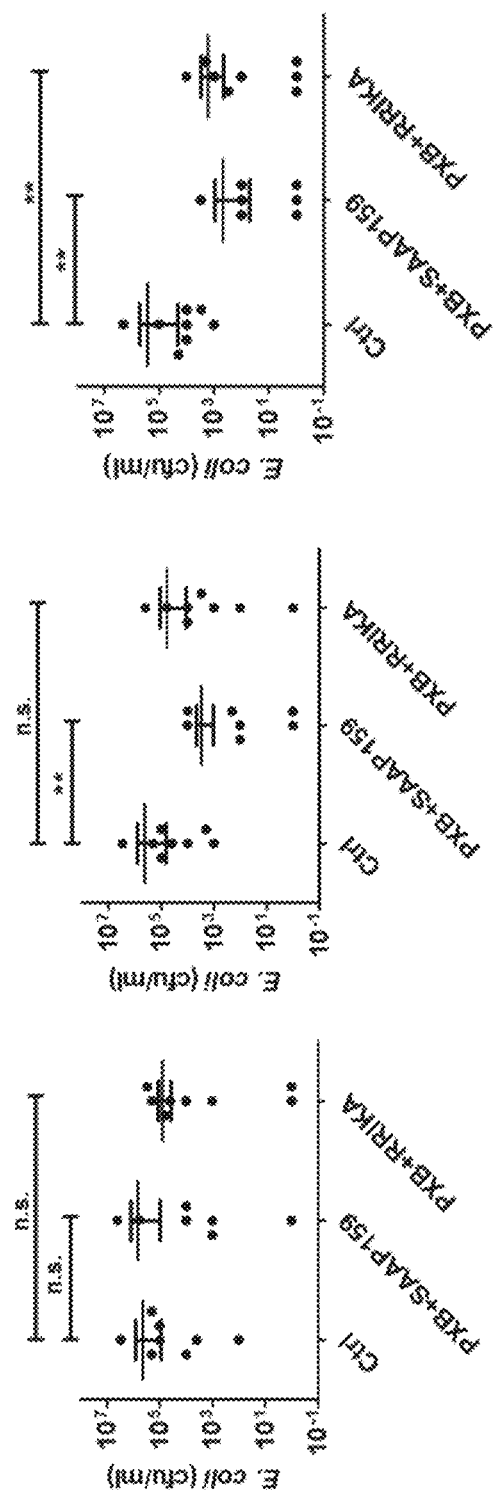
Figure 9D:
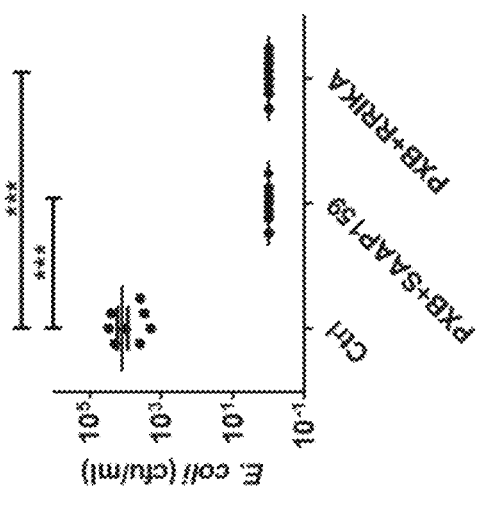
Figure 9E:
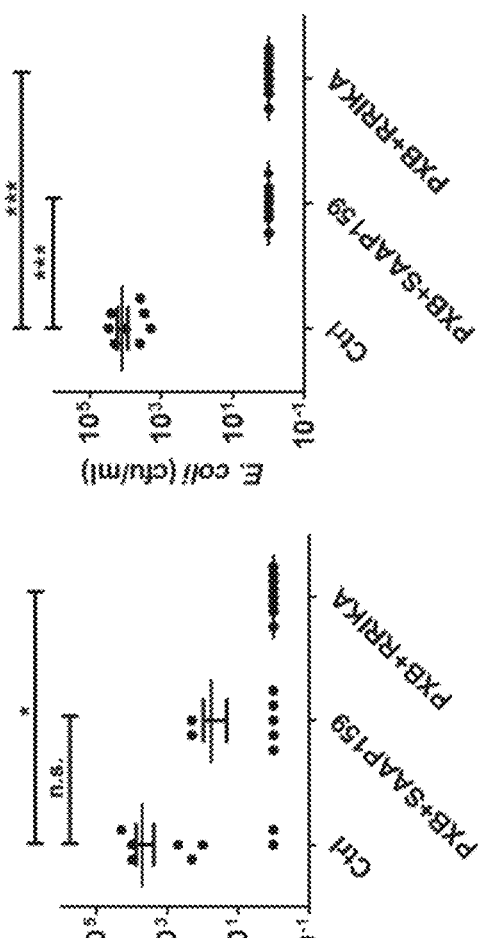
Figure 9F:
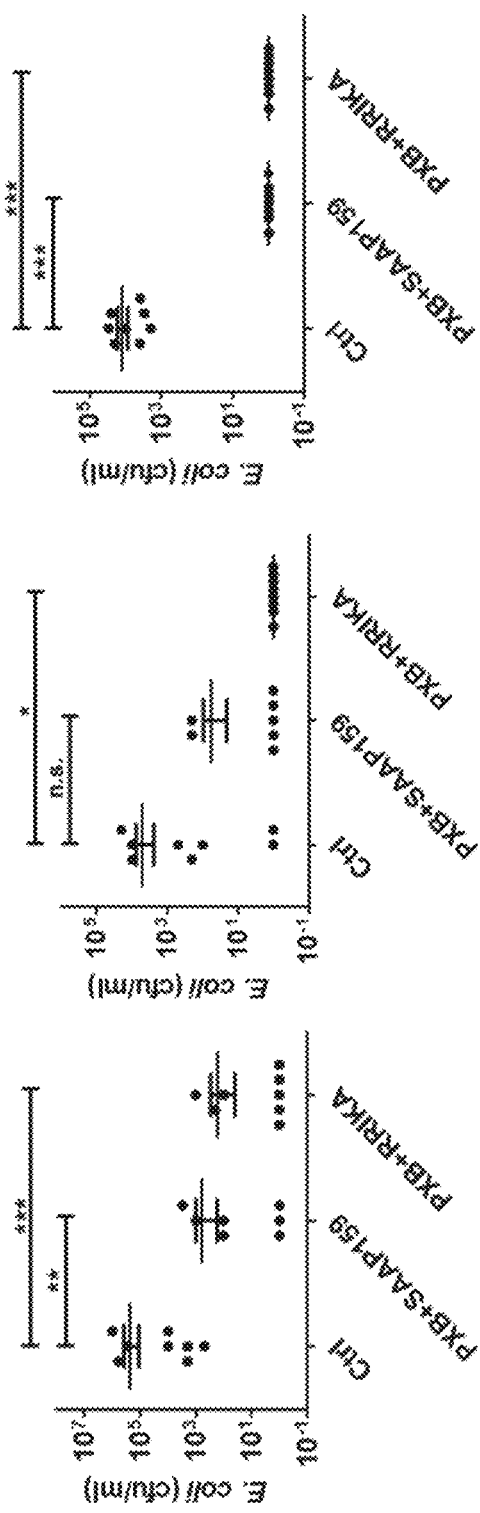

Example 7 Cytotoxic and Hemolytic Activities of AMP/PXB Coated on Silicone Discs To identify the key component(s) which is released from the coated antimicrobials and is responsible for the cytotoxicity and hemolytic activities, individual components involved in the coating of antimicrobials, namely SDS, PXB and SAAP159, were examined. If the full amount of SDS (30 µl of ⅛×SDS plus 30 µl of 1×SDS) was coated onto the substrate (5.8 mm in diameter) and also subsequently completely released into the serum, the maximal amount of SDS would be 25 µg. The cytotoxicity of 25 µg of SDS toward NTUB1 cells in 200 µl was 99%, while this activity was reduced to 35% if half of the total amount was employed for the assay (FIG. 8). The total amount of antimicrobials (8 µg of SAAP159+16 µg of PXB in 200 ul) in free form did not exhibit any significant cytotoxicity (FIG. 7). The combination of antimicrobials and SDS (8 µg of SAAP159+16 µg of PXB+25 µg SDS in 200 µl) exerted higher cytotoxicity compared to that of 25 µg of SDS alone (FIG. 7). However, the overnight released components in the serum (200 µl), including SAAP159, PXB and SDS exhibited lower cytotoxicity toward NTUB1 bladder cells than free SDS alone (FIG. 8). The potencies of cytotoxic and hemolytic activities were quantitated by serial two-fold dilutions and expressed as dilution folds (FIG. 7). The <$LC_{10}$ is defined as the concentration of agent which causes less than 10% cytotoxicity toward NTUB1 bladder cells after overnight incubation. For example, the free SAAP159/PXB/SDS exerted <10% cytotoxicity after 4-folds dilution (Table 5). Similarly, the potency of bactericidal activities of free or released components in 200 µl serum or urine were also determined by 2-fold serial dilutions for the inhibition of bacterial growth, determined as minimal inhibitory concentration (MIC). For example, the free triple components (SAAP159/PXB/SDS) reached the MIC against *E. coli* in serum and urine after being diluted 512 folds and 128 folds, respectively. The potencies of bactericidal activity of released antimicrobials in serum and urine were 128 folds and 16 folds, respectively (Table 5).

TABLE 5

Potency of PXB + AMP released from silicone disc and expressed in dilution fold (x).

| | Potency (x) | | | |
|---|---|---|---|---|
| | Cytotoxicity to NTUB1*[3] | Hemolysis of RBC | MIC to *E. coli**[4] | |
| AMPs | $IC^{50}$ | $HC^{50}$ | Serum | Urine |
| Free form*[1] | | | | |
| 16 µg PXB | <1 | <1 | 512 | 128 |
| 25 µg SDS | 1-2 | 1-2 | <1 | <1 |
| SAAP159/PXB | <1 | <1 | 512 | 128 |
| SMAP29/PXB | <1 | <1 | 256 | 128 |
| RRIKA/PXB | <1 | <1 | 512 | 128 |
| PXB/SDS | 2-4 | 1-2 | 256 | 128 |
| SAAP159/PXB/SDS | 2-4 | 2-4 | 512 | 128 |
| SMAP29/PXB/SDS | 2-4 | 2-4 | 256 | 128 |
| RRIKA/PXB/SDS | 2-4 | 2-4 | 512 | 128 |
| Released from silicone o/n*[2] | | | | |
| SAAP159/PXB/SDS | 1-2 | 1-2 | 128 | 16 |
| SMAP29/PXB/SDS | <1 | 1-2 | 128 | 16 |
| RRIKA/PXB/SDS | 1-2 | 1-2 | 128 | 16 |

*[1] 1× free antimicrobials contains 8 µg AMP, 16 µg PXB, and/or 25 µg SDS in 200 µl.
*[2] The released antimicrobial was taken from the serum or urine (200 µl) in which antimicrobial-coated silicone disc was immersed overnight.
*[3] NTUB1 cells were seeded at $1.5 \times 10^4$ cell/well
*[4] *E. coli* (ATCC23502) was seeded at $3 \times 10^6$ cfu/ml

Example 8 PXB-AMPs Coated onto Silicone Tubing for the Prevention of Urinary Tract Infection in Mouse The *E. coli* 23502 bacterial growth in urine of mouse implanted with uncoated silicone tubing remained constant (2-4×$10^5$ cfu/ml on average) from day two to day eight after bacterial instillation, whereas mice implanted with PXB-SAAP159 or PXB-RRIKA-coated tubing markedly reduced the survival of *E. coli* (2-6×$10^2$ cfu/ml). The viable bacteria that adhered onto the bladder and silicone tubing were also counted after homogenization and sonication, respectively. Bacteria that adhered on the bladder after sacrifice at day eight was 5×$10^3$ cfu/bladder in the control group, while *E. coli* in the PXB-SAAP159-coated group and in the PXB-RRIKA-coated group was found to be 58 cfu/bladder and zero cfu, respectively. Furthermore, the amount of bacteria that adhered to uncoated silicone tubing was 1.2×$10^4$ cfu/tubing, whereas no bacteria was found to be adherent to the tubing coated with either PXB-SAAP159 or PXB-RRIKA (FIG. 9). These results demonstrate that the silicone tubing coated with PXB-AMPs using SDS can effectively inhibit bacterial growth in mouse urine and also prevent bacterial adherence to mouse bladder and the implanted silicone tubing.

Figure 10A:
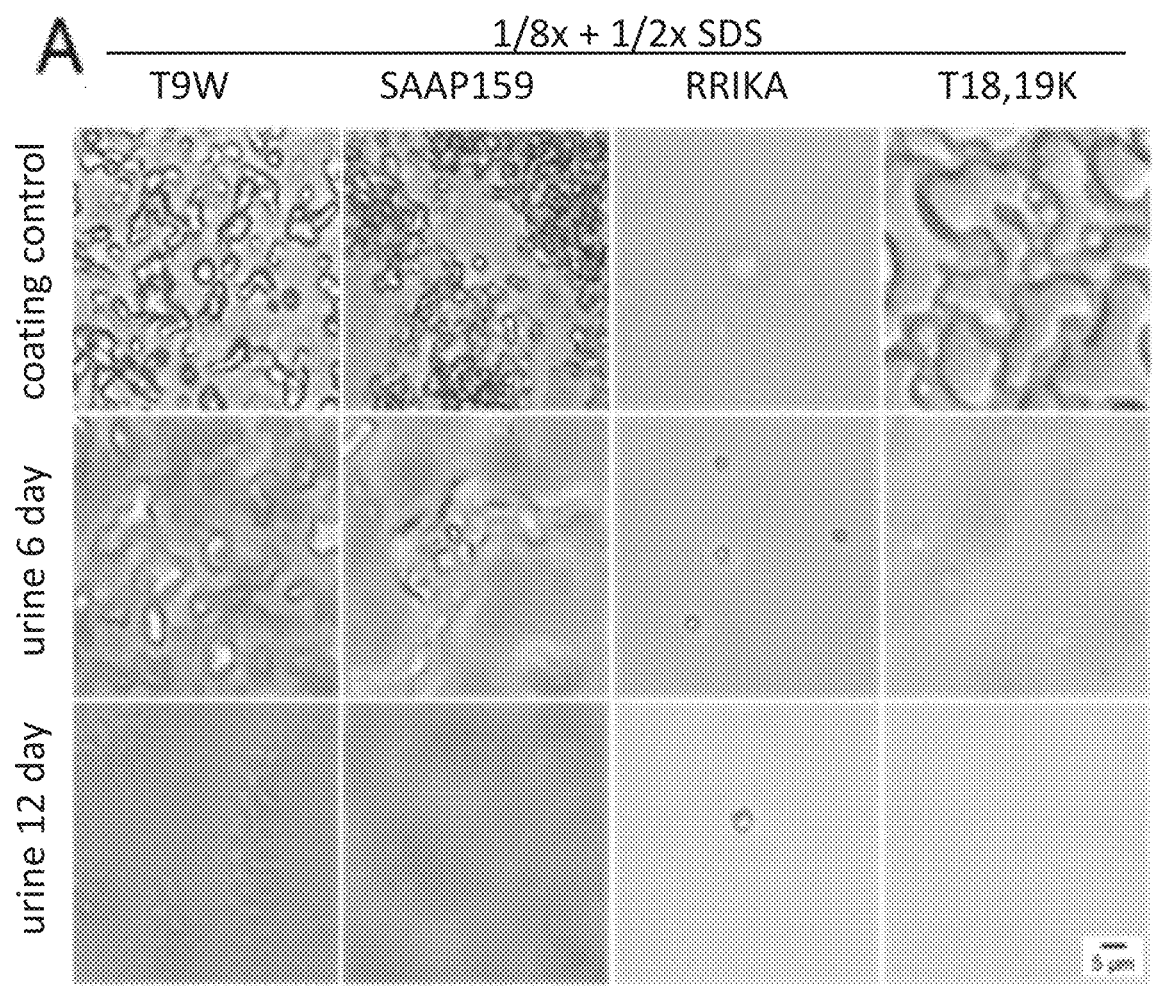
FIG. 10. Coating efficiency and stability of AMPs on polystyrene coated by SDS or SDBS. AMPs (T9W, SAAP159, RRIKA, and T18,19K) were coated on polystyrene 96-well microplates by SDS (A, C, E) and SDBS (B, D, F). (A, B) Morphology of coated AMPs in the presence of urine. (C-F) Stabilities of coated AMPs in urine (C-D) or 10% fetal bovine serum (E, F). 4 µg AMPs and their equivalents left in the well were taken for analysis by 15% SDS-PAGE.
Figure 10B:
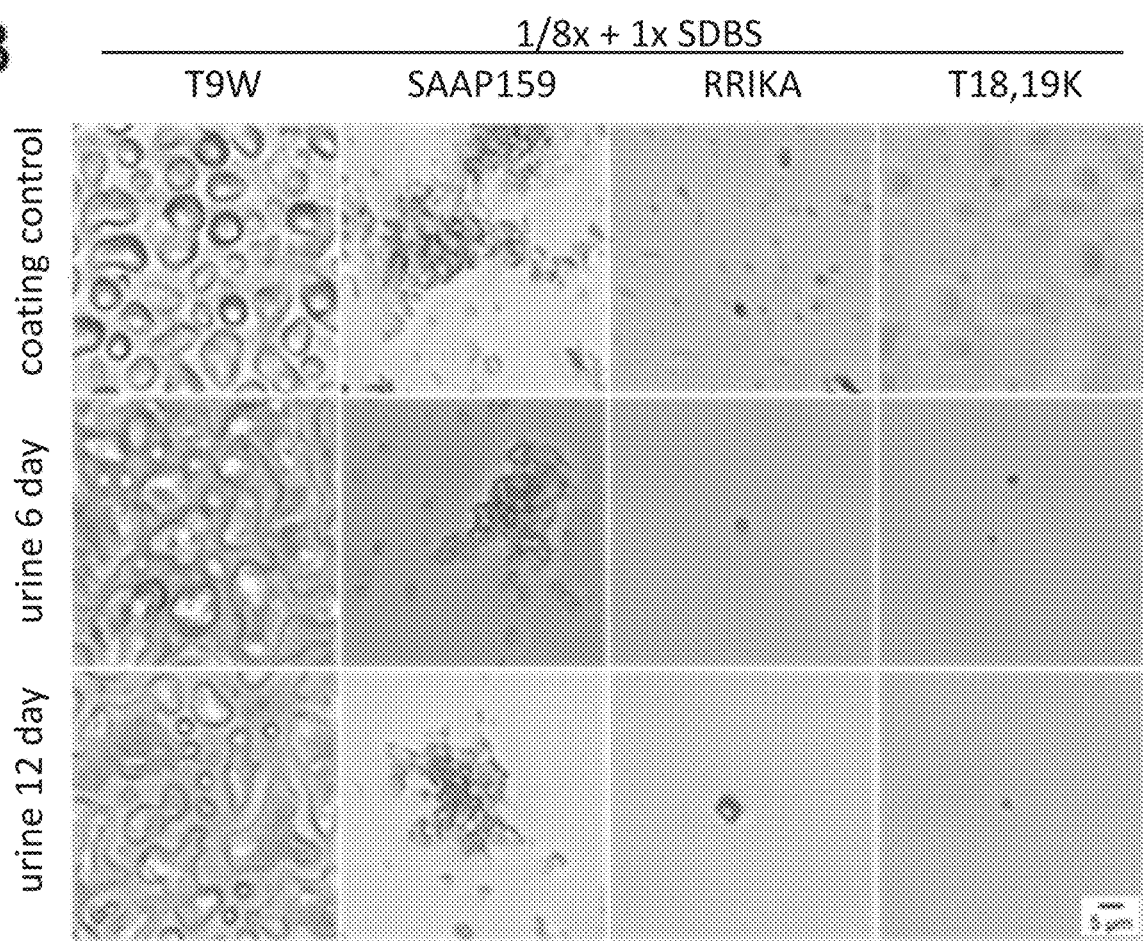

Example 9 Vesicle Formation and Coating of Antimicrobial Peptides onto Polystyrene by Anionic Surfactants The antimicrobial peptides (AMPs) T9W, SAAP159, RRIKA and T18,19K readily dissolved in aqueous solution, however they became cloudy in appearance if anionic surfactants, such as SDS or SDBS, was added at a wide range of concentrations. They existed in small vesicle-like structures (hereinafter referred to as vesicles) and are deposited on the polystyrene-based 96-well microplates with diameters ranging from 1-10 μm, when they were coated by the two-step surfactant coating method. The concentration of 0.075% (w/v) surfactant, SDS and SDBS, was designated as 1×SDS and 1×SDBS, respectively. The optimal conditions for vesicle formation of these AMPs, T9W, SAAP159, RRIKA and T18,19K, were selected as shown in FIG. 10A-B, top panel. However, they gradually dissolved into human urine at different rates. To determine the coating efficiency and relative stability of these coated AMPs in urine, the substrate-attached AMPs were dissolved by SDS-loading buffer and analyzed by SDS-PAGE. The results show that SAAP159 coated by SDS was stable in urine for 12 days, T9W and T18,19K for 6 days. The results of RRIKA coated by SDS were shown in FIG. 10C. When coated by SDBS, the coating efficiency and urine stability of these AMPs were similar to that when coated by SDS (FIG. 10D). These results are in a good agreement with those observed using microscopy (FIG. 10A-B). With respect to the stability of these AMPs in serum, SAAP159 and T9W, when coated by SDS were stable for one to two days, while RRIKA and T18,19K were found to be not stable. It is worthy to mention that when coated by SDBS, these AMPs were more stable in serum compared with the same AMPs that were coated by SDS (FIG. 10E-F). In addition, the coating efficiency and serum stability of another four AMPs coated by SDBS were also examined. The results show that the TP4-derived peptide TP4-A12,15I and RR12 were stable in 10% FBS for two days, whereas SMAP29 and its derived peptide SMAP28-3+2 remained stable for one day only (FIG. 17).

Example 10 Coating of Two AMPs Simultaneously on Polystyrene by SDS and SDBS

Figure 11A:
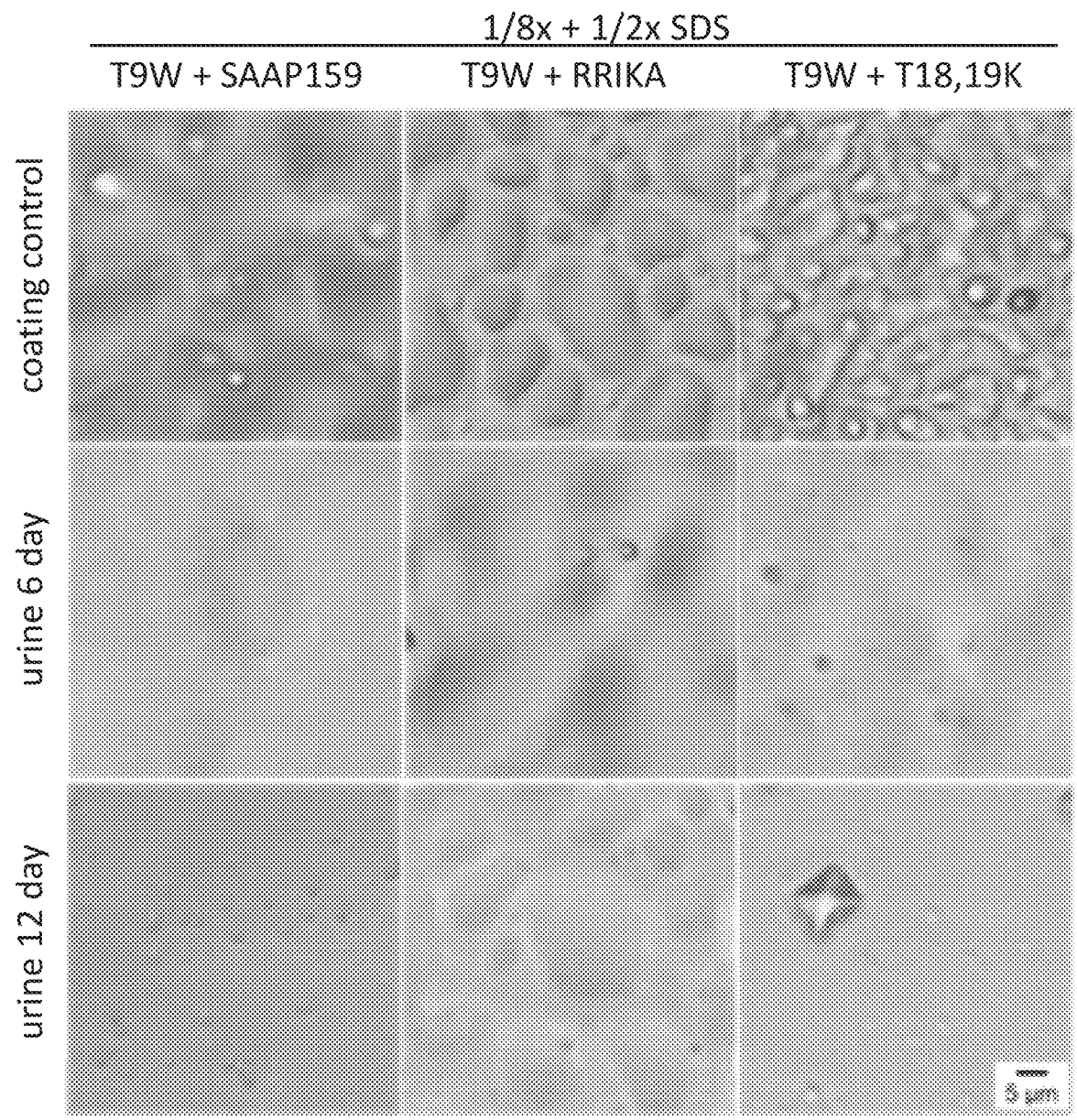
FIG. 11. Coating efficiency and stability of paired AMPs on polystyrene coated by SDS or SDBS. (A-B). Morphologies of paired AMPs (T9W+SAAP159, T9W+RRIKA, and T9W+T18,19K) coated by SDS (A) and SDBS (B) in the presence of urine. (C-F) Stabilities of above paired AMPs in urine (C, D) and 10% fetal bovine serum (E, F). 4 µg AMPs and their equivalents left in the well were taken for analysis by 15% SDS-PAGE.
Figure 11B:
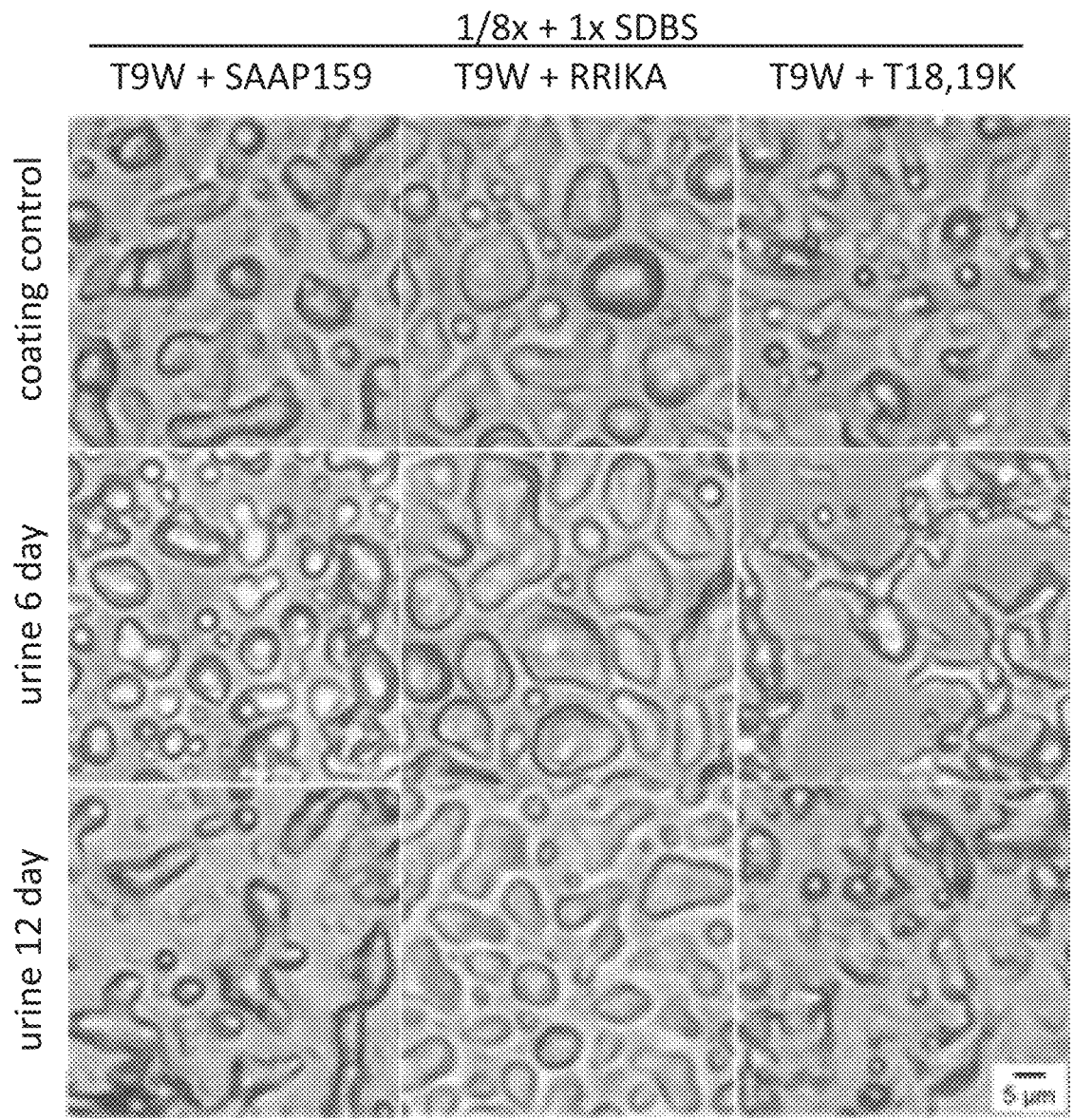

1. Coating of SMAP29 Peptides on Microplates by SDS and Sarkosyl and Stability in Urine The individual AMPs as mentioned above exhibited differential antimicrobial activities against Gram-negative (*E. coli* 23502, *Pseudomonas aeruginosa* 27853), Gram-positive (*Staphylococcus aureus*) bacteria and fungus (*Candida albicans*) as determined by the inhibition zone assay on agar plate (FIG. 18). SMAP29 exhibited a broad spectrum of antimicrobial activities against both Gram-negative and Gram-positive bacteria. RR12 was very active against Gram-positive *S. aureus*. T9W preferentially killed Gram-negative *P. aeruginosa* 27853. With respect to the MIC method, the SMA29 and RR12 were the most effective against *E. coli* and *S. aureus* (Table S2). To broaden the spectrum of antimicrobial activities of the coated AMPs, and possibly increase their coating efficiency and stability in urine and serum, we coated two AMPs simultaneously at different combinations onto the microplates. These AMP combinations were examined by microscopy to evaluate the morphology of paired AMPs' vesicles incubated in urine (0, 6, 12 day) (FIG. 11A-B) or in 10% FBS (0, 2, 3 day). By SDS-PAGE analysis, the selected AMP pairs (T9W+ SAAP159 and T9W+RRIKA) were found to be efficiently coated and stably adhered to the substrate even after a 12-day urine treatment with daily changes of fresh urine. It is worthy to mention that the stability of individual AMPs of the T9W+SAAP159, T9W+RRIKA and T9W+T18,19K AMP pairs coated on the polystyrene microplate by surfactant SDBS was relatively higher than that coated by SDS (FIG. 11C-D). Similarly, the individual AMPs of these AMP pairs coated by surfactant SDBS possessed higher stability in 10% FBS than that coated by SDS (FIG. 11E-F). In addition, another seven selected AMP pairs were also coated by SDBS and examined under the microscope (FIG. 19A-B) and by SDS-PAGE analysis (FIG. 19C-D) to evaluate their coating efficiencies and stabilities. Four of them (T9W paired with TP4-A12,15I, SMAP28-3+2 and RR12, RR12 paired with SAAP159) remained stable in 10% FBS for more than three days.

TABLE S2

MIC (μg/ml) and MBC (μg/ml) of individual AMPs against *E. coli* and *S. aureus*.

| | *E. coli* 23502; LB (3.5 × 10$^5$ cfu/ml) | | *S. aureus*; TSB (4 × 10$^5$ cfu/ml) | |
|---|---|---|---|---|
| AMP | MIC | MBC | MIC | MBC |
| T9W | >512 | >512 | >512 | >512 |
| SAAP159 | 64 | 64 | 512 | >512 |
| RR1KA | 128 | 128 | 64 | 128 |
| T18,19K | 64 | 64 | >512 | >512 |
| RR12 | 4 | 4 | 4 | 4 |
| TP4-A12,15I | 32 | 32 | 32 | 32 |
| SMAP29 | 4 | 4 | 4 | 4 |
| SMAP28-3 + 2 | 4 | 8 | 32 | 32 |

Example 11 Coating of AMP Pairs onto Silicone, Polyurethane and Titanium

Figure 12A:
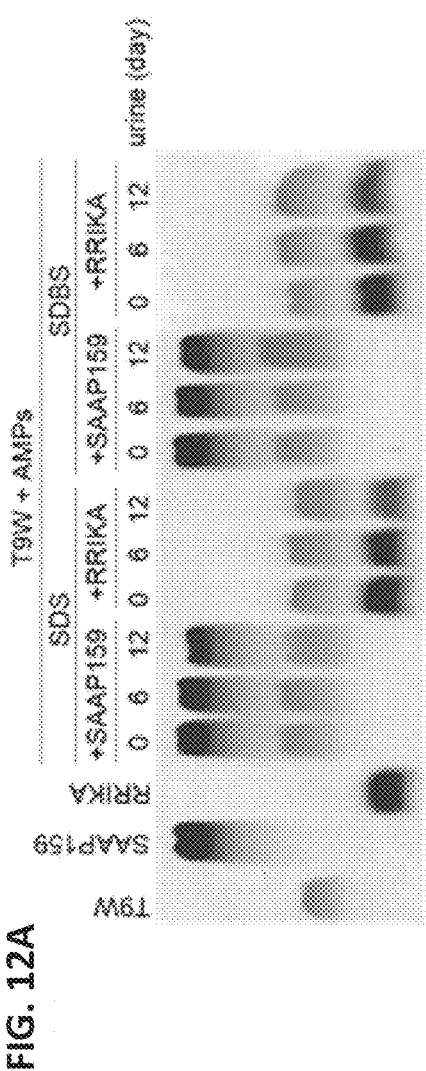
FIG. 12. Stability of paired AMPs coated on silicone disc by SDS or SDBS in the presence of urine and serum. (A-B) Stability of paired AMPs (T9W+SAAP159 and T9W+
Figure 12B:
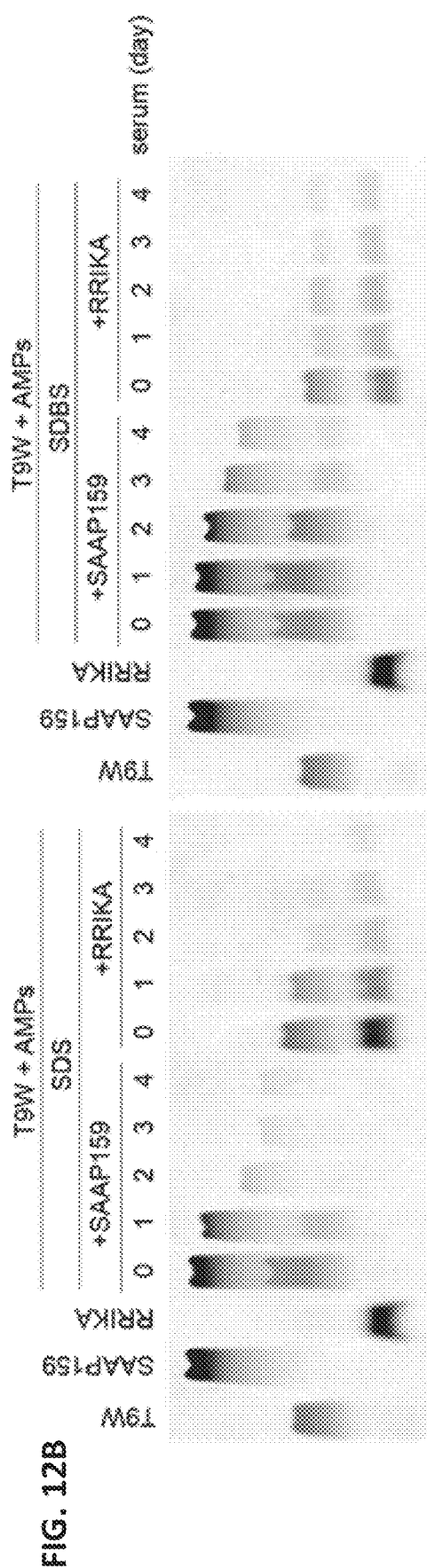
Figure 12C:
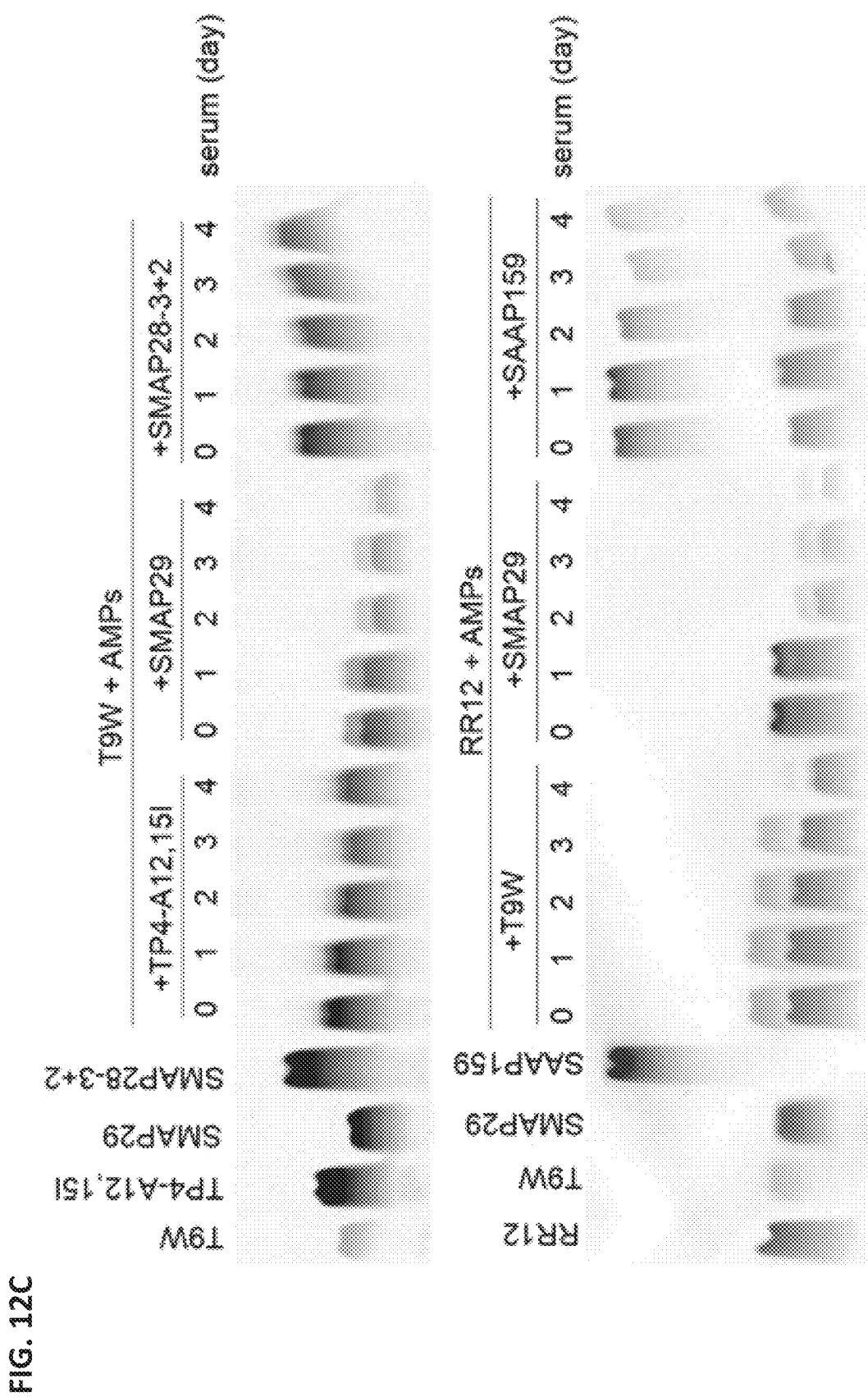
Figure 14B:
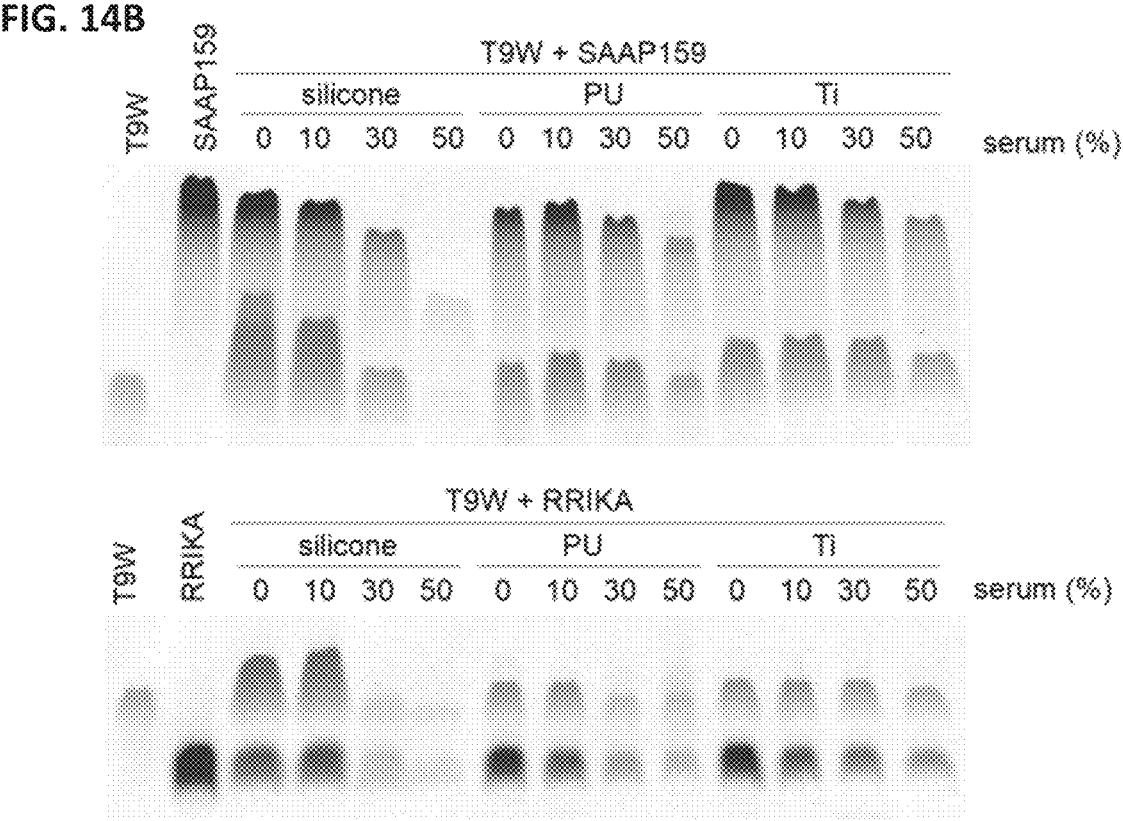

Silicone is widely used in biomedical devices including central venous catheter and urinary catheter, therefore AMP pairs were coated onto silicone discs by SDS or SDBS and examined for their coating efficiency and stability in urine and in 10% FBS under the microscopy first, then by SDS-PAGE analysis. The individual AMPs of two selected AMP pairs (T9W+SAAP159, T9W+RRIKA) coated by either SDS or SDBS were tightly bound to the substrate after a 12-day urine incubation with daily changes of fresh urine (FIG. 12A). Furthermore, the individual AMPs of these two AMP pairs (T9W+SAAP159, T9W+RRIKA) coated by SDS or SDBS was stable in 10% FBS for three to four days (FIG. 12B). Similarly, the other six AMP pairs (T9W+TP4-A12, 15I, T9W+SMAP29, T9W+SMAP28-3+2, T9W+RR12, RR12+SMAP29, RR12+SAAP159) when coated by SDBS also tightly bound to the substrate in 10% FBS for four days (FIG. 12C). To select the most stable AMP pairs in FBS, they were further subjected to 30% or 50% FBS treatment overnight. The T9W+SAAP159, T9W+SMAP28-3+2 and T9W+TP4-A12,15I AMP pairs exerted the highest stability in FBS, followed by RR12+SAAP159, T9W+RRIKA, T9W+RR12, T9W+SMAP29, and RR12+SMAP29, in descending order (FIG. 13). In addition to the polystyrene and silicone substrates as mentioned above, these two AMP pairs (T9W+SAAP159, T9W+RRIKA) were also successfully coated onto the polyurethane (PU) and titanium (Ti) discs by SDBS and remained stable in 10% FBS for three days (FIG. 14A) or in 30% and 50% FBS after overnight incubation (FIG. 14B). These two substrates are also widely used in biomedical devices.

Example 12 Bactericidal Activity of AMP Pairs Coated by SDS and SDBS

After a 12-day urine treatment with daily changes of fresh urine, the selected AMP pairs (T9W+SAAP159 and T9W+RRIKA) coated by the two-step (⅛×+½×) SDS buffer onto polystyrene microplates retained strong bactericidal activities against human isolate *E. coli* 23502 ($10^3$-$10^4$-folds reduction), while their bactericidal activity lasted for only for one to two days in 10% FBS (Table 6). In contrast, these AMP pairs coated by two-step (⅛×+1×) SDBS buffer did not exert bactericidal activity even without urine treatment (less than 10-folds reduction), because they were tightly bound to the substrate even after the 12-day urine treatment as shown in FIG. 11C-D. In contrast, they were bactericidal to *E. coli* 23502 for two days in 10% FBS, which was longer than the bactericidal activity of the same AMP pairs when coated by SDS. The results nicely correlated with the amount of AMPs which remained on the substrate (FIG. 11E-F), suggesting that the bactericidal activities of the paired AMPs is attributed to by the level of AMPs that can become released from the substrate.

TABLE 6

Bactericidal activity of paired AMPs coated on polystyrene against *E. coli* after urine or 10% serum treatment.

| | | Bacteria growth of *E. coli* 23502 (cfu/ml)*[1] | | | | | | | |
|---|---|---|---|---|---|---|---|---|---|
| | Surfactant | urine | | | | 10% serum in RPMI | | | |
| AMPs | (x) | 0 day | 3 day | 6 day | 12 day | 0 day | 1 day | 2 day | 3 day |
| Control*[2] | | $1.4 \times 10^7$ | $3.9 \times 10^7$ | $3.2 \times 10^7$ | $1.9 \times 10^7$ | $3.1 \times 10^7$ | $2.7 \times 10^7$ | $1.6 \times 10^7$ | $2.6 \times 10^7$ |
| T9W/SAA159 | SDS | 0 | 0 | $1.0 \times 10^2$ | $3.0 \times 10^3$ | 0 | $8.7 \times 10^3$ | $3.9 \times 10^3$ | $1.0 \times 10^7$ |
| T9W/RRIKA | (⅛ + ½) | 0 | 0 | $1.0 \times 10^2$ | $2.6 \times 10^4$ | 0 | $2.0 \times 10^2$ | $1.7 \times 10^5$ | $1.8 \times 10^7$ |
| T9W/SAAP159 | SDBS | $2.0 \times 10^6$ | n.d. | n.d. | n.d. | $3.1 \times 10^3$ | $3.9 \times 10^2$ | $4.0 \times 10^2$ | $7.0 \times 10^5$ |
| T9W/RRIKA | (⅛ + 1) | $1.6 \times 10^6$ | | | | $1.8 \times 10^3$ | $3.7 \times 10^4$ | $3.9 \times 10^4$ | $1.55 \times 10^6$ |

*[1]The *E. coli* ATCC23502 was seeded at $2 \times 10^5$ cfu/ml.
*[2]Microplate without coating was used as control.

Example 13 Inhibition of Bacterial Adherence

To determine this approach's potential application in reducing biomaterial-associated infections in clinics especially in the urinary tract, the adherence of bacteria to silicone which is the major material for human catheter, was evaluated. The adherence of *Pseudomonas aeruginosa* 27853 to silicone disc was markedly decreased (100-folds reduction) by two AMP pairs (T9W+SAAP159 and T9W+RRIKA) coated by either SDS or SDBS even after a 14-day urine incubation with daily changes of fresh urine (Table 7). These results are in a good agreement with the amount of AMPS that remained on the silicone discs (FIG. 12A).

TABLE 7

Anti-adherence activities of paired AMPs on silicone disc against *P. aeruginosa* 27853 after urine treatment.

| | | Bacteria adhered on silicone disc (cfu/disc)* | | | | |
|---|---|---|---|---|---|---|
| | Surfactant | Pre-treated with urine | | | | |
| AMPs | (x) | 0 day | 3 day | 7 day | 10 day | 14 day |
| Control | | $3.5 \times 10^5$ | $3.5 \times 10^5$ | $4.1 \times 10^5$ | $7.9 \times 10^5$ | $3.5 \times 10^5$ |
| T9W/SAAP159 | SDS | $7 \times 10^1$ | $1.3 \times 10^2$ | $6.7 \times 10^3$ | $1.8 \times 10^3$ | $4.8 \times 10^3$ |
| T9W/RRIKA | (⅛ + ½) | 0 | $5.1 \times 10^2$ | $4.2 \times 10^2$ | $2.3 \times 10^3$ | $2.6 \times 10^3$ |
| T9W/SAAP159 | SDBS | $3.4 \times 10^2$ | $4.6 \times 10^2$ | $2.3 \times 10^3$ | $5.6 \times 10^2$ | $1.8 \times 10^3$ |
| T9W/RRIKA | (⅛ + 1) | $3.7 \times 10^2$ | $2 \times 10^1$ | $7.4 \times 10^2$ | $8 \times 10^1$ | $4.7 \times 10^3$ |

*[1]The *E. coli* ATCC23502 was seeded at $2 \times 10^5$ cfu/ml.
*[2]Microplate without coating was used as control.

Figure 20A:
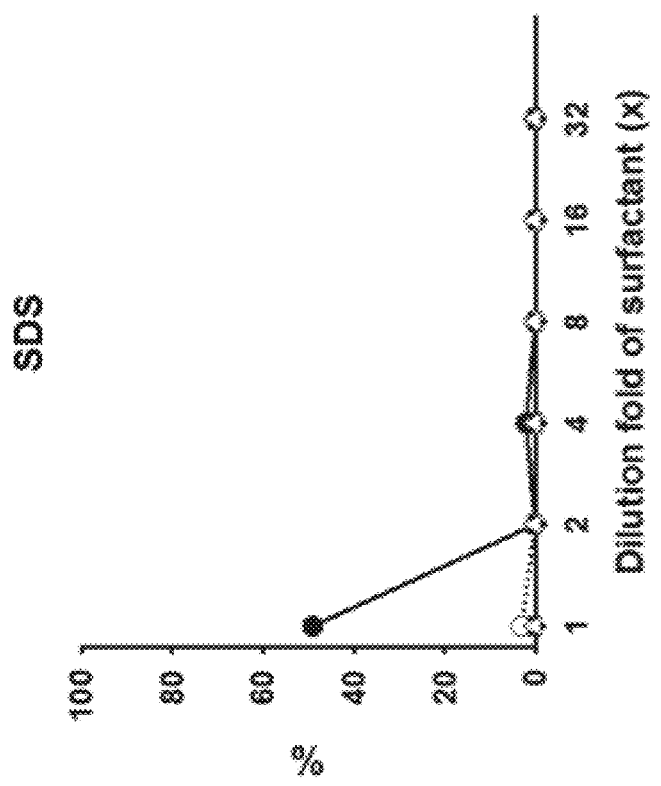

Example 14 Cytotoxic, Hemolytic and Bactericidal Activities of Paired AMPs Coated on Silicone Discs The maximal amount of surfactant that may be coated on both sides of silicone discs and released into solution is 14 µg for SDS and 25 µg for SDBS per disc. In 200 µl of assay medium, concentrations up to this maximal amount of SDS and SDBS did not exert bactericidal activity against E. coli 23502 in urine or in 10% FBS, and the SDS (14 µg) exhibited only low cytotoxicity toward human bladder cells (NTUB1) and hemolytic activity toward mouse red blood cells (FIG. 20a). Similarly, the maximal amount of selected AMP pairs (T9W+SAAP159 and T9W+RRIKA) that may be coated onto silicone discs and released into serum/urine was 24 µg in total, 12 µg and 12 µg for each AMP. These AMPs exhibited significant bactericidal activity against E. coli 23502 in serum (eight-fold dilution for MIC), but no activity in urine. These AMPs also exhibited very low cytotoxicity and hemolytic activity.

Figure 15A:
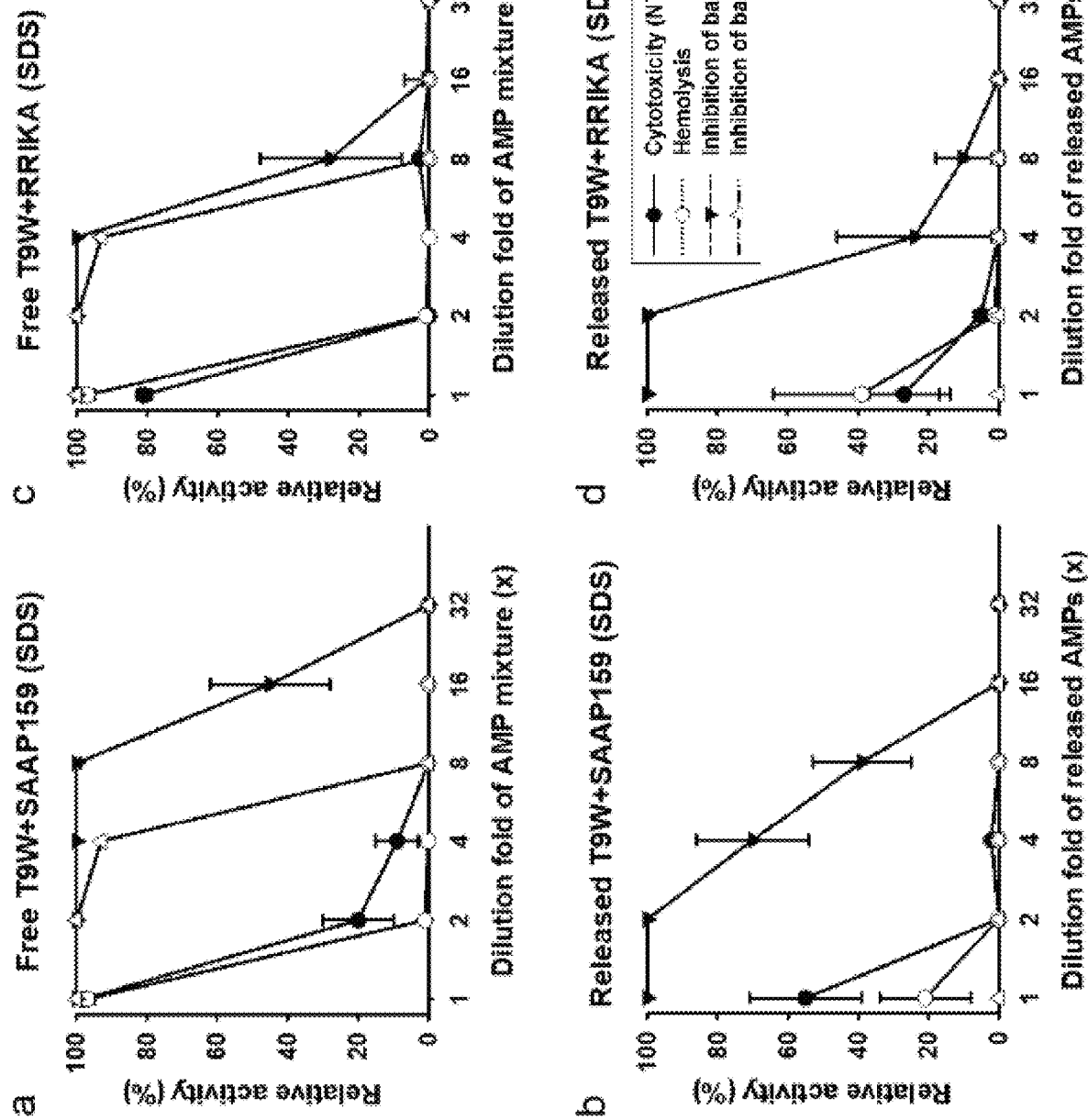
Figure 15B:
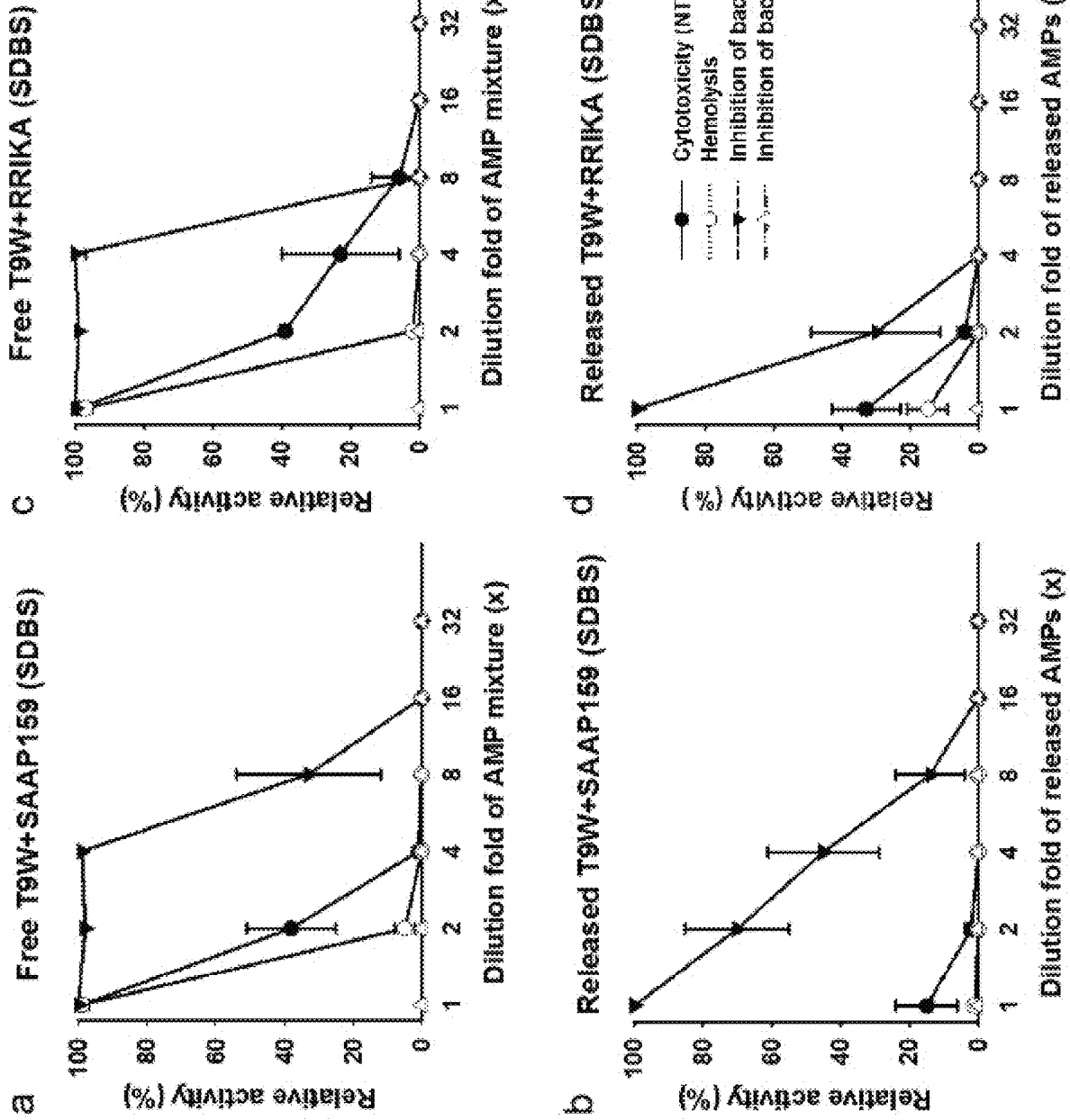

For the combination of the above-mentioned surfactant SDS and paired AMPs that may be coated onto both sides of silicone discs and released as free form, they exerted significant bactericidal activities either in the urine (two- to four-fold dilutions for MIC) or in serum (eight-fold dilution for MIC). These SDS and paired AMPs still exhibited low cytotoxicity (one- to two-fold dilutions for $IC_{50}$) and hemolytic activity (one- to two-fold dilutions for $IC_{50}$) (FIG. 15A-a,c). Interestingly, the combined SDBS and paired AMPs exhibited significant bactericidal activity in serum (eight-fold dilution for MIC), but no activity in urine (FIG. 15B-a,c). With respect to the surfactant (SDS or SDBS) and paired AMPs released from silicone discs into serum or urine overnight, these combinations only exhibit no bactericidal activity in urine and low cytotoxic and/or hemolytic activities. However they exerted significant bactericidal activity (two-fold dilution for MIC) in serum (FIG. 15A-b,d, 15B-b,d).

Figure 16A:
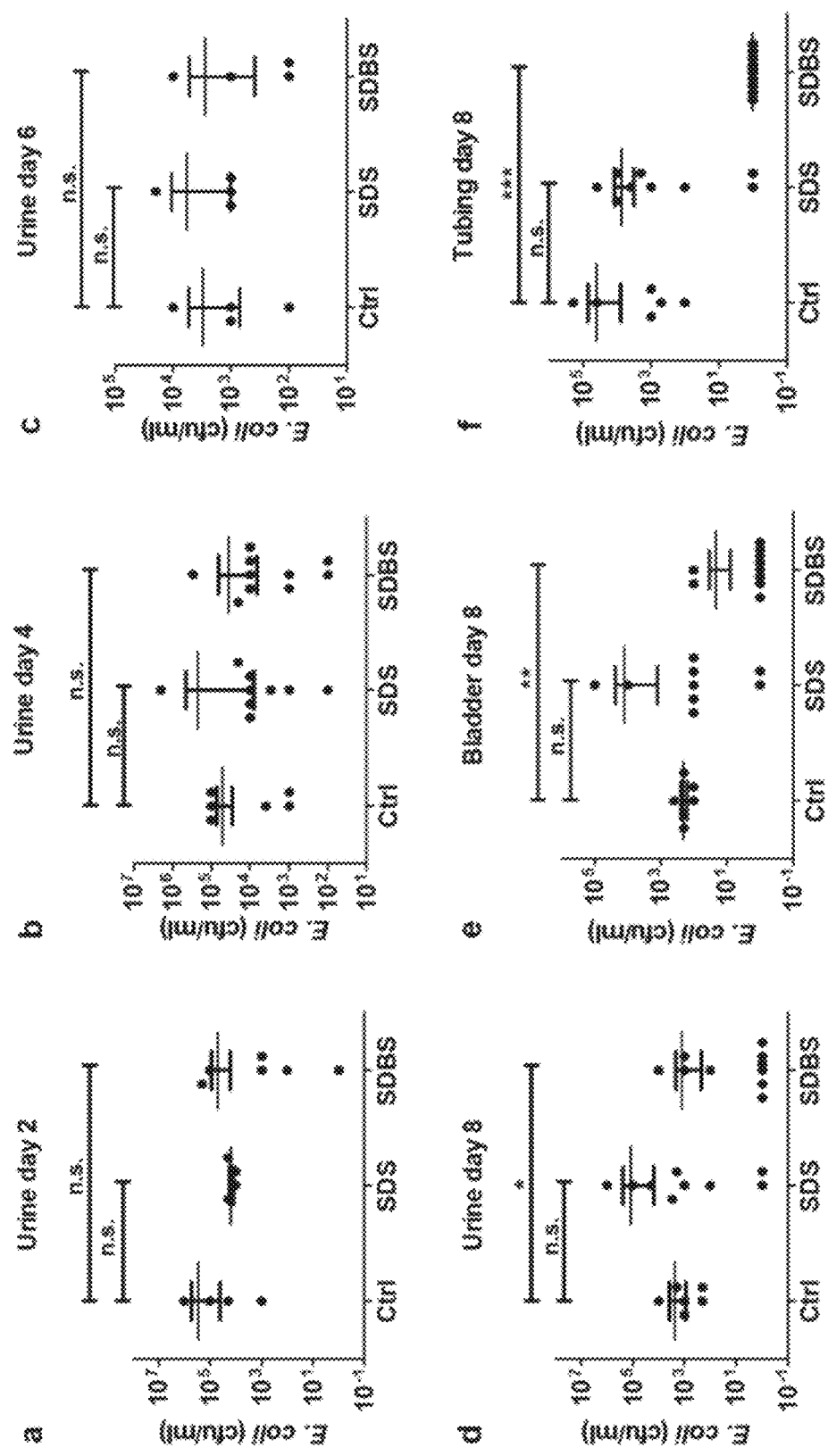
Figure 16B:
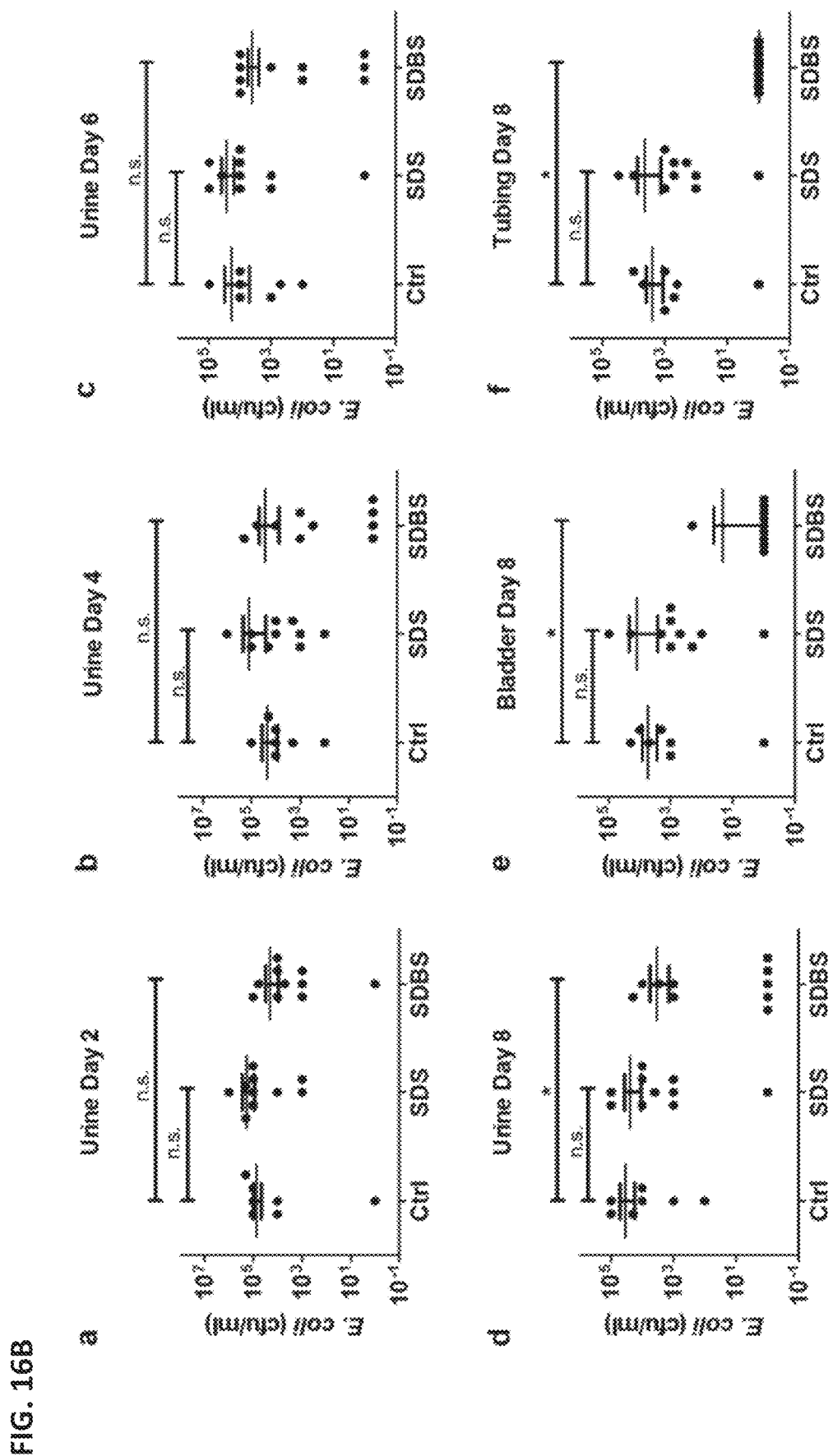
Figure 16C:
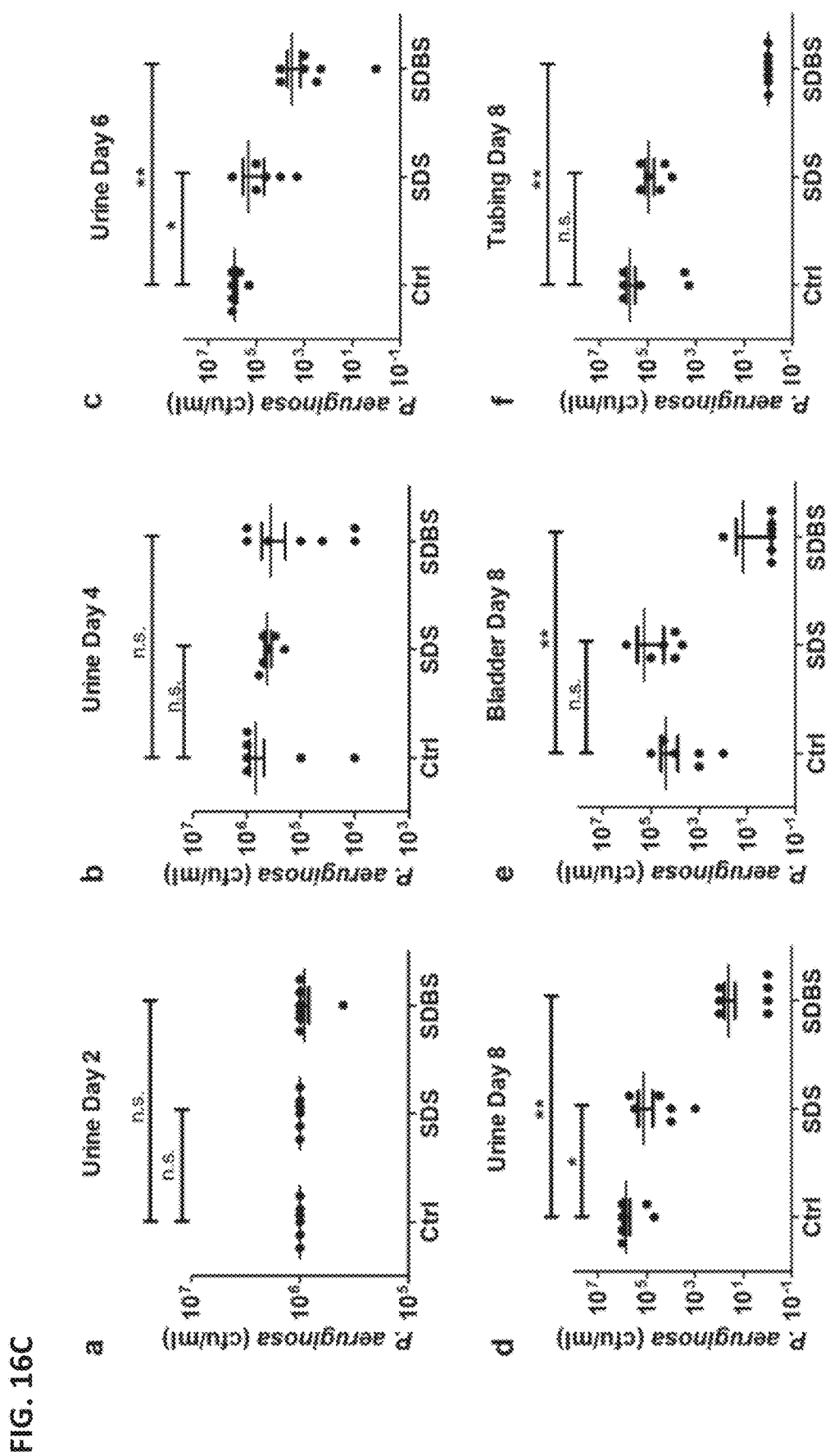

Example 15 Prevention of Urinary Tract Infection by Paired AMPs in a Mouse Model The planktonic growth of E. coli 23502 in urine of mice was not significantly reduced ($1-10\times10^5$ cfu/ml) by the silicone tubing which had been coated with T9W+SAAP159 or T9W+RRIKA, in the presence of SDS and implanted in the bladder. Whereas those implanted with silicone tubing coated with T9W-SAAP159 or T9W+RRIKA, in the presence of surfactant SDBS markedly reduced planktonic growth of E. coli 23502 by two- and 10-folds ($1-2\times10^3$ cfu/ml), respectively, at day eight after bacterial instillation. The amount of viable bacteria that adhered on the bladder in the control group and also in the groups coated with T9W-SAAP159 or T9W-RRIKA, in the presence of SDS were not significantly changed at day eight ($2-12\times10^3$ cfu/bladder), whereas the planktonic growth of E. coli 23502 in those groups which had AMP pairs coated in the presence of SDBS were markedly reduced by approximately 100-fold (20 cfu/bladder). Most importantly, the amount of bacteria that adhered to the silicone tubing without coating or to those silicone tubing coated with T9W+SAAP159 and T9W+RRIKA in the presence of SDS were not significantly changed ($2-40\times10^3$ cfu/tubing), whereas no bacteria were found on the tubing coated with either T9W+SAAP159 or T9W+RRIKA in the presence of SDBS (FIG. 16A-B). The reduction of planktonic growth in urine and prevention of bacterial adherence to silicone tubing were also found in mouse instilled with P. aeruginosa 27853 and implanted with silicone tubing coated with T9W+SAAP159 in the presence of SDBS (FIG. 16C). These results clearly demonstrate that silicone tubing coated with AMP pairs in the presence of surfactant SDBS can effectively inhibit bacterial growth in mouse urine and prevent bacterial adherence onto mouse bladder and onto the implanted silicone tubing.

Example 16 Stability of Paired AMPs Treated by Heat or Ethylene Oxide

Figure 21C:
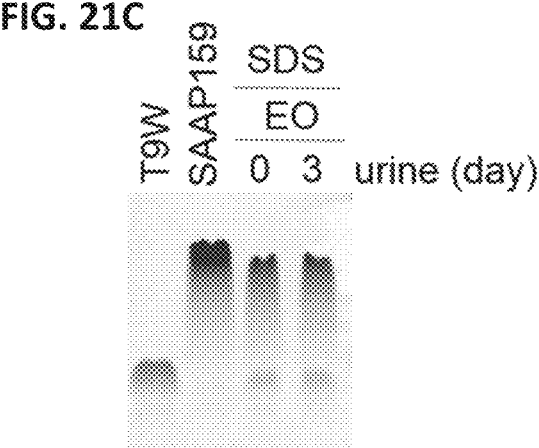

To monitor the potential damages to the coated AMP pairs that are attributed to the sterilization or transportation processes, the stability of T9W+SAAP159 on the microplates coated by SDS or SDBS were examined. No significant change was seen on the stability of these AMPs in urine for seven days after a four-week treatment at 37° C. or 60° C. (FIG. 12A-B). Similarly, the stability of T9W+SAAP159 coated by SDS in urine for three days was not changed after ethylene oxide treatment (FIG. 21C). Furthermore, all of the heated and ethylene oxide-treated AMPs still retained the full level of bactericidal activities against E. coli 23502 when compared with those without treatment.

What is claimed is:

1. A method for coating a surface of a material, comprising
   (i) dissolving one or more antimicrobial peptides (AMPs) in a buffer containing a lower concentration anionic surfactant than 0.002% (w/v) to form solution (a);
   (ii) adding an amount of a buffer containing a higher concentration anionic surfactant than 0.02% (w/v) to the solution (a) to form solution (b), wherein the amount of the buffer containing the higher concentration anionic surfactant is equal to that of the buffer containing the lower concentration anionic surfactant; and
   (iii) coating the solution (b) onto the surface of the material so that the AMPs attach onto the surface.

2. The method of claim 1, wherein the AMPs in the buffer containing the lower concentration anionic surfactant is in an amount ranging from about 0.002% (w/v) to about 0.02% (w/v) and the AMPs in the buffer containing the higher concentration anionic surfactant is in an amount ranging from 0.02% (w/v) to about 0.6% (w/v).

3. The method according to claim 1, wherein the anionic surfactant is sodium dodecyl sulfate (SDS), sodium lauroyl sarcosinate (sarkosyl), sodium 1-decane sulfonate (SDSn), sodium n-octyl sulfate (SOS) or sodium dodecyl benzene sulfonate (SDBS).

4. The method of claim 1, wherein the AMPs are in an amount ranging from about 0.01% (w/v) to about 0.1% (w/v).

5. The method of claim 1, wherein the material is glass or a synthetic polymer.

6. The method of claim 1, wherein the material is used to make a medical instrument/device or a supporting stuff.

7. The method of claim 6, wherein the medical instrument/device or the supporting stuff is a film, particle, fiber, tube, frame, plate, catheter, stent, contact lens, bone implant, other surgical, dental instrument, or medical device.

8. The method of claim 1, wherein the AMP is a peptide-derived antibiotic, α-helical, β-strand, or coiled peptide.

9. The method of claim 1, wherein the AMP is the peptide selected from SEQ ID Nos: 1 to 23 or a mixture of any two or more thereof.

10. The method of claim 1, wherein the AMP is the peptide of SEQ ID NO: 2, SEQ ID NO:3, SEQ ID NO:14, SEQ ID NO: 15, SEQ ID NO: 16, SEQ ID NO: 18, SEQ ID NO:20 or SEQ ID NO:23 or a mixture of any two or more thereof.

11. The method of claim 1, wherein an AMP pair is used, wherein the AMP pair is a peptide-derived antibiotic in combination with any one of the peptides of SEQ ID Nos: 1 to 23.

12. The method of claim 11, wherein the AMP pair is any one of Polymyxin B, Polymyxin E and Gentamicin in combination with any one of the peptides of SEQ ID Nos: 1 to 23.

13. The method of claim 11, wherein the AMP pair is any one of Polymyxin B, Polymyxin E and Gentamicin in combination with any one of the peptides of SEQ ID NO:2, SEQ ID NO:3, SEQ ID NO:16, or SEQ ID NO: 18.

14. The method of claim 11, wherein the AMP pair is SEQ ID NO:23 in combination with SEQ ID NO:3, SEQ ID NO:23 in combination with SEQ ID NO:14, SEQ ID NO:23 in combination with SEQ ID NO:15, SEQ ID NO:23 in combination with SEQ ID NO:16, SEQ ID NO:23 in combination with SEQ ID NO:20, SEQ ID NO:14 in combination with SEQ ID NO:16 or SEQ ID NO:14 in combination with SEQ ID NO:18.

15. The method of claim 6, wherein the medical instrument/device or supporting stuff has antimicrobial activity.

16. The method of claim 5, wherein the medical instrument/device or the supporting stuff inhibits both Gram-positive and Gram-negative bacteria.

* * * * *

SEQUENCE LISTING

```
<160> NUMBER OF SEQ ID NOS: 26

<210> SEQ ID NO 1
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Arg Phe Lys Arg Phe Arg Lys Lys Phe Lys Lys Leu Phe Lys Lys
1               5                   10                  15

Leu Ser Pro Val Ile Pro Leu Leu His Leu Gly
            20                  25

<210> SEQ ID NO 2
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Trp Lys Leu Phe Lys Lys Ile Gly Ile Gly Lys Val Leu His Val
1               5                   10                  15

Leu Thr Thr Gly
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Trp Lys Leu Phe Lys Lys Ile Gly Ile Gly Ala Val Leu Lys Val
1               5                   10                  15

Leu Lys Lys Gly
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Trp Lys Leu Phe Lys Lys Ile Gly Ile Gly Ala Val Leu Lys Ser
1               5                   10                  15

Leu Thr Thr Gly
            20

<210> SEQ ID NO 5
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Leu Arg Lys Arg Leu Arg Lys Phe Arg Asn Lys Ile Lys Glu Lys
1               5                   10                  15

Leu Lys Lys Ile Gly Gln Lys Ile Gln Gly Leu Leu Pro Lys Leu Ala
            20                  25                  30

Pro Arg Thr Asp Tyr
        35

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6
```

-continued

Gly Phe Ile Phe His Ile Ile Lys Gly Leu Phe His Ala Gly Lys Met
1               5                   10                  15

Ile His Gly Leu Val
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ile Lys Ile Ala Lys Lys Ala Ile Thr Ile Ala Lys Lys Ile Ala
1               5                   10                  15

Lys Ile Tyr Trp
            20

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Gly Gly Leu Cys Tyr Cys Arg Gly Arg Phe Cys Val Cys Val Gly
1               5                   10                  15

Arg

<210> SEQ ID NO 9
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Met Trp Ser Gly Met Trp Arg Arg Lys Leu Lys Lys Leu Arg Asn
1               5                   10                  15

Ala Leu Lys Lys Lys Leu Lys Gly Glu
            20                  25

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Leu Phe Arg Lys Leu Thr His Arg Leu Phe Arg Arg Asn Phe Gly
1               5                   10                  15

Tyr Thr Leu Arg
            20

<210> SEQ ID NO 11
<211> LENGTH: 25
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 11

Gly Trp Lys Lys Trp Phe Asn Arg Ala Lys Lys Val Gly Lys Thr Val
1               5                   10                  15

Gly Gly Leu Ala Val Asp His Tyr Leu
            20                  25

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Leu Gly Ser Val Phe Gly Arg Leu Ala Arg Ile Leu Gly Arg Val
1               5                   10                  15

Ile Pro Lys Val
            20

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Arg Leu Ile Arg Leu Ile Leu Arg Leu Leu Arg
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Leu Arg Arg Ile Lys Ala Trp Leu Arg Arg Ile Lys Ala
1               5                   10

<210> SEQ ID NO 16
<211> LENGTH: 24
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 16

Leu Lys Arg Leu Tyr Lys Arg Val Phe Arg Leu Leu Lys Arg Tyr Tyr
1               5                   10                  15

Arg Gln Leu Arg Arg Pro Val Arg
            20

<210> SEQ ID NO 17
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Lys Arg Leu Tyr Lys Arg Leu Ala Lys Leu Ile Lys Arg Leu Tyr
1               5                   10                  15

Arg Tyr Leu Lys Lys Pro Val Arg
            20

<210> SEQ ID NO 18
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Gly Leu Arg Arg Leu Gly Arg Lys Ile Val His Val Val Lys Lys
1               5                   10                  15

Tyr Leu Pro Thr Val Leu Arg Ile Ile Arg Ile Ala
            20                  25

<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Gly Leu Arg Arg Leu Gly Arg Lys Ile Val His Val Val Lys Lys
1               5                   10                  15

Tyr Leu Pro Thr Val Leu Arg Ile Ile Arg Arg Leu
            20                  25

<210> SEQ ID NO 21
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Ile His His Ile Ile Gly Gly Leu Phe Ser Ala Gly Lys Ala Ile
1               5                   10                  15

His Arg Leu Ile Arg Arg Arg Arg Arg
            20                  25

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Phe Arg Arg Leu Arg Lys Lys Phe Arg Lys Arg Leu Lys Lys Ile
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Phe Arg Arg Leu Arg Lys Lys Trp Arg Lys Arg Leu Lys Lys Ile
1               5                   10                  15

<210> SEQ ID NO 24
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(27)
<223> OTHER INFORMATION: D-amino acid

<400> SEQUENCE: 24

Gly Arg Phe Lys Arg Phe Arg Lys Lys Phe Lys Lys Leu Phe Lys Lys
1               5                   10                  15

Leu Ser Pro Val Ile Pro Leu Leu His Leu Gly
            20                  25

<210> SEQ ID NO 25
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Leu Arg Lys Arg Leu Arg Lys Phe Arg Asn Lys Ile Lys Glu Lys
1               5                   10                  15

```
Ile Lys Lys Ile Gly Gln Lys Ile Gln Gly Leu Leu Pro Lys Leu Ala
            20                  25                  30

Pro Arg Thr Asp Tyr
        35

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Lys Arg Leu Tyr Lys Arg Val Phe Arg Leu Leu Lys Arg Tyr Tyr
1               5                   10                  15

Gly Gln Leu Arg Arg Pro Val Arg
            20
```